United States Patent
Page et al.

(10) Patent No.: US 7,351,413 B2
(45) Date of Patent: Apr. 1, 2008

(54) STABILIZED HBC CHIMER PARTICLES AS IMMUNOGENS FOR CHRONIC HEPATITIS

(75) Inventors: Mark Page, Allestree (GB); Martin Friede, Nyon (CH); Annette Elisabeth Schmidt, Planegg (DE); Detlef Stober, Munich (DE)

(73) Assignee: Lorantis, Limited, Cambridge (GB)

( * ) Notice: Subject to any disclaimer, the term of this patent is extended or adjusted under 35 U.S.C. 154(b) by 218 days.

(21) Appl. No.: 10/677,074

(22) Filed: Oct. 1, 2003

(65) Prior Publication Data

US 2004/0156863 A1 Aug. 12, 2004

Related U.S. Application Data

(63) Continuation-in-part of application No. 10/372,076, filed on Feb. 21, 2003, now abandoned.

(51) Int. Cl.
```
A61K 39/00      (2006.01)
A61K 39/12      (2006.01)
A61K 39/29      (2006.01)
A61K 39/39      (2006.01)
A61K 9/107      (2006.01)
C07K 14/00      (2006.01)
C07K 14/02      (2006.01)
C07K 14/005     (2006.01)
```
(52) U.S. Cl. .................. 424/192.1; 424/184.1; 424/189.1; 424/204.1; 424/227.1; 424/278.1; 530/350

(58) Field of Classification Search ............. 424/184.1, 424/185.1, 186.1, 189.1, 192.1, 193.1, 196.11, 424/204.1, 225.1, 227.1, 278.1, 279.1, 282.1, 424/283.1; 530/300, 350, 402, 403; 435/65.3; 536/1.11, 23.1

See application file for complete search history.

(56) References Cited

U.S. PATENT DOCUMENTS

| | | | |
|---|---|---|---|
| 4,539,205 A | 9/1985 | Goodman et al. | 514/45 |
| 4,643,992 A | 2/1987 | Goodman et al. | 514/45 |
| 4,767,842 A | 8/1988 | Stevens | 530/324 |
| 4,818,527 A | 4/1989 | Thornton et al. | 424/88 |
| 4,882,145 A | 11/1989 | Thornton et al. | 424/88 |
| 4,977,092 A | 12/1990 | Bitter | 435/320 |
| 5,011,828 A | 4/1991 | Goodman et al. | 514/45 |
| 5,057,540 A | 10/1991 | Kensil et al. | 514/25 |
| 5,093,318 A | 3/1992 | Goodman et al. | 514/45 |
| 5,143,726 A | 9/1992 | Thornton et al. | 424/88 |
| 5,478,726 A | 12/1995 | Shinnick et al. | 435/724 |
| 5,656,472 A | 8/1997 | Ausich et al. | 435/193 |
| 5,709,879 A | 1/1998 | Barchfeld et al. | 424/450 |
| 5,990,085 A | 11/1999 | Ireland et al. | 514/12 |
| 6,020,167 A | 2/2000 | Thoma | |
| 6,024,961 A | 2/2000 | Curtiss, III et al. | 424/200 |
| 6,086,901 A | 7/2000 | O'Hagan et al. | 424/283.1 |
| 6,113,918 A | 9/2000 | Johnson et al. | |
| 6,194,388 B1 * | 2/2001 | Krieg et al. | 514/44 |
| 6,303,347 B1 | 10/2001 | Johnson et al. | |
| 6,355,257 B1 | 3/2002 | Johnson et al. | |
| 6,942,866 B2 * | 9/2005 | Birkett | 424/268.1 |
| 6,964,769 B2 | 11/2005 | Sebbel et al. | |
| 2003/0092643 A1 | 5/2003 | Johnson et al. | |

FOREIGN PATENT DOCUMENTS

| | | | |
|---|---|---|---|
| EP | WO 92/11368 | * | 7/1992 |
| EP | 671 948 B1 | | 9/1995 |
| EP | 689 454 B1 | | 1/1996 |
| WO | WO 95/17210 | | 6/1995 |
| WO | WO 96/02555 | | 2/1996 |
| WO | WO 96/33739 | | 10/1996 |
| WO | WO 99/07839 | | 2/1999 |
| WO | WO 99/12565 | | 3/1999 |
| WO | WO 99/52549 | | 10/1999 |
| WO | WO 99/56776 | | 11/1999 |
| WO | WO 01/16163 A2 | | 3/2001 |
| WO | WO 01/27281 | | 4/2001 |
| WO | WO 01/98333 | | 12/2001 |
| WO | WO 02/13765 | | 2/2002 |

(Continued)

OTHER PUBLICATIONS

Akira et al., "Recognition of pathogen-associated molecular patterns by TLR family," Immunology Letters, vol. 85 No. 2, pp. 85-95 (Jan. 2003).*

(Continued)

*Primary Examiner*—Zachariah Lucas
(74) *Attorney, Agent, or Firm*—Welsh & Katz, Ltd.

(57) ABSTRACT

A method of treating chronic hepatitis B is disclosed that comprises administering a T cell-stimulating amount of a vaccine to a patient. The vaccine comprises an immunogenic amount of chimeric, carboxy-terminal truncated hepatitis B virus nucleocapsid (core) protein (HBc) that is engineered for both enhanced stability of self-assembled particles and the substantial absence of nucleic acid binding by those particles. The chimeric protein molecule can include one or more immunogenic epitopes peptide-bonded to one or more of the N-terminus, the immunogenic loop or the C-terminus of HBc. The enhanced stability of self-assembled particles is obtained by the presence of at least one heterologous cysteine residue near one or both of the amino-terminus and carboxy-terminus of the chimer molecule.

12 Claims, 8 Drawing Sheets

FOREIGN PATENT DOCUMENTS

| WO | WO 02/14478 | 2/2002 |
|---|---|---|
| WO | WO 2005/055957 A1 | 6/2005 |

OTHER PUBLICATIONS

Bowie et al., "Deciphering the Message in Protein Sequences: Tolerance to Amino Acid Substitutions," Science, vol. 247 No. 4948, pp. 1306-1310 (Mar. 1990).*
Jung et al., "Activation of a heterogeneous hepatitis B (HB) core and e antigen-specific CD4+ T-cell population during seroconversion to anti-HBe and anti-HBs in hepatitis B virus infection," Journal of Virology, vol. 69 No. 6, pp. 3358-3368 (Jun. 1995).*
Lebray et al., "Immunomodulatory drugs and therapeutic vaccine in chronic hepatitis B infection," Journal of Hepatology, vol. 39 Supp 1, pp. S151-159 (2003).*
Riffkin et al., "A single amino-acid change between the antigenically different extracellular serine proteases V2 and B2 from Dichelobacter nodosus," Gene, vol. 167 No. 1-2, pp. 279-283 (Dec. 1995).*
Sarobe et al., "Enhanced In Vitro Potency and In Vivo Immunogenicity of a CTL Epitope from Hepatitis C Virus Core Protein following Amino Acid Replacement at Secondary HLA-A2.1 Binding Positions," Journal of Clinical Investigation, vol. 102 No. 6, pp. 1239-1248 (Sep. 1998).*
Sieling and Modlin, "Toll-like receptors: mammalian 'taste receptors' for a smorgasbord of microbial invaders," Current Opinion in Microbiology, vol. 5 No. 1, pp. 70-75 (Feb. 2002).*
Sprengers et al., "Immunomodulatory therapy for chronic hepatitis B infection," Fundament & Clinical Pharmacology, vol. 19 No. 1, pp. 17-26 (Feb. 2001).*
Yuen et al., "Treatment of chronic hepatitis B," The Lancet: Infectious Diseases, vol. 1 No. 4, pp. 232-241 (Nov. 2001).*
BLAST search results- Seq ID No. 28, translated query verse protein database.*
Zhou et al., "Cys residues of the hepatitis B virus capsid protein are not essential for the assembly of viral core particles but can influence their stability," Journal of Virology, vol. 66 No. 9, pp. 5393-5398 (Sep. 1992).*
Couillin et al. (1999) J. of Infect. Dis., 180: 15-26.
Bocher et al. (2001) E. J. of Immun., 31:2071-2079.
Lau et al. (2002) Gastroenterology, 122:614-624.
Sallberg et al., (1998) Human Gene Therapy 10:1719-1729.
Pumpens et al. Intervirology (1995) 38:63-74.
Metzger et al. J. Gen. Viol. (1998) 79:587-590.
Conway et al. Nature (1997) 386:91-94.
Bottcher et al. Nature (1997) 386:88-91.
Zheng et al. J. Biol. Chem. (1992) 267(13):9422-9429.
Birnbaum et al., (1990) J.Virol. 64, 3319-3330.
Clarke et al. (1991) F. Brown et al. eds., Vaccines 91, Cold Spring Harbor Laboratory, Cold Spring Harbor, New York, pp. 313-318.
Seifer et al., (1995) Intervirology, 38:47-62.
Zlotnick et al., (1997) Proc. Natl. Acad. Sci., USA, 94:9556-9561.
Gallina et al. (1989) J.Virol., 63:4645-4652.
Inada, et al. (1989) Virus Res., 14:27-48.
Maassen et al., (1994) Arch. Virol., 135:131-142.
Schodel et al., (1994) J.Exp.Med., 180:1037-1046.
Schodel et al. (1994) Infect. Immunol., 62:1669-1676.
Kratz et al., (1999) Proc. Natl. Acad. Sci., U.S.A., 96:1915-1920.
Ulrich et al. Adv. Virus Res., 50: 141-182 (1998) Academic Press.
Neirynck et al., (Oct. 1999) Nature Med., 5(10):1157-1163.
Schodel et al. (Jan. 15, 1993) J. Biol. Chem., 268(2):1332-1337.
Wasenauer et al. (Mar. 1993) J. Virol., 67(3):1315-1322.
Nassal et al. (Jul. 1993) J. Virol., 67(7):4307-4315.
Galibert et al. (1983) Nature, 281:646-650.
Ono et al. (1983) Nucleic Acids Res., 11(6): 1747-1757.
Valenzuela et al., Animal Virus Genetics, Field et al. eds., Academic Press, New York (1980)pp. 57-70.
Pasek et al., "Hepatitis B virus genes and their expression in E. coli", Nature (Dec. 1979) 282:575-579.
Galibert et al. (1982) J. Virol., 41:51-65.
Seeger et al. (1984) J. Virol.,51:367-375.
"IUPAC-IUB Commission on Biochemical Nomenclature A One-Letter Notation for Amino Acid Sequences[1-3] Tentative Rules", J. Biol. Chem. (Jul. 1968) 243(13):3557-3559.
Karpenko et al., Amino Acids (2000) 18:329-337.
Koschel et al. (Mar. 1999), J. Virol., 73(3):2153-2160.
Schodel et al., "Hybrid Hepatitis-B Virus Core/Pre-S Particles Expressed In Live Attenuated Salmonellae for Oral Immunization", Vaccines (1991) 91, Cold Spring Harbor Laboratory, New York, pp. 319-325.
Schodel et al., Behring Inst. Mitt., 1997(98): p. 114-119.
Schodel et al., "Recombinant HBV Core Particles Carrying Immunodominant B-Cell Epitopes of the HBV Pre-S2 Region", Vaccines (1990) 90, Cold Spring Harbor Laboratory, New York, pp. 193-198.
Poszkowski et al. (1989) EMBO J., 3:2719.
Odell et al. Nature (1985), 313:810.
Chua et al. Science (1989), 244:174-181.
Nestle et al (2001) Nature Medicine 7, 761-765.
Lebray et al, Immunomodulatory drugs and therapeutic vaccine in chronic hepatitis B infection, J. of Hepatology, 2003, 39:S151-159.
Nardin et al., Phase I Testing of a Malaria Vaccine Compound of Hepatits B Virus Core Particles Expressing Plasmodium falciparum Circumsporozoite Epitopes, Infection and Immunity, vol. 72, No. 11, pp. 6519-6527 2004.
Oliveira et al, Safety and Enhanced Immunogenicity of a Hepatitis B Core Particle Plasmodium falciparum Malaria Vaccine Formulated in Adjuvant Montanide ISA 720 in a Phase I Trial, Infection and Immunity, Jun. 2005, vol. 73, No. 6, pp. 3587-3597.
PCT/US04/05047 International Search Report, mailed Jul. 17, 2006.
Office Action from Patent and Trademark Office for corresponding U.S. Appl. No. 10/732,862, dated Mar. 17, 2004.
Office Action from Patent and Trademark Office for corresponding U.S. Appl. No. 10/732,862, dated Dec. 17, 2004.
Office Action from Patent and Trademark Office for corresponding U.S. Appl. No. 10/732,862, dated Mar. 3, 2006.
Office Action from Patent and Trademark Office for corresponding U.S. Appl. No. 09/930,915, dated Mar. 6, 2002.
Office Action from Patent and Trademark Office for corresponding U.S. Appl. No. 09/930,915, dated Sep. 17, 2003.
Office Action from Patent and Trademark Office for corresponding U.S. Appl. No. 09/930,915, dated Jan. 9, 2004.
Office Action from Patent and Trademark Office for corresponding U.S. Appl. No. 09/930,915, dated Feb. 3, 2004.
Office Action from Patent and Trademark Office for corresponding U.S. Appl. No. 09/930,915, dated Jul. 26, 2004.
Office Action from Patent and Trademark Office for corresponding U.S. Appl. No. 09/930,915, dated May 9, 2005.
Office Action from Patent and Trademark Office for corresponding U.S. Appl. No. 09/930,915, dated May 9, 2005.
Office Action from Patent and Trademark Office for corresponding U.S. Appl. No. 09/930,915, dated Jul. 10, 2006.
Office Action from Patent and Trademark Office for corresponding U.S. Appl. No. 09/930,915, dated Oct. 24, 2006.
Office Action from Patent and Trademark Office for corresponding U.S. Appl. No. 09/930,915, dated Feb. 23, 2007.
Office Action from Patent and Trademark Office for corresponding U.S. Appl. No. 10/806,006, dated Sep. 24, 2004.
Office Action from Patent and Trademark Office for corresponding U.S. Appl. No. 10/806,006, dated Jun. 20, 2006.
Office Action from Patent and Trademark Office for corresponding U.S. Appl. No. 10/806,006, dated Oct. 17, 2006.
Office Action from Patent and Trademark Office for corresponding U.S. Appl. No. 10/806,006, dated Feb. 26, 2007.
Office Action from Patent and Trademark Office for corresponding U.S. Appl. No. 10/805,913, dated Sep. 29, 2004.
Office Action from Patent and Trademark Office for corresponding U.S. Appl. No. 10/805,913, dated Jun. 22, 2006.
Office Action from Patent and Trademark Office for corresponding U.S. Appl. No. 10/805,913, dated Oct. 17, 2006.
Office Action from Patent and Trademark Office for corresponding U.S. Appl. No. 10/805,913, dated Feb. 23, 2007.

* cited by examiner

FIG. 1A

```
Ground Squirrel  mylfhlclvf acvpcptvga sklclgwlwd

1
HBc AYW          mdidpykefg atvellsflp sdffpsvrdl ldtasalyre
HBc ADW          mdidpykefg atvellsflp sdffpsvrdl ldtasalyre
HBc ADW2         mdidpykefg atvellsflp sdffpsvrdl ldtasalyre
HBc ADYW         mdidpykefg atvellsflp sdffpsvrdl ldtaaalyrd
Woodchuck        mdidpykefg ssyqllnflp ldffpdlnal vdtatalyee
Ground Squirrel  mdidpykefg ssyqllnflp ldffpdlnal vdtaaalyee 41
HBc AYW          alespehcsp hhtalrgail cwgelmtlat wvgvnledpa
HBc ADW          alespehcsp hhtalrgail cwgelmtlat wvgnnlqdpa
HBc ADW2         alespehcsp hhtalrgail cwgelmtlat wvgnnledpa
HBc ADYW         alespehcsp hhtalrgail cwgdlmtlat wvgtnledpa
Woodchuck        eltgrehcsp hhtairqalv cwdeltklia wmssnitseq
Ground Squirrel  eltgrehcsp hhtairqalv cweeltrlit wmsentteev
```

FIG. 1B

```
                   81
HBc AYW                srdlvvsyvn tnmglkfrql lwfhiscltf gretvieylv
HBc ADW                srdlvvnyvn tnmglkirql lwfhiscltf gretvleylv
HBc ADW2               srdlvvsyvn tnvglkirql lwfhiscltf gretvleylv
HBc ADYW               srdlvvsyvn tnvglkfrql lwfhiscltf gretvleylv
Woodchuck              vrtiivnhvn dtwglkvrqs lwfhiscltf gqhtvqeflv
Ground Squirrel        rriivdhvnn twglkvrqtl wfhlscltfg qhtvqeflvs 121
HBc AYW                sfgvwirtpp ayrppnapil stlpettvvr rrgrsprrrt
HBc ADW                sfgvwirtpp ayrppnapil stlpettvvr rrdrgrsprr
HBc ADW2               sfgvwirtpp ayrppnapil stlpettvvr rrdrgrsprr
HBc ADYW               sfgvwirtpp ayrppnapil stlpettvvr rrgrsprrrt
Woodchuck              sfgvwirtpa pyrppnapil stlpehtvir rrggarasrs
Ground Squirrel        fgvwirtpap yrppnapils tlpehtvirr rggsraarsp 161
HBc AYW                psprrrrsqs prrrrsqsre sqc
HBc ADW                rtpsprrrrs qsprrrrsqs resqc
HBc ADW2               rtpsprrrps qsprrrrsqs resqc
HBc ADYW               psprrrrsqs prrrrsqsre sqc
Woodchuck              prrrtpsprr rrsqsprrrr sqc
Ground Squirrel        rrrtpsprrr rsqsprrrrs qspasnc
```

FIG. 2

HindIII pKK223-3

TTCACACAGGAAACAGAATTCCCGGGGATCCGTCGACCTGCAGCCAAG
CTT pKK223-3N       TTCACA<u>TAAGGAGGAAAAA</u>Accatgg GATCCG--
----------AAGCTT NcoI

FIG. 11
Scheme 1
I
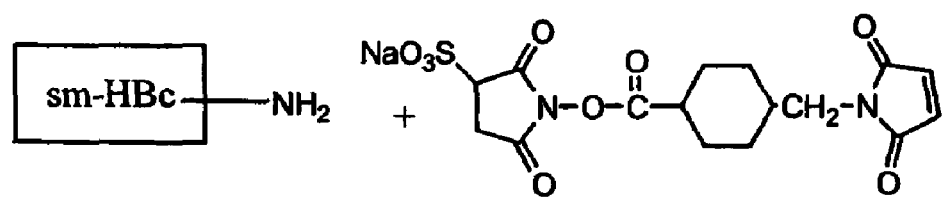
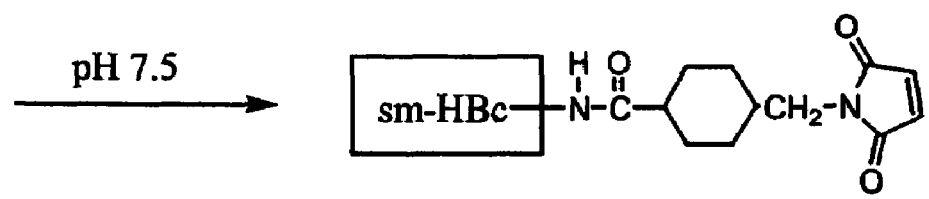
II
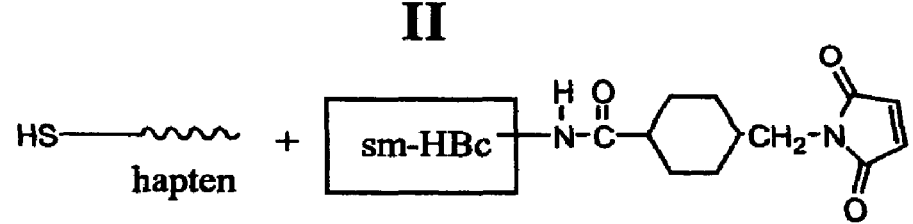
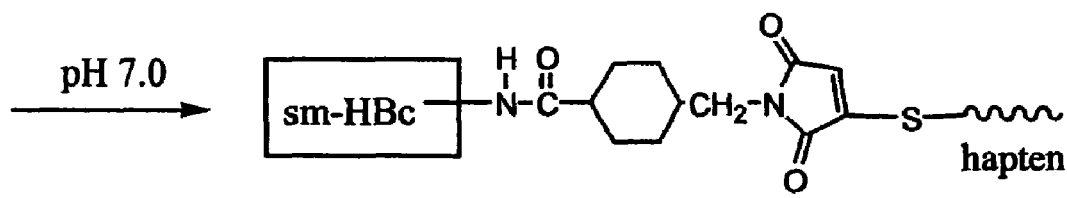

STABILIZED HBC CHIMER PARTICLES AS IMMUNOGENS FOR CHRONIC HEPATITIS

CROSS-REFERENCE TO RELATED APPLICATION

This a continuation-in-part of application Ser. No. 10/372,076 that was filed on Feb. 21, 2003 now abandoned, whose disclosures are incorporated herein by reference.

TECHNICAL FIELD

The present invention relates to the intersection of the fields of immunology and protein engineering, and particularly to a chimeric hepatitis B virus (HBV) nucleocapsid protein that is useful as the immunogen in a vaccine for treating patients with chronic hepatitis by enhancing the immune response towards the hepatitis B virus and is engineered for enhanced stability of self-assembled particles via one or both of a C-terminal and an N-terminal cysteine residue.

BACKGROUND OF THE INVENTION

Over 350 million people worldwide are chronically infected carriers of hepatitis B (HBV). HBV is a virus that infects the liver and causes an increased risk of chronic hepatitis, cirrhosis of the liver, and hepatocellular carcinoma (cancer of the liver). Hepatitis B is the cause of over 80 percent of hepatocellular carcinomas, and claims the lives of 1-2 million people worldwide every year, representing an important public health challenge and a growing market for new therapeutics.

The severity of hepatitis B infection depends on the state of the infected person's immune system at the time of infection. Hepatitis B is most debilitating when it is transmitted from a mother to her baby at birth, as the immune system of an infant is typically not capable of mounting an effective response against the virus. As a result, chronic infection occurs in 90 percent of infants that are infected at birth, and the risk of hepatocellular carcinoma is much higher (20 percent to 30 percent). If infection occurs at 1-5 years of age, the risk of chronic infection drops to 25-50 percent. If infection occurs in late childhood or adulthood, the chances of chronic infection are only 2-6 percent. Hepatocellular carcinoma rarely occurs in people who become chronically infected as adults.

Chronic carriers are highly infectious, and fall into two general categories: (1) asymptomatic chronic persistent hepatitis B, where most chronic carriers do not seek medical attention for their condition, and (2) chronic active hepatitis B that is more serious, but less common, than chronic persistent hepatitis. When symptoms are present in patients with asymptomatic chronic persistent HBV, those symptoms may be relatively minor such as fatigue, abdominal pains, weakness, fever, and intolerance to fat or alcohol. The disease does not usually progress to severe liver disease, but a few patients may develop chronic active hepatitis B. The consequences of chronic active hepatitis B include cirrhosis of the liver and primary hepatocellular carcinoma (PHC). In cirrhosis of the liver, fibrous tissue forms, replacing damaged liver cells. The liver then becomes hardened, enlarged and distorted, and may eventually fail. PHC is relatively rare in areas of low hepatitis B endemicity but is very common, and a frequent cause of death, in areas of high endemicity.

Current treatment for chronic hepatitis B involves taking injections of interferon alfa-2, for four months. There are four brands of interferon alfa-2 approved in the United States: Schering Plough's Intron® A, Amgen's Infergen, Hoffmann-La Roche's Roferon, and GlaxoSmithKline's Wellferon. Intron® A is the only form of alpha interferon that is approved for hepatitis B, the others are approved for hepatitis C only.

Interferon alpha is believed to increase the number of MHC Class I molecules on the surface of liver cells, thereby increasing the ability of immune cells to recognize and destroy the infected liver cells. Interferon alpha also increases the amount of ribonuclease enzymes that cleave HBV-RNA in liver cells, impeding HBV growth.

Although interferon alpha can completely eliminate chronic hepatitis B infections in some people, its use is limited because over half of all patients do not respond to treatment. In people with chronic hepatitis B, interferon alpha may slow the disease by reducing the amount of virus in their bodies and slowing the damage to their livers.

The side effects of interferon alpha-2 treatment can be so debilitating that patients are recommended to take a week or two off work when beginning treatment. The most common side effect are symptoms of the flu-fatigue, fever, muscle pains, general body aches, chills, and nausea. Mild hair thinning and dry, itchy skin can also occur.

Antiviral agents and therapeutic vaccines are being investigated as possible alternative treatment options due to the ineffectiveness and side effects of interferon alpha therapy. Promising results have been seen with second generation nucleoside analogues, such as lamivudine and famciclovir. Zeffix® (lamivudine), a nucleoside reverse transcriptase inhibitor, is a promising single drug candidate as a treatment for chronic hepatitis B, and received FDA approval to be marketed and sold in the United States in 1999. Other antiviral agents under evaluation include BMS200, 475, ganciclovir, and adefovir dipivoxil. Combination therapy of the above candidates with interferon alpha is also being investigated.

Hoffman La Roche and Schering Plough Corporation have recently applied to the U.S. Food and Drug Administration (FDA) for marketing approval of their versions of so-called pegylated interferons named PEGASYS™ (Hoffman La Roche) and PEG-INTRON™ (Schering Plough Corp.). Pegylated interferon are alpha interferons that are modified by polyethylene glycol (PEG) so that they can be given once a week and provide a sustained level of interferon within the patient. The pegylated formulations may avoid the peaks and troughs of interferon levels and interferon side effects that occur when given three times a week. Pegylated interferons may be especially beneficial to those who have relapsed following monotherapy or combination therapy.

Vaccine approaches have been attempted to treat chronic hepatitis. Couillin and colleagues [Couillin et al. (1999) J. of Infect. Dis., 180: 15-26] evaluated whether vaccination with hepatitis B surface antigen (HBsAg) was able to overcome the tolerance to HBsAg in patients with chronic hepatitis. They determined that HBsAg was effective in a fraction of the population.

Studies have also been performed in animal models to evaluate whether an immune response can be induced in animal models of the disease. Thus, Bocher and colleagues [Bocher et al. (2001) E. J. of Immun., 31:2071-2079] evaluated the immune response towards vaccination in a humanized (trimera) mouse model. As a model of the disease, these authors transferred PBMCs from patients chronically infected with hepatitis B into the mice, and then vaccinated the mice with hepatitis B core protein (HBc) or DNA coding for hepatitis B core protein. The authors noted that HBc-specific T-helper-cell and B-cell responses were induced when the mice were immunized with HBc or with DNA coding for HBC. The authors noted that either HBc protein or HBc-encoding DNA could represent candidate vaccines for therapeutic vaccination against chronic hepatitis B infection. It should be noted that in these studies very large doses of HBc were required to induce an immune response. The immune response in mice grafted with PBMCs from infected individuals could further be enhanced by the addition of immunostimulatory oligonucleotides (ISN).

In addition to considering active vaccination, passive transfer of immunity has been attempted: Lau and colleagues [Lau et al. (2002) Gastroenterology, 122:614-624] demonstrated that bone-marrow transfers from HBV-immune individuals to chronically infected individuals resulted in resolution of the infection. The resolution was associated with the transfer of T-cells reactive to HBc, leading those authors to postulate that therapeutic immunization with HBc protein or [HBc-encoding] DNA deserves investigation in patients with chronic hepatitis B infection.

Hepatitis B core protein (HBc) has therefore been recognized as a potentially useful antigen for therapeutic vaccination against chronic hepatitis B infection. Several problems however, have to be overcome to turn that potential into practice: the recombinant production of HBc is difficult. As discussed hereinafter the yield of production is very low, possibly because of the inherent nucleic-acid binding property of the HBc protein, and the resulting virus-like-particle (VLP) is furthermore difficult to purify to a level acceptable to regulatory authorities.

As a result of the difficulties associated with manufacturing HBc, alternative approaches have been pursued to induce an immune response to HBc in individuals chronically infected with HBV. Thus, for example, WO 01/16163 assigned to Hultgren and Sallberg proposes the use of multiple overlapping synthetic peptides comprising several amino acid residue sequences spanning the position 1-183 sequence of HBc. These inventors suggested that immunization with a mixture of peptides spanning the entire protein may induce an immune response that promotes clearance of the virus in chronically infected individuals. DNA encoding the HBc protein has been used to immunize chimpanzees chronically infected with HBV [Sallberg et al., (1998) Human Gene Therapy 10:1719-1729]. The use of DNA encoding a protein overcomes the requirement for purification of the protein, but DNA-vaccination has not been associated with a significant rate of success in humans.

U.S. Pat. No. 6,020,167 to Thoma discloses a vaccine that is said to be useful in treating chronic HBV infection. This vaccine comprises a polypeptide having one or more HBV pre-S1 or HBV core T-cell activating epitopes bound to a carrier capable of presenting the polypeptide. Particle-forming carriers were said to be preferred, with complete or substantial parts of the HBV core and surface proteins (HBc and HbsAg, respectively) being claimed carriers. As is discussed hereinafter, the complete core protein tends to bind nucleic acids, which can be problematic for vaccine manufacture. In addition, core molecules that are carboxy-terminally truncated to alleviate the nucleic acid binding, may be unstable and can provide a heterogeneous mixture in a vaccine.

The family hepadnaviridae are enveloped DNA-containing animal viruses that can cause hepatitis B in humans (HBV). The hepadnavirus family includes hepatitis B viruses of other mammals, e.g., woodchuck (WHV), and ground squirrel (GSHV), and avian viruses found in ducks (DHV) and herons (HeHV). Hepatitis B virus (HBV) used herein refers to a member of the family hepadnaviridae that infects mammals, as compared to a virus that infects an avian host, unless the discussion refers to a specific example of a non-mammalian virus.

The nucleocapsid or core of the mammalian hepatitis B virus (HBV or hepadnavirus) contains a sequence of 183 or 185 amino acid residues, depending on viral subtype, whereas the duck virus capsid contains 262 amino acid residues. Hepatitis B core protein monomers of the several hepadnaviridae self-assemble in infected cells into stable aggregates known as hepatitis B core protein particles (HBc particles). Two three-dimensional structures are reported for HBc particles. A first that comprises a minor population contains 90 copies of the HBc subunit protein as dimers or 180 individual monomeric proteins, and a second, major population that contains 120 copies of the HBc subunit protein as dimers or 240 individual monomeric proteins. These particles are referred to as T=4 or T=3 particles, respectively, wherein "T" is the triangulation number. These HBc particles of the human-infecting virus (human virus) are about are about 30 or 34 nm in diameter, respectively. Pumpens et al. (1995) *Intervirology*, 38:63-74; and Metzger et al. (1998) *J. Gen. Viol.*, 79:587-590.

Conway et al., (1997) *Nature*, 386:91-94, describe the structure of human HBc particles at 9 Angstrom resolution, as determined from cryo-electron micrographs. Bottcher et al. (1997), *Nature*, 386:88-91, describe the polypeptide folding for the human HBc monomers, and provide an approximate numbering scheme for the amino acid residues at which alpha-helical regions and their linking loop regions form. Zheng et al. (1992), *J. Biol. Chem.*, 267(13):9422-9429 report that core particle formation is not dependent upon the arginine-rich C-terminal domain, the binding of nucleic acids or the formation of disulfide bonds based on their study of mutant proteins lacking one or more cysteines and others' work with C-terminal-truncated proteins [Birnbaum et al., (1990) *J. Virol.* 64, 3319-3330].

The hepatitis B nucleocapsid or viral core protein (HBc) has been disclosed as an immunogenic carrier moiety that stimulates the T cell response of an immunized host animal. See, for example, U.S. Pat. No. 4,818,527, No. 4,882,145 and No. 5,143,726. A particularly useful application of this carrier is its ability to present foreign or heterologous B cell epitopes at the site of the immunodominant loop that is present at about residue positions 70-90, and more usually recited as about positions 75 to 85 from the amino-terminus (N-terminus) of the protein. Clarke et al. (1991) F. Brown et al. eds., *Vaccines* 91, Cold Spring Harbor Laboratory, Cold Spring Harbor, N.Y., pp.313-318.

During viral replication, HBV nucleocapsids associate with the viral RNA pre-genome, the viral reverse transcriptase (Pol), and the terminal protein (derived from Pol) to form replication competent cores. The association between the nucleocapsid and the viral RNA pre-genome is mediated by an arginine-rich domain at the carboxyl-terminus (C-terminus). When expressed in heterologous expression systems, such as *E. coli* where viral RNA pre-genome is absent, the protamine-like C-terminus; i.e., residues at positions 150 through 183, can bind *E. coli* RNA. Zhang et al. (1992) *JBC*, 267(13) 9422-29.

In an application as a vaccine moiety, it is preferable that the HBV nucleocapsids not bind nucleic acid derived from the host. Birnbaum et al. (1990) *J. Virol.*, 64:3319-3330 showed that the protamine-like C-terminal domain of HBV nucleocapsids could be deleted without interfering with the protein's ability to assemble into virus-like particles. It is thus reported that proteins truncated to about position 144; i.e., containing the HBc sequence from position one through about 144, can self-assemble, whereas deletions beyond residue 139 abrogate capsid assembly [Birnbaum et al., (1990) *J. Virl.*, 64: 3319-30; and Seifer et al., (1995) *Intervirology*, 38:47-62].

Zlotnick et al., (1997) *Proc. Natl. Acad. Sci., USA*, 94:9556-9561 studied the assembly of full length and truncated HBc proteins in to particles. In addition to discussing full length molecules, those authors reported the preparation of a truncated protein that contained the HBc sequence from position 1 through 149 in which the cysteines at positions 48, 61 and 107 were each replaced by alanines and in which a cysteine residue was added at the C-terminus (position 150). That C-terminal mercaptan was used for linkage to a gold atom cluster for labeling in electron microscopy.

More recently, Metzger et al. (1998) *J. Gen. Viol.*, 79:587-590 reported that the proline at position 138 (Pro-138 or P138) of the human viral sequence is required for particle formation. Those authors also reported that assembly capability of particles truncated at the carboxy-terminus to lengths of 142 and 140 residues was affected, with assembly capability being completely lost with truncations resulting in lengths of 139 and 137 residues.

Several groups have shown that truncated particles exhibit reduced stability relative to standard hepatitis B core particles [Galena et al. (1989) *J. Virol.*, 63:4645-4652; Inada, et al. (1989) *Virus Res.*, 14:27-48], evident by variability in particle sizes and the presence of particle fragments in purified preparations [Maassen et al., (1994) *Arch. Virol.*, 135:131-142). Thus, prior to the report of Metzger et al., above, Pumpens et al., (1995) *Intervirology*, 38:63-74 summarized the literature reports by stating that the carboxy-terminal border for HBc sequences required for self-assembly was located between amino acid residues 139 and 144, and that the first two or three amino-terminal residues could be replaced by other sequences, but elimination of four or eleven amino-terminal residues resulted in the complete disappearance of chimeric protein in transformed *E. coli* cells.

Recombinantly-produced hybrid HBc particles bearing internal insertions (referred to in the art as HBc chimeric particles or HBc chimers) containing various inserted polypeptide sequences have been prepared by heterologous expression in a wide variety of organisms, including *E. coli, B. subtilis, Vaccinia, Salmonella typhimurium, Saccharomyces cerevisiae*. See, for example Pumpens et al. (1995) *Intervirology*, 38:63-74, and the citations therein that note the work of several research groups.

Such HBc chimers often appear to have a less ordered structure, when analyzed by electron microscopy, compared to particles that lack heterologous epitopes [Schodel et al., (1994) *J. Exp. Med.*, 180:1037-1046]. In some cases the insertion of heterologous epitopes into C-terminally truncated HBc particles has such a dramatic destabilizing affect that hybrid particles cannot be recovered following heterologous expression [Schodel et al. (1994) *Infect. Immunol.*, 62:1669-1676]. Thus, many chimeric HBc particles are so unstable that they fall apart during purification to such an extent that they are unrecoverable or they show very poor stability characteristics, making them problematic for vaccine development.

The above Pumpens et al. (1995) *Intervirology*, 38:63-74 report lists particle-forming chimers in which the inserted polypeptide sequence is at the N-terminus, the C-terminus and between the termini. Insert lengths reported in that article are 24 to 50 residues at the N-terminus, 7 to 43 residues internally, and 11 to 741 residues at the C-terminus.

Kratz et al., (1999) *Proc. Natl. Acad. Sci., U.S.A.*, 96:1915-1920 recently described the *E. coli* expression of chimeric HBc particles comprised of a truncated HBc sequence internally fused to the 238-residue green fluorescent protein (GFP). This chimer contained the inserted GFP sequence flanked by a pair of glycine-rich flexible linker arms replacing amino acid residues 79 and 80 of HBc. Those particles were said to effectively elicit antibodies against native GFP in rabbits as host animals.

U.S. Pat. No. 5,990,085 describes two fusion proteins formed from an antigenic bovine inhibin peptide fused into (i) the immunogenic loop between residues 78 and 79 and (ii) after residue 144 of carboxy-terminal truncated HBc. Expressed fusion proteins were said to induce the production of anti-inhibin antibodies when administered in a host animal. The titers thirty days after immunization reported in that patent are relatively low, being 1:3000-15,000 for the fusion protein with the loop insertion and 1:100-125 for the insertion after residue 144.

U.S. Pat. No. 6,231,864 teaches the preparation and use of a strategically modified hepatitis B core protein that is linked to a hapten. The modified core protein contains an insert of one to about 40 residues in length that contains a chemically reactive amino acid residue to which the hapten is pendently linked.

WO 01/27281 teaches that the immune response to HBc can be changed from a Th1 response to a Th2 response by the presence or absence, respectively, of the C-terminal cysteine-containing sequence of the native molecule. That disclosure also opines that disulfide formation by C-terminal cysteines could help to stabilize the particles. The presence of several residues the native HBc sequence immediately upstream of the C-terminal cysteine was said to be preferred, but not required. One such alternative that might be used to replace a truncated C-terminal HBc sequence was said to include a C-terminal cysteine and an optional sequence that defines an epitope from other than HBc.

Published PCT application WO 01/98333 teaches the deletion of one or more of the four arginine repeats present at the C-terminus of native HBc, while maintaining the C-terminal cysteine residue. That application also teaches that the deleted region can be replaced by an epitope from a protein other than HBc so that the HBc portion of the molecule so formed acts as a carrier for the added epitope.

Published PCT applications corresponding to PCT/US01/25625 (WO 02/13765 A2 published Feb. 21, 2002) and PCT/US01/41759 (WO 02/14478 A2 published Feb. 21, 2002) teach that stabilization of C-terminally truncated HBc particles can be achieved through the use of one or more added cysteine residues in the chimer proteins from which the particles are assembled. Those added cysteine residues are taught to be at on near the C-terminus of the chimeric protein.

A structural feature whereby the stability of full-length HBc particles could be retained, while abrogating the nucleic acid binding ability of full-length HBc particles, would be highly beneficial in vaccine development using the hepadnaviral nucleocapsid delivery system. Indeed, Ulrich et al. in their recent review of the use of HBc chimers as carriers for foreign epitopes [*Adv. Virus Res.*, 50: 141-182 (1998) Academic Press] note three potential problems to be solved for use of those chimers in human vaccines. A first potential problem is the inadvertent transfer of nucleic acids in a chimer vaccine to an immunized host. A second potential problem is interference from preexisting immunity to HBc. A third possible problem relates to the requirement of reproducible preparation of intact chimer particles that can also withstand long-term storage.

The above four published PCT applications appear to contain teachings that can be used to overcome the potential problems disclosed by Ulrich et al. As disclosed hereinafter, the present invention provides another HBc chimer that provides unexpectedly high titers of antibodies against influenza, and in one aspect also provides a solution to the problems of HBc chimer stability as well as the substantial absence of nucleic acid binding ability of the construct. In addition, a contemplated recombinant chimer exhibits minimal, if any, antigenicity toward preexisting anti-HBc antibodies.

The above particle instability findings related to N-terminal truncated HBc chimer molecules notwithstanding, Neirynck et al., (October 1999) *Nature Med.*, 5(10):1157-1163 reported that particle formation occurred on *E. coli* expression of a HBc chimer that contained the N-terminal 24-residue portion of the influenza M2 protein fused at residue 5 to full length HBc.

The previously discussed use of hybrid HBc proteins with truncated C-termini for vaccine applications offers several advantages over their full-length counterparts, including enhanced expression levels and lack of bound *E. coli* RNA. However, C-terminally truncated particles engineered to display heterologous epitopes are often unstable, resulting in particles that either fail to associate into stable particulate structures following expression, or that readily dissociate into non-particulate structures during and/or following purification. Such a lack of stability is exhibited by particles comprised of chimeric HBc molecules that are C-terminally truncated to HBc position 149 and also contain the above residues 1-24 of the influenza A M2 protein.

Others have reported that in wild type hepadnaviral core antigens a cysteine residue upstream of the HBcAg start codon is directly involved in the prevention of particle formation [Schodel et al. (Jan. 15, 1993) *J. Biol. Chem.*, 268(2):1332-1337; Wasenauer et al. (March 1993) *J. Virol.*, 67(3):1315-1322; and Nassal et al. (July 1993) *J. Virol.*, 67(7):4307-4315]. All three groups reported that in wild type HBeAg, the cysteine residue at position −7 of the pre-core sequence, which is present when the core gene is translated from an upstream initiator methionine at position −30, is responsible for preventing particle formation and therefore facilitating the transition from particulate HBcAg to secreted, non-particulate HBeAg.

One aspect of the present invention discussed hereinafter is to provide a protein immunogen intended for administration to individuals chronically infected with hepatitis B virus that overcomes the above-mentioned problems of production and contamination. Furthermore the protein has been engineered to maintain physical stability, and to induce an immune response particularly useful for clearing the body of an existing hepatitis B viral infection.

The present invention described in detail hereinafter provides a vaccine treatment for chronic hepatitis that overcomes several of the previously observed problems with vaccines. Thus, a contemplated vaccine induces an enhanced immune response by providing T cell activation that is particularly useful for clearing the body of an existing hepatitis B viral infection and utilizes a carrier molecule that is stable and homogeneous while also being substantially free from nucleic acid binding.

BRIEF SUMMARY OF THE INVENTION

The present invention contemplates a method of treating an individual chronically infected with the hepatitis B virus, by administering to that patient a vaccine comprised of recombinant truncated and stabilized hepadnaviral nucleocapsid protein particles dissolved or dispersed in a pharmaceutically acceptable diluent in an amount sufficient to enhance the immune response against the virus to a patient having a chronic hepatitis B virus infection. Such enhancement of the immune response against the virus, alone or in combination with other therapies, can permit the individual to clear the virus from the body and to no longer be infectious. It is preferred that the recombinant truncated and stabilized hepadnaviral nucleocapsid protein be substantially free of host-nucleic acid.

The method utilizes a vaccine comprised of a recombinant hepadnavirus nucleocapsid protein; i.e., a hepatitis B core (HBc) chimeric protein [also referred to herein as a chimer hepatitis B core protein molecule, a HBc chimer molecule or just a chimer] that self-assembles into particles after expression in a host cell and is dissolved or dispersed in a pharmaceutically acceptable diluent. A contemplated chimer molecule is truncated at least at the C-terminus relative to a native core molecule whose C-terminus is usually at about residue position 183. Particles containing a contemplated chimer molecule are preferably stabilized by a cysteine residue at or near one or both of the N- and C-termini. A contemplated chimer molecule contains about 125 to all of the N-terminal 165 amino acid residues of HBc and can include one or more other amino acid residues or residue sequences that are typically B or T cell epitopes of HBV, another pathogen or another protein such as bovine inhibin.

In one aspect of the invention, a contemplated method of treating chronic hepatitis comprises the steps of administering an anti-HBc T cell-stimulating amount of a vaccine comprised of immunogenic particles dissolved or dispersed in a pharmaceutically acceptable diluent to a patient having a chronic hepatitis B virus infection. The immunogenic particles are preferably administered in conjunction with an immunostimulatory adjuvant. Preferred immunostimulatory adjuvants include lipid-A analogues such as monophosphoryl lipid A or synthetic aminoalkyl glucosamide phosphates. The immunostimulatory molecules are preferably associated with a microparticulate carrier such as oil-in-water emulsions or microparticulate mineral salts such as aluminium hydroxide gel. The immunogenic particles are themselves comprised of recombinant hepatitis B core (HBc) chimeric protein molecules, with the chimeric protein molecules being up to about 550 amino acid residues in length. Those chimeric protein molecules (a) contain an HBc sequence of about 125 to all of the N-terminal 165 amino acid residues of the HBc molecule and contains the HBc sequence of residue positions 4 through about 75 and about 85 through about 140. The HBc chimer molecule sequence optionally includes (a') a peptide-bonded amino acid sequence containing an immunogenic epitope at one or more of the N-terminus, in the HBc immunodominant loop (i.e., between residue positions about 76 through about 85) and the C-terminus of the chimer, or (b') an insert in the HBc immunodominant loop having a length of one to about 40 amino acid residues and containing a chemically-reactive linker residue for a conjugated hapten, or (c') zero to all of the residues of the sequence of positions 76 through 85.

The chimeric protein molecule also contains one or both of (a') one to three cysteine residues at an amino acid position of the chimer molecule corresponding to amino acid position −20 to about +1 from the N-terminus of the HBc sequence of SEQ ID NO:1 [N-terminal cysteine residue(s)] in a sequence other than that of the HBc precore sequence and (b') one to about three cysteine residues toward the C-terminus of the molecule from the C-terminal residue of the HBc sequence and within about 30 residues from the C-terminus of the chimer molecule [C-terminal cysteine residue(s)].

A chimeric protein molecule contains no more than about 20 percent conservatively substituted amino acid residues in the HBc sequence, and self-assembles into particles. Those particles are preferably substantially free of binding to nucleic acids (exhibits a ratio of absorbance at 280 nm to 260 nm of about 1.2 to about 1.7, as discussed hereinafter) on expression in a host cell (followed by collection and purification), but can also include a minimal amount of bound nucleic acid such that the ratio of absorbance at 280 nm to 260 nm is about 0.9 to about 1.15. Thus, particles that exhibit a ratio of absorbance at 280 nm to 260 nm of about 0.9 to about 1.7 can be used herein. The particles are more stable than are particles (i) formed from otherwise identical HBc chimer molecules that are free of any above-mentioned C-terminal cysteine residue(s) or N-terminal cysteine residue(s) or (ii) in which a C-terminal or an N-terminal cysteine residue(s) present in a contemplated chimer molecule is (are) replaced by another residue.

The patient is maintained for a time sufficient to induce T cells activated against HBc. In other aspects of the invention the patient is treated with an antiviral medicament such as lamivudine to reduce viral burden. The treatment with an antiviral can be concurrent with vaccination, or can precede vaccination. A contemplated aspect of the invention includes a kit comprising both antiviral medicament and HBc chimer intended for administration to patients.

In other aspects of the invention, the patient has serum that contains HbsAg, and the treatment results in decreasing the amount of that antigen in the patient's serum. In a further aspect of the invention, the patient's serum contains HBeAg, and the treatment results in decreasing the amount of the HBeAg antigen in the patient's serum.

A preferred recombinant hepatitis B virus core (HBc) protein chimer molecule has a length of about 135 to about 525 amino acid residues that contains four peptide-linked amino acid residue sequence domains from the N-terminus that are denominated Domains I, II, III and IV.

Domain I of that chimer molecule comprises about 71 to about 110 amino acid residues whose sequence includes (i) at least the sequence of the residues of position 5 through position 75 of HBc, (ii) zero to three cysteine residues at an amino acid position of the chimer molecule corresponding to amino acid position −20 to about +1 from the N-terminus of the HBc sequence of SEQ ID NO:1 [N-terminal cysteine residue(s)] in a sequence other than that of the HBc precore sequence, and (iii) an optional immunogenic epitope containing up to about 30 amino acid residues peptide-bonded to one of HBc residues 2-4.

Domain II of that chimer molecule comprises up to about 255 amino acid residues peptide-bonded to HBc residue 75 of Domain I in which (i) zero to all residues in the sequence of HBc positions 76 through 85 are present peptide-bonded to (ii) an optionally present sequence of one to about 245 amino acid residues that constitute an immunogenic epitope or a linker residue for a conjugated epitope.

Chimer Domain III is an HBc sequence from position 86 through position 135 peptide-bonded to residue 85 of Domain II.

Chimer molecule Domain IV comprises (i) five through thirty residues of an HBc amino acid residue sequence from position 136 through 165 peptide-bonded to the residue of position 135 of Domain III, (ii) zero to three cysteine residues [C-terminal cysteine residue(s)] within about 30 residues from the C-terminus of the chimer molecule, and (iii) zero to about 100 amino acid residues in an immunogenic sequence other than that present in HBc from position 165 to the C-terminus.

A preferred chimer molecule (i) has an amino acid residue sequence in which no more than about 10 percent of the amino acid residues are substituted in the HBc sequence of the chimer and (ii) self-assembles into particles on expression by a host cell. The particles are substantially free of binding to nucleic acids and are more stable than are particles formed from otherwise identical HBc chimer molecules that are free of any above-mentioned C-terminal cysteine residue(s) and (i) lack the N-terminal cysteine residue(s) or (ii) in which an N-terminal cysteine residue(s) present in a contemplated chimer molecule is (are) replaced by another residue.

In some embodiments, it is preferred that the HBc sequence of Domain I include the residues of position 5 through position 75 along plus at least an N-terminal cysteine residue. In other embodiments, it is preferred that a contemplated chimer molecule contain not only an N-terminal cysteine residue, but also contain one cysteine residue within Domain IV as noted above that is alone or in an amino acid residue sequence. In yet other embodiments, a preferred chimer molecule contains only one or more C-terminal cysteine residues and Domain I is free of non-HBc cysteine residues. A cysteine residue is present at about position 61 in each of the HBc sequences of FIG. 1.

A contemplated method utilizes a vaccine that comprises before-mentioned self-assembled chimer molecule particles dissolved or dispersed in a pharmaceutically acceptable diluent composition that typically also contains water. A particularly preferred non-HBc epitope present in a contemplated chimer molecule at one or more of Domains I, II and III is an immunogenic sequence from the pres1 or preS2 regions of the hepatitis B surface protein (HBs).

The present invention has several benefits and advantages.

A particular benefit of the invention is that its use as a therapeutic vaccine provides extraordinary T cell activation.

Another benefit of the invention is that the recombinant immunogen is prepared easily and using well known cell culture techniques.

An advantage of the invention is that the immunogen is easily prepared using well known recombinant techniques.

Another advantage of the invention is that a preferred immunogen exhibits greater stability on preparation than do other HBc chimers that lack one or both of a C-terminal or N-terminal cysteine residue, while being substantially free of nucleic acids.

Still further benefits and advantages will be apparent to the worker of ordinary skill from the disclosure that follows.

BRIEF DESCRIPTION OF THE DRAWINGS

In the drawings forming a portion of this disclosure
FIG. 1, shown in two panels as FIG. 1A and FIG. 1B, provides an alignment of six published sequences for mammalian HBc proteins from six viruses. The first (SEQ ID NO:1), human viral sequence is of the ayw subtype and was published in Galibert et al. (1983) *Nature*, 281:646-650; the second human viral sequence (SEQ ID NO:2), of the adw subtype, was published by Ono et al. (1983) *Nucleic Acids Res.*, 11(6): 1747-1757; the third human viral sequence (SEQ ID NO:3), is of the adw2 subtype and was published by Valenzuela et al., *Animal Virus Genetics*, Field et al. eds., Academic Press, New York (1980) pages 57-70; the fourth human viral sequence (SEQ ID NO:4), is of the adyw subtype that was published by Pasek et al. (1979) *Nature*, 282:575-579; the fifth sequence (SEQ ID NO:5), is that of the woodchuck virus that was published by Galibert et al. (1982) *J. Virol.*, 41:51-65; and the sixth mammalian sequence, (SEQ ID NO:6), is that of the ground squirrel that was published by Seeger et al. (1984) *J. Virol.*, 51:367-375.

FIG. 2 shows the modifications made to commercial plasmid vector pKK223-3 in the preparation of plasmid vector pKK223-3N used herein for preparation of recombinant HBc chimers. The modified sequence (SEQ ID NO:7) is shown below the sequence of the commercially available vector (SEQ ID NO:8). The bases of the added NcoI site are shown in lower case letters and the added bases are shown with double underlines, whereas the deleted bases are shown as dashes. The two restriction sites present in this segment of the sequence (NcoI and HindIII) are indicated.

FIG. 11, taken from PCT/US01/25625 (ICC-102.2) illustrates a reaction scheme (Scheme 1) that shows two reaction sequences for (I) forming an activated carrier for pendently linking a hapten to a chimeric hepatitis B core protein (sm-HBc) particle using sulpho-succinimidyl 4-(N-maleimidomethyl)-cyclohexane 1-carboxylate (sulpho-SMCC), and then (II) linking a sulfhydryl-terminated (cysteine-terminated) hapten to the activated carrier to form a conjugate particle. The sm-HBc particle is depicted as a box having a single pendent amino group (for purposes of clarity of the figure), whereas the sulfhydryl-terminated hapten is depicted as a line terminated with an SH group.

DEFINITIONS

Figure 3:
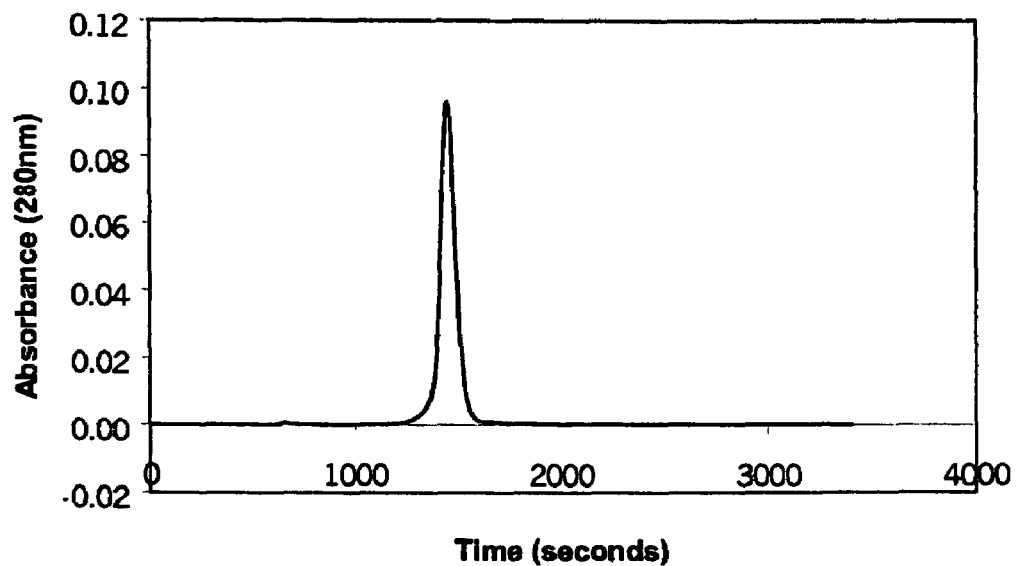
FIG. 3 is an analytical size exclusion chromatography elution profile for ICC-1603 particles in which absorbance at 280 nm is shown on the ordinate and time in seconds is shown on the abscissa.

Numerals utilized in conjunction with HBc chimers indicate the position in the HBc ayw amino acid residue sequence of SEQ ID NO:1 at which one or more residues has been added to or deleted from the sequence, regardless of whether additions or deletions to the amino acid residue sequence are present. Thus, HBc149 indicates that the chimer ends at residue 149, whereas HBc149+C150 indicates that that same chimer contains a cysteine residue at HBc position 150 relative to the sequence numbers of SEQ ID NO:1.

The term "antibody" refers to a molecule that is a member of a family of glycosylated proteins called immunoglobulins, which can specifically bind to an antigen.

The word "antigen" has been used historically to designate an entity that is bound by an antibody or receptor, and also to designate the entity that induces the production of the antibody. More current usage limits the meaning of antigen to that entity bound by an antibody or receptor, whereas the word "immunogen" is used for the entity that induces antibody production or binds to the receptor. Where an entity discussed herein is both immunogenic and antigenic, reference to it as either an immunogen or antigen is typically made according to its intended utility.

"Antigenic determinant" refers to the actual structural portion of the antigen that is immunologically bound by an antibody combining site or T-cell receptor. The term is also used interchangeably with "epitope". An antigenic determinant is thus a structure that stimulates antibody production or T cell activation, and the presence of such a structure can be ascertained by determining which structure is bound by antibodies or induces T cell activation.

The word "conjugate" as used herein refers to a hapten operatively linked to a carrier protein, as through an amino acid residue side chain.

The term "conservative substitution" as used herein denotes that one amino acid residue has been replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like.

The term "corresponds" in its various grammatical forms as used in relation to peptide sequences means the peptide sequence described plus or minus up to three amino acid residues at either or both of the amino- and carboxy-termini and containing only conservative substitutions in particular amino acid residues along the polypeptide sequence.

The term "Domain" is used herein to mean a portion of a recombinant HBc chimer molecule that is identified by (i) residue position numbering relative to the position numbers of HBcAg subtype ayw as reported by Galibert et al., (1979) *Nature*, 281:646-650 (SEQ ID NO: 1). The polypeptide portions of at least chimer Domains I, II and III are believed to exist in a similar tertiary form to the corresponding sequences of naturally occurring HBcAg.

As used herein, the term "fusion protein" designates a polypeptide that contains at least two amino acid residue sequences not normally found linked together in nature that are operatively linked together end-to-end (head-to-tail) by a peptide bond between their respective carboxy- and amino-terminal amino acid residues. The fusion proteins of the present invention are HBc chimer molecules that induce the production of antibodies that immunoreact with a polypeptide that corresponds in amino acid residue sequence to the polypeptide portion of the fusion protein.

The phrase "hepatitis B" as used here refers in its broadest context to any member of the family of mammalian hepadnaviridae, as discussed before.

The words "polypeptide" and "peptide" are used interchangeably throughout the specification and designate a linear series of amino acid residues connected one to the other by peptide bonds between the alpha-amino and carboxy groups of adjacent amino acids. Polypeptides can be a variety of lengths, either in their neutral (uncharged) forms or in forms that are salts. It is well understood in the art that amino acid residue sequences contain acidic and basic groups, and that the particular ionization state exhibited by the peptide is dependent on the pH value of the surrounding medium when the peptide is in solution, or that of the medium from which it was obtained if the peptide is in solid form. Thus, "polypeptide" or its equivalent terms is intended to include the appropriate amino acid residue sequence referenced. A peptide or polypeptide is always shown herein from left to right and in the direction from amino-terminus (N-terminus) to carboxy-terminus (C-terminus).

The term "residue" is used interchangeably with the phrase amino acid residue. All amino acid residues identified herein are in the natural or L-configuration. In keeping with standard polypeptide nomenclature, [*J. Biol. Chem.*, 243, 3557-59 (1969)], abbreviations for amino acid residues are as shown in the following Table of Correspondence.

TABLE OF CORRESPONDENCE

| 1-Letter | 3-Letter | AMINO ACID |
|---|---|---|
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| Z | Glx | L-glutamic acid or L-glutamine |
| W | Trp | L-tryptophan |
| R | Arg | L-arginine |
| D | Asp | L-aspartic acid |
| N | Asn | L-asparagine |
| B | Asx | L-aspartic acid or L-asparagine |
| C | Cys | L-cysteine |

Numerals utilized in conjunction with HBc chimers indicate the position in the HBc ayw amino acid residue sequence of SEQ ID NO:1 at which one or more residues has been added to or deleted from the sequence, regardless of whether additions or deletions to the amino acid residue sequence are present. Thus, HBc149 indicates that the chimer ends at residue 149, whereas HBc149+C150 indicates that that same chimer contains a cysteine residue at HBc position 150 relative to the sequence numbers of SEQ ID NO:1.

DETAILED DESCRIPTION OF THE INVENTION

The present invention contemplates a method for treating chronic hepatitis B infection. A contemplated method utilizes a vaccine comprising a chimeric recombinant hepadnavirus nucleocapsid protein; i.e., a hepatitis B core (HBc) chimeric protein molecule that self-assembles into particles after expression in a host cell. A contemplated chimer molecule is truncated at least at the C-terminus relative to a native core molecule whose C-terminus is normally at residue position 183 for the ayw subtype of FIG. 1. Particles containing a contemplated chimer molecule are stabilized by a cysteine residue that is located at or near one or both of the C- and N-termini, and are preferably substantially free of binding to nucleic acids as is discussed hereinafter.

A contemplated chimer molecule contains at least about 125, and more preferably at least about 135, to all of the N-terminal 165 amino acid residues of HBc and can include one or more other amino acid residue sequences that are typically B or T cell epitopes of HBV, another pathogen or another protein such as bovine inhibin. Examples of B cell and T cell epitopes from non-HBV proteins that can be incorporated in the chimer molecule are illustrated hereinafter in Tables A and B. An example of a T-cell epitope that is derived from the hepatitis B virus that is preferably incorporated in the chimer molecule is the surface antigen Pre-S2 sequence 144-160. An example of a B-cell epitope that is derived from the hepatitis B virus that is preferably incorporated in the chimer molecule is the surface antigen Pre-S2 sequence 130-144.

A contemplated method of treating chronic hepatitis comprises the steps of administering an anti-HBc T cell-stimulating amount of a vaccine comprised of immunogenic particles dissolved or dispersed in a pharmaceutically acceptable diluent to a patient having a chronic hepatitis B virus infection. The immunogenic particles are preferably administered in conjunction with an adjuvant.

Preferred adjuvants used herein are molecules that interact with toll-like receptors. Most preferred adjuvants are lipid-A analogues such as monophosphoryl lipid A and aminoalkyl glucosamide phosphates. Other preferred adjuvants include saponins and chemically modified alkylated saponins. The adjuvants can further comprise microparticulate carriers such as oil-in water emulsions or mineral salts.

The immunogenic particles are comprise recombinant hepatitis B core (HBc) chimeric protein molecules, with the chimeric protein molecules being up to about 550 amino acid residues in length. Those chimeric protein molecules (a) contain an HBc sequence of about 125 up to all of the N-terminal 165 amino acid residues of the HBc molecule that contains the HBC sequence of residue positions 4 through about 75 and about 85 through about 140.

The HBC chimer molecule sequence optionally includes (a') a peptide-bonded amino acid sequence containing an immunogenic epitope at one or more of the N-terminus, in the HBc immunodominant loop (i.e., between residue positions 76 through 85) and the C-terminus of the chimer, or (b') an insert in the HBc immunodominant loop having a length of one to about 40 amino acid residues that includes a chemically non-reactive residue or a chemically-reactive linker residue for a conjugated hapten, or (c') zero to all of the residues of the sequence of positions 76 through 85.

The chimeric protein molecule also contains one or both of (a') one to three cysteine residues at an amino acid position of the chimer molecule corresponding to amino acid position −20 to about +1 from the N-terminus of the HBc sequence of SEQ ID NO:1 [N-terminal cysteine residue(s)] in a sequence other than that of the HBc precore sequence and (b') one to about three cysteine residues toward the C-terminus of the molecule from the C-terminal residue of the HBc sequence and within about 30 residues from the C-terminus of the chimer molecule [C-terminal cysteine residue(s)].

A chimeric protein molecule contains no more than 20 percent conservatively substituted amino acid residues in the HBc sequence, and self-assembles into particles on expression in a host cell. In one aspect of the invention, the particles are substantially free of binding to nucleic acids and exhibit a ratio of absorbance ratio at 280 nm to 260 nm of about 1.2 to about 1.7, whereas in other aspects, more than minimal nucleic acid binding is present and the particles exhibit an absorbance ratio at 280 nm to 260 nm of about 0.9 to about 1.15. Broadly, therefore, the absorbance ratio at 280 nm to 260 nm of contemplated particles can be about 0.9 to about 1.7. Nucleic acid binding is discussed hereinafter. The particles are more stable than are particles formed from otherwise identical HBc chimer molecules that are free of any above-mentioned C-terminal cysteine residue (s) or N-terminal cysteine residue(s) or (ii) in which a C-terminal or an N-terminal cysteine residue(s) present in a contemplated chimer molecule is (are) replaced by another residue.

The patient to whom the vaccine is administered is maintained for a time sufficient to induce T cells activated against HBc. In other embodiments, the method is carried out on patients that have HBsAg circulating in their blood stream and the patient is maintained for a time period sufficient to diminish the amount to circulating HBsAg. In a further aspect of the invention, the patient's serum contains HBeAg, and the treatment results in decreasing the amount of the HBeAg antigen in the patient's serum. Those skilled in the art are well aware of known methods for assaying for each of T cell activation against HBc/HbeAg and HBsAg.

The chimeric protein can display one or more immunogenic epitopes at the N-terminus, in the HBc immunogenic (immunodominant) loop or C-terminus, or a non-reactive (heterologous) residue or a linker residue for a B cell or T cell epitope in the immunogenic loop, or has zero to all of the residues of positions 76 through 85. In one embodiment, the chimeric protein contains one or more N-terminal cysteine residue(s) that confers enhanced stability on formation to the self-assembled particles.

In another embodiment, the chimeric protein contains one or more C-terminal cysteine residue(s) that confers enhanced stability on formation to the self-assembled particles. A contemplated chimeric protein molecule can also contain a cysteine residue at or near both of the N- and C-termini, that is a chimeric protein molecule can contain both an N-terminal cysteine residue and a C-terminal cysteine residue, as defined previously.

In some preferred embodiments, a contemplated chimeric protein is sufficiently free of arginine and or lysine residues downstream of (toward the carboxy-terminus from) HBc residue position 149 so that the self-assembled particles are substantially free of nucleic acid binding. In other embodiments, the HBc sequence from position 149 through about position 163 that includes two of the arginine-rich repeat sequences is present (See, FIG. 1). In other embodiments, the HBc sequence through about position 156 that contains one arginine-rich sequence is present. In still other embodiments, the C-terminal HBc sequence ends between HBc positions 140 and 149 and the chimer molecule is free of the arginine repeats present in a native HBc sequence of FIG. 1 from position 150 through the C-terminus or a similar sequence containing lysine residues in place of one or more of the arginine residues. Substantial freedom from nucleic acid binding is discussed hereinafter and is readily determined.

For ease of discussion, contemplated chimer sequences and sequence position numbers referred to herein are based on the sequence and position numbering of the human hepatitis B core protein of subtype ayw [Galibert et al., (1979) Nature, 281:646-650] that is shown in SEQ ID NO: 1. It is to be understood, however, that in view of the great similarity between the mammalian hepadnavirus capsid protein sequences and similar particle formation exhibited by those proteins, which are well-known to skilled workers, a discussion regarding human HBc subtype ayw is also applicable to subtype adw, as well as the woodchuck and ground squirrel proteins. As a consequence of those great similarities, HBc sequences are recited generally herein as a "HBc" sequence, unless otherwise stated.

In one embodiment, a contemplated HBc chimer is up to about 550 residues in length and contains (a) an HBc sequence of about 125 to all of the N-terminal 165 amino acid residues of the HBc molecule that includes the HBc sequence of residue positions 5 through about 75 and about 85 through about 140, (a') a peptide-bonded immunogenic epitope at one or more of the N-terminus, in the HBc immunodominant loop or the C-terminus of the chimer, or (b') an insert in the HBc immunodominant loop having a length of one to about 40 amino acid residues and containing a chemically non-reactive residue or a chemically reactive linker residue for a conjugated hapten, or (c') zero to all of the residues of the sequence of positions 76 through 85.

The chimeric protein molecule also contains one or both of (a') one to three cysteine residues at an amino acid position of the chimer molecule corresponding to amino acid position −20 to about +1 from the N-terminus of the HBc sequence of SEQ ID NO: 1 [N-terminal cysteine residue(s)] in a sequence other than that of the HBc precore sequence and (b') one to about three cysteine residues toward the C-terminus of the molecule from the C-terminal residue of the HBc sequence and within about 30 residues from the C-terminus of the chimer molecule [C-terminal cysteine residue(s)].

That chimer molecule contains no more than about 20 percent conservatively substituted amino acid residues in the HBc sequence, and self-assembles into particles on expression in a host cell. The particles are more stable on formation than are particles (i) formed from otherwise identical HBc chimer molecules that are free of any above-mentioned N-terminal or C-terminal cysteine residue(s) or (ii) in which an N-terminal or C-terminal cysteine residue(s) present in a contemplated chimer molecule is (are) replaced by another residue. As already noted, the particles are substantially free of binding to nucleic acids in some embodiments and bind non-minimal amounts of nucleic acids in other embodiments.

The patient is maintained for a time period sufficient to induce T cells activated against HBc. In other embodiments the patient is first treated with an antiviral drug such as lamivudine for a time sufficient to reduce viral burden, and then the patient receives one or more administrations of the contemplated chimer molecule administered in an acceptable excipient optionally with an adjuvant. In further embodiments, the method is carried out on patients that have HBsAg circulating in their blood stream and the patient is maintained for a time period sufficient to diminish the amount to circulating HBsAg. In a further aspect of the invention, the patient's serum contains HBeAg, and the treatment results in decreasing the amount of the HBeAg antigen in the patient's serum.

A contemplated chimer molecule contains at least one cysteine residue that is located at either or both of (i) at a position of about −20 to about +1 relative to the N-terminus of HBc as is illustrated in FIG. 1 and SEQ ID NO: 1 or (ii) toward the C-terminus of the molecule from the C-terminal residue of the HBc sequence and within about 30 residues from the C-terminus of the chimer molecule. The concept of a negative amino acid position is usually associated with a leader sequence such as the precore sequence of HBc. That concept is used similarly here in that one can simply align a given chimer molecule sequence with that of SEQ ID NO: 1 to determine the position of the chimer that corresponds to that of the starting methionine residue of position +1 of HBc.

Inasmuch as amino acid residue sequences are normally shown from left to right and in the direction from N-terminus to C-terminus, any aligned chimer molecule residue to the left of the position that can be occupied by the HBc start methionine has a negative position. A contemplated cysteine residue can occur at a position about twenty residues to the left of the aligned start methionine of HBc to the position corresponding to that start methionine.

In one aspect, a preferred HBc chimer has a sequence of about 135 to about 525 L-α-amino acid residues and contains four serially peptide-linked domains; i.e., Domains I, II, III and IV. Those four domains are linked together in the same manner as are native proteins; i.e., they are peptide-bonded to each other, as compared to polypeptides that contain residues of other than α-amino acids and therefore cannot form peptide bonds, those that contain D-amino acid residues, or oligopeptide conjugates in which two or more polypeptides are operatively linked through an amino acid residue side chain. A contemplated chimeric HBc protein can therefore be prepared by expression using the usual methods of recombinant technology.

Domain I of that chimer molecule comprises about 71 to about 110 amino acid residues whose sequence includes (i) at least the sequence of the residues of position 5 through position 75 of HBc, (ii) one to three cysteine residues at an amino acid position of the chimer molecule corresponding to amino acid position −20 to about +1, and preferably amino acid position −14 to about +1, from the N-terminus of the HBc sequence of SEQ ID NO: 1 [N-terminal cysteine residue(s)] in a sequence other than that of the HBc precore sequence, and (iii) an optional sequence containing up to about 30 amino acid residues peptide-bonded to one of HBc residues 2-4 that comprise an immunogenic epitope. That immunogenic sequence, when present, is typically an epitope used to induce an anti-hepatitis B immune response.

Domain II of that chimer molecule comprises up to about 255 amino acid residues peptide-bonded to HBc residue 75 of Domain I in which (i) zero to all residues in the sequence of HBc positions 76 through 85 are present peptide-bonded to (ii) an optionally present sequence of one to about 245 amino acid residues that constitute an immunogenic epitope, or (iii) an insert in the HBc immunodominant loop having a length of one to about 40 amino acid residues that contains a chemically non-reactive residue or a chemically-reactive linker residue for a conjugated hapten. It is particularly preferred that the sequence of 10 residues of positions 76 trough 85 (position 76-85 sequence) be present, but interrupted by one to about 245 residues of the epitope- or linker-containing sequence.

Domain III is an HBc sequence from position 86 through position 135 peptide-bonded to residue 85 of Domain II.

Chimer molecule Domain IV comprises (i) five through fourteen residues of an HBc amino acid residue sequence from position 136 through 149 peptide-bonded to the residue of position 135 of Domain III, (ii) zero to three cysteine residues [C-terminal cysteine residue(s)] within about 30 residues from the C-terminus of the chimer molecule, and (iii) zero to about 100 amino acid residues in an immunogenic sequence not present in HBc from position 150 to the C-terminus. Preferably, Domain IV contains a sequence of zero to about 50 amino acid residues in a sequence absent from those positions of HBc, and more preferably that sequence is zero to about 25 residues. Domain IV also preferably contains one C-terminal cysteine residue.

The chimer molecules (i) have an amino acid residue sequence in which no more than about 10 percent of the amino acid residues are substituted in the HBc sequence of the chimer and (ii) self-assemble into particles on expression in a host cell. The particles are substantially free of binding to nucleic acids and are more stable than are particles formed from otherwise identical HBc chimer molecules that are free of any above-mentioned C-terminal cysteine residue(s) and (i) lack the N-terminal cysteine residue(s) or (ii) in which an N-terminal cysteine residue(s) present in a contemplated chimer molecule is (are) replaced by another residue.

In one aspect, a contemplated chimer molecule contains a sequence comprising an epitope at the N-terminus peptide-bonded to one of HBc residues 2-5. In another aspect, a contemplated chimer molecule contains an epitope- or a linker residue-containing sequence peptide-bonded near the middle of the molecule located between HBc residues 76 and 85 in the immunodominant loop. In a further aspect, an epitope-containing sequence is located at the C-terminal portion of the chimer molecule peptide-bonded to one of HBc residues 136-149. In yet other aspects, two or three epitope-containing sequences are present at the above locations, or one or two epitope-containing sequences are present along with a linker residue for an epitope. Each of those chimer molecules also contains one or both of an N-terminal or C-terminal cysteine residue(s), as discussed before. Specific examples of several of these chimer molecules and their self-assembled particles are discussed hereinafter.

As already noted, a contemplated HBc chimer molecule of this aspect contains about 135 to about 525 amino acid residues. In some preferred embodiments, HBc residue 4 is present, whereas residues 2-5 are present in other preferred embodiments, so that Domain I can begin at HBc residue 4 or 2 and continue through residue 75; i.e., the HBc residue at HBc position 75. Residue 1 is methionine, the amino acid of the DNA start codon. It is preferred that the native methionine that is normally present at position 1 of HBc be absent so that only one start signal is present in the encoding DNA or NA.

The heterologous immunogenic epitope that can be present in Domain I or in the immunodominant loop of Domain II preferably contains about 15 to about 50 residues, although an insert as short as about 6 amino acid residues can induce and be recognized by antibodies and T cell receptors and is therefore useful.

In another embodiment of the invention, one or more chemically non-reactive (heterologous) amino acid residues is inserted in Domain II not to function as a B-epitope but to reduce the recognition of the chimeric particle by antibodies circulating in the blood of patients infected with hepatitis B virus. In a preferred aspect of the invention the chimeric molecule contains a single amino acid insertion at residue position 76, 77, 78, 79, 80, 81 or 82, and most preferably at residue position 77. That inserted chemically non-reactive residue can be an alanine, leucine or isoleucine, and is most preferably an alanine residue. It can be desirable to render the particle less antigenic than the native HBc particle; i.e., recognized less well by anti-HBc antibodies resulting from HBV infection. One skilled in the art can use any number of amino acid residues and sequences inserted into Domain II to reduce the antigenicity.

It is preferred that all of the residues of Domain II from position 76 through position 85 are present, although interrupted by one or more other residues. Domain II must contain at least four residues, that can have any sequence that does not interfere with expression or use, but those residues are preferably part of the sequence between the residues of positions 75 and 85.

Domain III contains HBc residues 86 through 135 peptide-bonded to residue 85.

Domain IV contains a sequence of at least five residues that are comprised of (i) a sequence of the residues of HBc positions 136 through 140, and preferably through 149, peptide-bonded to residue 135, (ii) zero to three cysteines residues and (iii) optionally can contain a sequence of an immunogenic epitope of up to about 100 residues, particularly when the HBc sequence ends at residue 140, although a shorter sequence of up to about 25 residues is more preferred. That Domain IV immunogenic sequence is preferably heterologous to the sequence of HBc and is other than a sequence of HBc from about position 165 to the HBc C-terminus. The immunogenic sequence, when present in Domain IV, is preferably a T cell epitope, but can also be a B cell epitope as are usually present in one or the other of Domains I and II. Illustrative T cell epitopes from the HBc sequence and from the preS1 and preS2 regions of hepatitis B surface protein (HBs or HBsAg) are provided in Tables A and B, hereinafter.

Domain IV can also contain zero to three cysteine residues and those Cys residues are present within about 30 residues of the carboxy-terminus (C-terminus) of the chimer molecule. Preferably, one cysteine (Cys) residue is present, and that Cys is preferably present as the carboxy-terminal (C-terminal) residue, unless a T cell epitope is present as part of Domain IV. When such a T cell epitope is present, the preferred Cys is preferably within the C-terminal last five residues of the HBc chimer.

In one embodiment, a particularly preferred chimer contains two immunogenic epitopes. Those two immunogenic epitopes are present in Domains I and II, or II and IV, or I and IV. One of the two immunogenic epitopes is preferably a B cell epitope in some embodiments. In other embodiments, one of the two immunogenic epitopes is a T cell epitope. More preferably, both of the two immunogenic epitopes are the same or different T cell epitopes. In addition, a plurality of B cell epitopes can be present at a B cell epitope location, as can a plurality of T cell epitopes be present at a T cell epitope location.

In the embodiments in which the chimer molecule contains an immunogenic epitope in Domain II, it is preferred that that the sequence contain one or more B cell epitopes, that the HBc sequence between amino acid residues 76 and 85 be present, but interrupted by the immunogenic epitope(s), and that the chimer further include one or more T cell epitopes in Domain IV peptide-bonded to one of HBc residues 140-165.

This same preference holds for those chimer molecules in which the heterologous linker residue for a conjugated epitope is present in Domain II, thereby providing one or more immunogenic epitopes in Domain II, with residues 76 and 85 present, but interrupted by the heterologous linker residue, with a T cell epitope being present peptide-bonded to one of HBC residues 140-165. The particles formed from such chimer molecules typically contain a ratio of conjugated epitope to C-terminal peptide-bonded T cell epitope of about 1:4 to 1:1, with a ratio of about 1:2 being common.

In an illustrative structure of an above-described chimer molecule, a heterologous linker residue for a conjugated epitope is present in Domain II and a T cell epitope is present in Domain IV, with no additional B cell epitope being present in Domain II. Such a chimer exhibits immunogenicity of the T cell epitope, while exhibiting minimal, HBc antigenicity as measured by binding of anti-loop monoclonal antibodies in an ELISA assay as discussed hereinafter.

A preferred contemplated HBc chimer molecule contains a sequence of about 135 to about 525 residues. A preferred HBc chimer molecule that can contain one or two immunogenic epitopes of preferred lengths of about 15 to about 50 residues each and a preferred HBc portion length of about 140 to about 165 residues has a sequence length of about 170 to about 250 amino acid residues. Particularly preferred chimer molecules that contain one or two immunogenic epitopes have a length of about 190 to about 210 residues. A particularly preferred chimer molecule that is free of added immunogenic epitopes can have a length of about 140 to about 165 residues. It is to be understood that a wide range of chimer molecule lengths is contemplated in view of the variations in length of the N- and C-terminal HBc portions and differing lengths of the several contemplated epitopes that can be inserted in the immunogenic loop.

A contemplated recombinant protein, after expression in a host cell, self-assembles to form particles that are substantially free of binding to nucleic acids. The contemplated HBc chimer particles are generally spherical in shape and are usually homogeneous in size for a given preparation. These chimeric particles thus resemble native HBc particles that have a similar shape and size and can be recovered from infected persons.

A contemplated chimer particle comprises previously discussed chimer molecules. More broadly, such a chimer particle comprises a chimeric C-terminal truncated HBc protein that has a sequence of at least about 125 of the N-terminal 165 residues and contains (i) an immunogenic epitope peptide-bonded to one or more of the N-terminus, C-terminus or the immunodominant loop, or a heterologous non-reactive or linker residue for an epitope in the immunodominant loop, and (ii) one or both of one to three N-terminal cysteine residues and one to three C-terminal cysteine residues as previously described, and at least a 5 HBc residue sequence from position 135.

A contemplated particle is sufficiently free of arginine and/or lysine residues in Domain IV so that the self-assembled particles are substantially free of nucleic acid binding and exhibit a 280:260 absorbance ratio of about 1.2 to about 1.7, as discussed hereinafter. Thus, a contemplated chimeric protein is free of the HBc sequence between positions about 155 and 183, and is more preferably free of a HBc sequence between positions about 155 and 183.

The presence of the above-discussed N-terminal cysteine residue(s) provides an unexpected enhancement of the ability of the chimer molecules to form stable immunogenic particles (discussed hereinafter). Thus, a contemplated HBc chimer particle immunogen tends to form particles that stay together upon collection and initial purification as measured by analytical size exclusion chromatography, whose details are discussed hereinafter.

Contemplated particles are more stable upon formation than are particles formed from otherwise identical HBc chimer molecules that (i) lack the N-terminal cysteine residue(s) or (ii) in which an N-terminal cysteine residue(s) present in a contemplated chimer molecule is (are) replaced by another residue and are also are free of any above-mentioned C-terminal cysteine residue(s). In some instances, particles do not form unless an N-terminal cysteine is present. Examples of enhanced stabilities for both types of sequences are illustrated in the Examples that follow.

A contemplated particle containing an N-terminal cysteine residue is also typically prepared in greater yield than is a particle assembled from a chimer molecule lacking a N-terminal cysteine. This increase in yield can be seen from the mass of particles obtained or from analytical gel filtration analysis using Superose® 6 HR as discussed hereinafter.

The substantial freedom of nucleic acid binding exhibited by contemplated particles can be readily determined by a comparison of the absorbance of the particles in aqueous solution measured at both 280 and 260 nm; i.e., a 280:260 absorbance ratio. The contemplated particles do not bind substantially to nucleic acids that are oligomeric and/or polymeric DNA and RNA species originally present in the cells of the organism used to express the protein. Such nucleic acids exhibit an absorbance at 260 nm and relatively less absorbance at 280 nm, whereas a protein such as a contemplated chimer absorbs relatively less at 260 nm and has a greater absorbance at 280 nm.

Thus, recombinantly expressed HBc particles or chimeric HBc particles that contain the arginine-and lysine-rich sequence at residue positions 150-183 (or 150-185) sometimes referred to in the art as the protamine region exhibit a ratio of absorbance at 280 nm to absorbance at 260 nm (280:260 absorbance ratio) of about 0.8. On the other hand, particles sufficiently free of arginine and lysine residues in Domain IV so that the self-assembled particles are substantially free of nucleic acid binding such as particles that are free of the arginine-rich nucleic acid binding region of naturally occurring HBc like those that contain fewer than about ten, preferably fewer than about 6, and more preferably fewer than three arginine or lysine residues or mixtures thereof adjacent to each other. Illustrative proteins have a native or chimeric sequence that ends at about HBc residue position 165, preferably at about 155 and more preferably at about position 140 to position 149, exhibit a 280:260 absorbance ratio of about 0.9 to about 1.7. A more typical 280:260 absorbance ratio is about 0.9 to about 1.0 for a sequence ending at about position 165, about 1.1 to about 1.2 for a sequence ending at about position 155, and about 1.4 to about 1.7 for a sequence ending at about position 140 to about 149. This range is due in large part to the number of aromatic amino acid residues present in Domains II and IV of a given chimeric HBc particle.

Domain I of a contemplated chimeric HBc protein constitutes an amino acid residue sequence of HBc beginning with at least amino acid residue position 5 through position 75, and Domain III constitutes a HBc sequence from position 86 through position 137. The sequences from any of the mammalian hepadnaviruses can be used for either of Domains I and III, and sequences from two or more viruses can be used in one chimer. Preferably, and for ease of construction, the human ayw sequence is used through out the chimer.

HBc chimers having a Domain I that contains more than a deletion of the first three amino-terminal (N-terminal) residues have been reported to result in the complete disappearance of HBc chimer protein in *E. coli* cells. Pumpens et al., (1995) *Intervirology*, 38:63-74. On the other hand, a recent study in which an immunogenic 23-mer polypeptide from the influenza M2 protein was fused to the HBc N-terminal sequence reported that the resultant fusion protein formed particles when residues 1-4 of the native HBc sequence were replaced. Neirynck et al. (October 1999) *Nature Med.*, 5(10):1157-1163. Thus, the art teaches that particles can form when an added amino acid sequence is peptide-bonded to one of residues 2-4 of HBc, whereas particles do not form if no additional sequence is present and more than residues 1-3 are deleted from the N-terminus of HBc.

An N-terminal epitope sequence peptide-bonded to one of the first five N-terminal residues of HBc can contain a single cysteine residue or a sequence of up to about 30 residues that comprise an immunogenic sequence. The one to three cysteine residues can be present at a convenient location in the sequence, but are typically near the C-terminus of the added sequence so that the added N-terminal cysteine residue(s) are at a position of about −20 to about +1, and more preferably at a position of about −14 to about +1, relative to the HBc N-terminus as shown in SEQ ID NO: 1. Exemplary sequences include a B cell or T cell epitope such as those discussed and illustrated hereinafter (Tables A and B, respectively), the 23-mer polypeptide from the influenza M2 protein of Neirynck et al., above, that includes two cysteine residues, and variants of that sequence containing at least about 6 residues, a sequence of another (heterologous) protein such as β-galactosidase as can occur in fusion proteins as a result of the expression system used, or another hepatitis B-related sequence such as that from the PreS1 or PreS2 regions or the major HbsAg immunogenic sequence.

Domain II is a sequence of about 5 to about 250 amino acid residues. Of those residues, zero (none), and preferably at least 4 residues, and more preferably at least 8, constitute portions of the HBc sequence at positions 76 through 85, and one to about 245 residues, and preferably one to about 50 residues are heterologous (foreign) to HBc or correspond to an immunogenic HBc sequence such as a B or T cell epitope.

Thus, at least HBc residues 75 and 85 are present in Domains I and II, respectively. Those residues constitute (i) a heterologous linker residue for a epitope such as a B cell or T cell epitope or (ii) an immunogenic B or T cell epitope that preferably contains 6 to about 50, more preferably about 15 to about 50, and most preferably about 20 to about 30 amino acid residues, and are positioned so that they are peptide-bonded between zero, or preferably at least 4 and more preferably at least 8 residues, or all of the residues of positions 76 through 85 of the HBc sequence. Immunogenic B cell epitopes are preferably linked at this position by the linker residue or are peptide-bonded into the HBc sequence, and use of a B cell epitope is discussed illustratively hereinafter.

Those preferred at least 4 HBc residues can be all in one sequence such as residues 82-85, or can be split on either side of (flank) the heterologous linker residue(s) as where residues 76-77 and 84-85 are present or where residues 76 and 83-85 are present. More preferably, Domain II contains at least 8 residues of the HBc sequence from residue 76 to 85. Most preferably, the sequence of all 10 residues of positions 76 through 85 is present in the chimer.

The one to about 245 residues added to the HBc loop sequence can be heterologous to a HBc sequence or can correspond to one or more immunogenic portions of the HBc sequence. A single added heterologous residue is a heterologous linker residue for a B cell epitope as discussed before. The longer sequences, typically at least 6 amino acid residues long to about 50 amino acid residues long and more preferably about 15 to about 50 residues in length, as noted before, are in a sequence that comprises an immunogen such as a B cell or T cell epitope, except for heterologous residues encoded by restriction sites.

Exemplary peptide B cell epitopes useful for both linkage to the linker residue after expression of a contemplated chimer and for expression within a HBc chimer at one or more of the N-terminus, within the immunogenic loop or at the C-terminus of the chimer are illustrated in Table A, below, along with the common name given to the gene from which the sequence is obtained, the literature or patent citation for published epitopes, and SEQ ID NO.

TABLE A

B Cell Epitopes

| Organism | Gene | Sequence | Citation* | SEQ ID NO |
|---|---|---|---|---|
| *Streptococcus pneumoniae* | PspA1 | KLEELSDKIDELDAE | 1 | 9 |
| | PsP2 | QKKYDEDQKKTEE-KAALEKAASEEM-DKAVAAVQQA | 1 | 10 |
| *Cryptosporidium parvum* | P23 | QDKPADAPAAEAPA-AEPAAQQDKPADA | 2 | 11 |
| HIV | GP120 | RKRIHIGPGR-AFYITKN | 3 | 12 |
| Foot-and-mouth virus | VP1 | YNGECRYNRNA-VPNLRGDLQVL-AQKVARTLP | 4 | 13 |
| Influenza Virus A8/PR8 | HA | YRNLLWLTEK | 8 | 14 |
| Type A (A8/PR8/34) | M2 | SLLTEVETPIR-NEWGCRCNGSSD | 29 | 15 |
| | | SLLTEVETPIR-NEWGCRCNDSSD | 29 | 16 |
| | | SLLTEVETPIR-NEWGARANDSSD | | 17 |
| | | EQQSAVDADDS-HFVSIELE | 35 | 18 |
| | | SLLTEVETPIR-NEWGSRSNDSSD | | 19 |
| | | SLLTEVETPIR-NEWGSRCNDSSD | | 20 |
| | | SLLTEVETPIR-NEWGCRSNDSSD | | 21 |
| | | SLLTEVETPIR-NEWGCRANDSSD | | 22 |

TABLE A-continued

B Cell Epitopes

| Organism | Gene | Sequence | Citation* | SEQ ID NO |
|---|---|---|---|---|
| | | SLLTEVETPIR-NEWGARCNDSSD | | 23 |
| | | MSLLTEVETPIR-NEWGCRCNDSSD | | 24 |
| | | MSLLTEVETPIR-NEWGSRSNDSSD | | 25 |
| | | MGISLLTEVETPIR-NEWGCRCNDSSD-ELLGWLWGI | | 26 |
| | | MSLLTEVETPIR-NEWGARANDSSD | | 27 |
| | | MSLLTEVETPIR-NEWGCRANDSSD | | 28 |
| | | MSLLTEVETPIR-NEWGARCNDSSD | | 29 |
| | | MSLLTEVETPIR-NEWGCRSNDSSD | | 30 |
| | | MSLLTEVETPIR-NEWGSRCNDSSD | | 31 |
| | | $X_1X_2X_3X_4X_5X_6X_7X_8T\text{-}X_{10}X_{11}RX_{13}X_{14}X_{15}X_{16}X_{17}X_{18\text{-}19}X_{20}X_{21}\text{-}X_{22}X_{23}X_{24}$ | | 32 |
| Type B | NB | NNATFNYTNVNPISHIR | | 33 |
| Yersinia pestis | V Ag | DILKVIVDSMNHH-GDARSKLREELAE-LTAELKIYSVIQA-EINKHLSSSGTIN-IHDKSINLMDKNL-YGYTDEEIFKASA-EYKILEKMPQTTI-QVDGSEKKIVSIK-DFLGSENKRTGAL-GNLKNSYSYNKDN-NELSHFATTCSD | 9 | 34 |
| Haemophilus influenza | pBOMP | CSSSNNDAA-GNGAAQFGGY | 10 | 35 |
| | | NKLGTVSYGEE | | 36 |

TABLE A-continued

B Cell Epitopes

| Organism | Gene | Sequence | Citation* | SEQ ID NO |
|---|---|---|---|---|
| | | NDEAAYSKNRPAVLAY | | 37 |
| Moraxella catarrhalis | copB | LDIEKDKKKRTDEQLQAELDDKYAGKGY | 11 | 38 |
| | | LDIEKNKKKRTEAELQAELDDKYAGKGY | | 39 |
| | | IDIEKKGKIRTEAELLAELNKDYPGQGY | | 40 |
| Porphyromonas gingivalis | HA | GVSPKVCKDVTVEGSNEFAPVQNLT | 12 | 41 |
| | | RIQSTWRQKTVDLPAGTKYV | | 42 |
| Trypanosoma cruzi | | KAAIAPAKAAAAPAKAATAPA | 14 | 43 |
| Plasmodium falciparum | CS | (NANP)$_4$ | 24 | 44 |
| | | NANPNVDP(NANP)$_3$NVDP | | 45 |
| | | NANPNVDP(NANP)$_3$ | | 46 |
| | | (NANP)$_3$NVDPNANP | | 47 |
| | | NANPNVDP(NANP)$_3$NVDPNANP | | 48 |
| | | NPNVDP(NANP)$_3$NV | | 49 |
| | | NPNVDP(NANP)$_3$NVDP | | 50 |
| | | NPNVDP(NANP)$_3$NVDPNA | | 51 |
| | | NVDP(NANP)$_3$NV | | 52 |
| | | NVDP(NANP)$_3$NVDP | | 53 |
| | | NVDP(NANP)$_3$NVDPNA | | 54 |
| | | DP(NANP)$_3$NV | | 55 |
| | | DP(NANP)$_3$NVDP | | 56 |
| | | DP(NANP)$_3$- | | 57 |

TABLE A-continued

B Cell Epitopes

| Organism | Gene | Sequence | Citation* | SEQ ID NO |
|---|---|---|---|---|
| | | NVDPNA | | |
| vivax | CS | GDRADGQPAG-DRADGQPAG | 20 | 58 |
| | | RADDRAAGQP-AGDGQPAG | | 59 |
| | | ANGAGNQPG-ANGAGDQPG | | 60 |
| | | ANGADNQPG-ANGADDQPG | 27 | 61 |
| | | ANGAGNQPG-ANGADNQPG | | 62 |
| | | ANGAGNQPG-ANGADDQPG | | 63 |
| | | APGANQEGGAA-APGANQEGGAA | 28 | 64 |
| | | ANGAGNQPGAN-GAGDQPGANGA-DNQPGANGADD-QPG | | 65 |
| berghi | CS | DPPPPNPN-DPPPPNPN | 2 | 66 |
| yoelli | CS | (QGPGAP)$_4$ | | 67 |
| Streptococcus sobrinus | AgI/II | KPRPIYEA-KLAQNQK | 16 | 68 |
| | | AKADYEAK-LAQYEKDL | | 69 |
| Shigella flexneri | Invasin | KDRTLIEQK | 18 | 70 |
| Respiratory syncitia virus (RSV) | G | CSICSNNPT-CWAICK | 19 | 71 |
| Entamoeba histolytica | lectin | VECASTVCQNDN-SCPIIADVEKCNQ | 21 | 72 |
| Schistosoma japonicum | para | DLQSEISLSLE-NGELIRRAKSA-ESLASELQRRVD | 22 | 73 |
| Schistosoma mansoni | para | DLQSEISLSLE-NSELIRRAKAA- | 22 | 74 |

TABLE A-continued

B Cell Epitopes

| Organism | Gene | Sequence | Citation* | SEQ ID NO |
|---|---|---|---|---|
| | | ESLASDLQRRVD | | |
| Bovine Inhibin | $\alpha_c$ subunit | STPPLPWPWSPAALRLLQRPPEEPAA | 30 | 75 |
| Ebola Virus | membrane-anchored glycoprotein | ATQVEQHHRRTDNDSTA | 31 | 76 |
| | | HNTPVYKLDISEATQVE | 31 | 77 |
| | | GKLGLITNTIAGVAVLI | 31 | 78 |
| Escherichia coli | ST | CCELCCYPACAGCN | 33 | 79 |
| | | NTFYCCELCCYPACAGCN | 33 | 80 |
| | | SSNYCCELCCYPACAGCN | 33 | 81 |
| Alzheimer's disease | β-Amyloid | DAEFRHDSGYEVHHQKLVFFAEDVGSNKGAIIGLMVGGVVIA | 34 | 82 |
| | | DAEFRHDSGYEVHHQKL | | 83 |
| | | EDVGSNKGAII | | 84 |
| | | DAEFRHDSGYEVHHQKLVFFAEDVGSNKGAIIG | | 85 |
| Neisseria meningitidis | PorA | YVAVENGVAKKVA | | 86 |
| | | HFVQQTPKSQPTLVP | | 87 |
| | | HVVVNNKVATHVP | | 88 |
| | | PLQNIQPQVTKR | | 89 |
| | | AQAANGGAASGQVKVTKVTKA | | 90 |
| | | YVDEQSKYHA | | 91 |
| | | HFVQNKQNQPPTLVP | | 92 |
| | | KPSSTNAKTGNKVEVTKA | | 93 |
| | | YWTTVNTGSATTTTFVP | | 94 |
| | | YVDEKKKMVHA | | 95 |
| | | HYTRQNNADVFVP | | 96 |
| | | YYTKDTNNNLTLVP | | 97 |

TABLE A-continued

B Cell Epitopes

| Organism | Gene | Sequence | Citation* | SEQ ID NO |
|---|---|---|---|---|
| | | PPQKNQSQPVVTKA | | 98 |
| | | PPSKGQTGNKVTKG | | 99 |
| | | PPSKSQPQVKVTKA | | 100 |
| | | QPQTANTQQGGKVKVTKA | | 101 |
| | | QPQVTNGVQGNQVKVTKA | | 102 |
| | | QPSKAQGQTNNQVKVTKA | | 103 |
| | | PPSSNQGKNQAQTGNTVTKA | | 104 |
| | | PPSKSQGKTGNQVKVTKA | | 105 |
| | | PPSKSQGTNNNQVKVTKA | | 106 |
| | | PPSKSQPGQVKVTKVTKA | | 107 |
| | | QLQLTEQPSSTNGQTGNQVKVT-KA | | 108 |
| | | QLQLTEAPSKSQGAASNQVKVT-KA | | 109 |
| | | SAYTPAHVYVDNKVAKHVA | | 110 |
| | | SAYTPAHFVQNKQNNNPTLVP | | 111 |
| | | VEGRNYQLQLTE | | 112 |
| | | PAQNSKSAYTPA | | 113 |
| | | QLQLTEPPSKNQAQTQNKVTKA | | 114 |
| | | GRDAFELFLLGSGSDE | | 115 |
| | | RHANVGRDAFELFLLGSGSDEA-KGTDPLKNH | | 116 |
| | | GRDAFNLFLLGRIGDDDE | | 117 |
| | | GRNAFELFLIGSATSDQ | | 118 |
| | | QVKVTKAKSRIRTKI | | 119 |
| | | TLVPAVVGKPGSD | | 120 |
| | NspA | HAKASSSLGSAKGFSPR | | 121 |
| | | TRYKNYKAPSTDFKL | | 122 |
| | | SLNRASVDLGGSDSFSQT | | 123 |
| | | GKVNTVKNVRSGELSAGVRVK | | 124 |
| | | GKVNTVKNVRSGELSVGVRVK | | 125 |
| Immunoglobulin E | | APEWPGSRDKRTL | | 126 |
| | | EDGQVMDVD | | 127 |
| | | STTQEGEL | | 128 |
| | | GHTFEDSTKK | | 129 |
| | | GGGHFPPT | | 130 |
| | | PGTINI | | 131 |
| | | FTPPT | | 132 |
| | | INHRGYWV | | 133 |

TABLE A-continued

B Cell Epitopes

| Organism | Gene | Sequence | Citation* | SEQ ID NO |
|---|---|---|---|---|
| | | GEFCINHRGYWVCGDPA | | 134 |
| | | MAPEWPGSRDKRTL | | 135 |
| | | MEDGQVMDVD | | 136 |
| | | MSTTQEGEL | | 137 |
| | | MGHTFEDSTKK | | 138 |
| | | MGGGHFPPT | | 139 |
| | | MPGTINI | | 140 |
| | | MFTPPT | | 141 |
| | | MINHRGYWV | | 142 |
| | | MGEFCINHRGYWVCGDPA | | 143 |
| Hepatitis B | Surface | | | |
| | PreS1 | MGTNLSVPN-PLGFFPDHQLDP | 36 | 144 |
| | | PLGFFPDH | | 145 |
| | | PLGFFPDHQL | | 146 |
| | PreS2 | MQWNSTAFHQ-TLQDPRVRG-LYLPAGG | 36 | 147 |
| | | MQWNSTAFHQ-TLQDP | | 148 |
| | | MQWNSTALHQ-ALQDP | | 149 |
| | | QDPRVR | 37 | 150 |
| | | QDGRVR | 37 | 151 |
| | | DPRVRG-LYLPAGG | 38 | 152 |
| | | DPRVRG-LYFPAGG | 39 | 153 |

*Citations to published epitopes are provided following Table B.

In the above influenza A M2 sequence of SEQ ID NO: 32, residues $X_1$ through $X_8$ are absent or present, and when present are the residues naturally present in the M2 protein sequence that are methionine, serine, leucine, leucine, threonine, glutamic acid, valine, and glutamic acid, respectively, with the proviso that when one subscripted X residue is present, any remaining subscripted X with a higher subscript number up to 8 is also present, residues $X_{15}$ and $X_{16}$ are present or absent, and when present are tryptophan and glycine, respectively, residues $X_{17}$ and $X_{19}$ are present or absent, and when present are independently cysteine, serine, or alanine, residue $X_{18}$ is present or absent, and when present is arginine, and residues $X_{20}$ through $X_{24}$ are present or absent, and when present are the residues naturally present in the M2 protein sequence that are asparagine, aspartic acid, serine, serine and aspartic acid respectively, with the proviso that when one subscripted X residue is present, any remaining subscripted X residue with a lower subscript number down to 15 is also present.

The remaining residues of Domain II that are present on either side of the heterologous residue or sequence are the residues of HBc position 76 through position 85. Thus, in a typical example, where residues 78 through 82 have been replaced, the chimer sequence in Domain II is 76 through 77, followed by restriction site-encoded residues, the immunogenic (epitope) sequence, further restriction site-encoded residues, and then HBc sequence 84 through 85. A typical exemplary sequence of a chimer prepared by an insertion strategy between residues 78 and 79 is that of HBc from position 2 through 78, followed by restriction site-encoded residues, the immunogenic sequence, further restriction site-encoded residues and HBc sequence 79 through 85. The sequence of other contemplated chimers through Domains I and II should be apparent from these illustrations and those that follow and need not be enumerated.

It has been found that a short hydrophilic peptide containing a plurality of glycine residues and having a length of about 5 to about 9 residues peptide-bonded at the C-terminus of an above-noted *Neisseria meningitidis* B cell epitope sequence can assist in the expression of a chimeric particle containing that sequence. One useful short peptide is that disclosed in Karpenko et al., *Amino Acids* (2000) 18:329-337, having the sequence GSGDEGG of SEQ ID NO:144.

As already noted, a heterologous chemically non-reactive residue or linker for a conjugated epitope can be peptide-bonded at a position in the HBc sequence between amino acid residues 76 and 85. As was the case for the immunogenic epitope, the HBc sequence of residues 76 through 85 is preferably present, but interrupted by the added residue or residues. This chimer preferably includes the HBc sequence of position 4 through at least position 140, plus a cysteine residue near the N-terminus or the C-terminus of the chimer protein. More preferably, the HBc sequence of positions 1 through 149 are present, but interrupted between residues 76 and 85 by the heterologous linker for a conjugated epitope, and the chimer molecule contains a C-terminal cysteine.

A chemically non-reactive residue was discussed previously. The heterologous linker for a conjugated epitope is most preferably a lysine (K) residue. Glutamic or aspartic acid, tyrosine and cysteine residues can also be used as linker residues, as can tyrosine and cysteine residues. It is noted that more than one linker can be present such as a sequence of three lysines, but such use is not preferred because heterogeneous conjugates can be formed from such use in which the conjugated hapten is bonded to one linker in a first chimer and to a different linker in a second chimer molecule. U.S. Pat. No. 6,231,864 B1 discloses HBc chimer molecules containing one or more linking residues, but lacking a stabilizing N-terminal cysteine residue.

It is also noted that an inserted chemically non-reactive residue, linker residue or immunogenic epitope-containing sequence present in a contemplated HBc chimer can also be separated from the HBc sequence residues by a "flexible linker arm" on one or both sides of (flanking) the immunogenic (epitope) sequence. This is particularly the case where the immunogenic sequence is greater than about 30 amino acid residues long. Exemplary flexible linker arm sequences typically contain about 4 to about 10 glycine residues that are thought to permit the inserted sequence to "bulge" outwardly from the otherwise bulging loop sequence and add further stability to the construct. These flexible linker arms are similar to those discussed before in relation to a *Neisseria meningitidis* B cell epitope sequence such as the peptide of SEQ ID NO: 125. Illustrative other flexible linker arm sequences are disclosed in Kratz et al. (March 1999) *Proc. Natl. Acad. Sci., U.S.A.*, 96:1915-1920 and are exemplified by the amino acid residue sequences:

| GGGGSGGGGT | SEQ ID NO: 155 |
|---|---|
| GGGGSGGGG. | SEQ ID NO: 156 |

The sequence immediately below is utilized at the C-terminus of an inserted epitope-containing sequence, whereas the sequences thereafter are used at each of the N- and C-termini of inserted immunogenic sequences

| GSGDEGG | SEQ ID NO: 154 |
|---|---|
| GGGGSGGG | SEQ ID NO: 157 |

As was noted previously, Domain III constitutes the sequence of HBc from position 86 through position 135. Consequently, the sequence of the illustrative chimers discussed above for Domains I and II, can be extended so that the first-discussed chimer has the sequence of HBc from position 84 through position 140, and the second-discussed chimer has the sequence of HBc from position 79 through position 140.

Domain IV is a sequence that (i) includes a HBc sequence from position 136 through 140 and optionally through position 149, (ii) contains zero up to three cysteine residues, and (iii) up to about 100 amino acid residues in an immunogenic sequence that is preferably heterologous to HBc at position 165 to the C-terminus, with the proviso that Domain IV contains at least 5 amino acid residues of the HBc sequence from position 136 through 140. The Domain IV immunogenic sequence more preferably contains up to about 50 amino acid residues, and most preferably contains up to about 25 residues. The Domain IV sequence can thus be substantially any sequence, except the C-terminal HBc sequence from position 165 to the C-terminus.

The length of the Domain IV sequence can be five residues; i.e., the residue of position 136 through 140, up to about 125 amino acid residues (up to about HBc position 165 plus up to about 100 immunogenic residues of an immunogenic sequence) including up to a total of three cysteines, with the length being sufficient so that a contemplated chimeric protein has a total length of about 135 to about 525 residues. Where an epitope peptide-bonded to one or both of Domains I or II contains up to about 30 or about 50 residues, respectively, as is preferred for those epitopes, more preferred lengths of the chimer molecule, including the Domain IV epitope, are about 170 to about 250 residues. Particularly preferred chimer molecules containing two immunogenic epitopes have a length of about 190 to about 210 residues. Freedom of the resulting particle from nucleic acid binding is determined by determination of the 280:260 absorbance ratio as discussed previously.

The Domain IV sequence can include zero up to three Cys residues. When present, it is preferred that the one or more Cys residues be at or within about five amino acid residues of the C-terminus of the chimeric protein molecule. In addition, when more than one Cys residue is present in a Domain IV sequence, it is preferred that those Cys residues be adjacent to each other.

It is preferred that the Domain IV sequence constitute a T cell epitope, a plurality of T cell epitopes that are the same or different or an additional B cell epitope for the organism against which a contemplated chimer is intended to be used as an immunogen. Exemplary Domain IV T cell epitope sequences are provided in Table B, below, as in Table A, with illustrative added C-terminal cysteine residues underlined.

TABLE B

T Cell Epitopes

| Organism | Gene | Sequence* | Citation | SEQ ID NO |
|---|---|---|---|---|
| HIV | P24 | GPKEPFRDYVDRFYKC | 3 | 15 |
| Corynebacterium diptheriae | toxin | FQVVHNSYNRPAYSPGC | 5 | 159 |
| Borrelia burgdorferi | ospA | VEIKEGTVTLKREIDKNGKVTVSLC | 6 | 160 |
| | | TLSKNISKSGEVSVELNDC | 7 | 161 |
| Influenza Virus A8/PR8 | HA | SSVSSFERFEC | 8 | 162 |
| | | LIDALLGDPC | 32 | 163 |
| | | TLIDALLGC | 32 | 164 |
| Trypanosoma cruzi | | SHNFTLVASVIIEEAPSGNTC | 13 | 165 |
| Plasmodium falciparum | MSP1 | SVQIPKVPYPNGIVYC | 15 | 166 |
| | | DFNHYYTLKTGLEADC | | 167 |
| | | PSDKHIEQYKKIKNSISC | 23 | 168 |
| | | EYLNKIQNSLSTEWSPCSVT | 26 | 169 |
| P. vivax | | YLDKVRATVGTEWTPCSVT | | 170 |
| P. yoelii | | EFVKQISSQLTEEWSQCSVT | | 171 |
| Streptococcus sobrinus | AgI/II | KPRPIYEAKLAQNQKC | 16 | 172 |
| | | AKADYEAKLAQYEKDLC | | 173 |
| LCMV (lymphocytic choriomeningitis virus) | NP | RPQASGVYMGNLTAQC | 17 | 174 |
| Clostridium tetani | tox | QYIKANSKFIGITELC | 20 | 175 |
| Neisseria meningitidis | PorB | AIWQVEQKASIAGTDSGWC | | 176 |
| | | NYKNGGFFVQYGGAYKRHC | | 177 |
| | | HNSQTEVAATLAYRFGNVC | | 178 |
| | PorB | TPRVSYAHGFKGLVDDADC | | 179 |
| | | RFGNAVPRISYAHGFDFIC | | 180 |
| | | AFKYARHANVGRNAFELFC | | 181 |

TABLE B-continued

T Cell Epitopes

| Organism | Gene | Sequence* | Citation | SEQ ID NO |
|---|---|---|---|---|
| | | SGAWLKRNTGIGNYTQINAC | | 182 |
| | | AGEFGTLRAGRVANQC | | 183 |
| | | IGNYTQINAASVGLRC | | 184 |
| | | GRNYQLQLTEQPSRTC | | 185 |
| | | SGSVQFVPAQNSKSAC | | 186 |
| | | HANVGRDAFNLFLLGC | | 187 |
| | | LGRIGDDDEAKGTDPC | | 188 |
| | | SVQFVPAQNSKSAYKC | | 189 |
| | | NYAFKYAKHANVGRDC | | 190 |
| | | AHGFDFIERGKKGENC | | 191 |
| | | GVDYDFSKRTSAIVSC | | 192 |
| | | HDDMPVSVRYDSPDFC | | 193 |
| | | RFGNAVPRISYAHGFDFIERGKKGENC | | 194 |
| | | NYAFKYAKHANVGRDAFNLFLLGC | | 195 |
| | | SGAWLKRNTGIGNYTQINAASVGLRC | | 196 |
| | | SGSVQFVPAQNSKSAYTPAC | | 197 |
| | OpaB | TGANNTSTVSDYFRNRITC | | 198 |
| | | IYDFKLNDKFDKFKPYIGC | | 199 |
| | Opa-5d | LSAIYDFKLNDKFKPYIGC | | 200 |
| | Opac | NGWYINPWSEVKFDLNSRC | | 201 |
| Hepatitis B | Surface | | | |
| | PreS1 | MGTNLSVPN-PLGFFPDHQLDP | 36, 40 | 144 |
| | | PLGFFPDH | | 145 |
| | | PLGFFPDHQL | | 146 |
| | PreS2 | MQWNSTAFHQ-TLQDPRVRG-LYLPAGG | 36 | 147 |
| | | MQWNSTAFHQ-TLQDP | | 148 |
| | | MQWNSTALHQ-ALQDP | | 149 |
| | | QDPRVR | 37 | 150 |
| | | QDGRVR | 37 | 151 |

*Underlined C (C) is not from the native sequence.

CITATIONS

1. EPO 786 521A.
2. WO 98/07320.
3. U.S. Pat. No. 5,639,854.
4. U.S. Pat. No. 4,544,500.
5. EPO 399001 B1.
6. Bockenstedt et al. (1996) *J. Immunol.*, 157, 12:5496.
7. Zhong et al. (1996) *Eur. J. Immunol.*, 26, 11:2749.
8. Brumeanu et al. (1996) *Immunotechnology*, 2, 2:85.
9. Hill et al. (1997) *Infect. Immun.*, 65, 11:4476.
10. EPO 432 220 B1.
11. WO 98/06851.
12. Kelly et al. (1997) *Clin. Exp. Immunol.*, 110, 2:285.
13. Kahn et al. (1997) *J. Immunol.*, 159, 9:4444.
14. WO 97/18475.
15. Ohta et al.; (1997) *Int. Arch. Allergy Immunol.*, 114, 1:15.
16. Staffileno et al. (1990) *Arch. Oral Biol.*, 35: Suppl. 47S.
17. Saron et al. (1997) *Proc. Natl. Acad. Sci. USA*, 94, 7:3314.
18. Corthesy et al. (1996) *J. Biol. Chem.*, 271, 52:33670.
19. Bastien et al. (1997) *Virol.*, 234, 1:118.
20. Yang et al. (1997) *Vaccine*, 15, 4:377.
21. Lotter et al. (1997) *J. Exp. Med.*, 185, 10:1793.
22. Nara et al. (1997) *Vaccine* 15, 1:79.
23. U.S. Pat. No. 4,886,782.
24. Zavala et al. (1985) *Science*, 228:1436.
25. Schodel et al. (1994) *J. Exper. Med.*, 180:1037.
26. Calvo-Calleet al. (1997) *J. Immunol.* 159, 3:1362.
27. Qari et al. (1992) *Mol. Biochem. Parasitol.*, 55(1-2):105.
28. Qari et al. (1993) *Lancet*, 341(8848):780.
29. Neirynck et al. (October 1999) *Nature Med.*, 5(10):1157-1163.
30. Thompson et al. (1994) *Eur.J. Biochem.*, 226(3):751-764.
31. Wilson et al. (2000) *Science*, 287:1664-1666.
32. Brown et al. (1993) *J. Virol.*, 67(5):2887-2893.
33. U.S. Pat. No. 4,886,663.
34. Schenk et al. (Jul. 8, 1999) *Nature*, 400(6740):116-117.
35. Slepushkin et al. (1995) *Vaccine*, 13(15):1399-1402.
36. Neurath et al., (1986) F. Brown et al. eds., *Vaccines* 85, Cold Spring Harbor Laboratory, Cold Spring Harbor, N.Y., pp.185-189.
37. Kent et al., (1987) F. Brown et al. eds., *Vaccines* 86, Cold Spring Harbor Laboratory, Cold Spring Harbor, N.Y., pp.365-369.
38. Milich et al., (1987) F. Brown et al. eds., *Vaccines* 86, Cold Spring Harbor Laboratory, Cold Spring Harbor, N.Y., pp.377-382.
39. Thornton et al., (1987) F. Brown et al. eds., *Vaccines* 87, Cold Spring Harbor Laboratory, Cold Spring Harbor, N.Y., pp.77-80.
40. Milich et al., (1987) F. Brown et al. eds., *Vaccines* 87, Cold Spring Harbor Laboratory, Cold Spring Harbor, N.Y., pp.50-55.

The amino acid sequence of HBc from residue position 4 through at least position 140 is preferably present in a contemplated chimer molecule and particle. The sequence from position 2 through position 149 and up to position about 165 is more preferably present. A B cell epitope, when present, is preferably present between residues 76 and 85. At least a single cysteine residue is present at or near the N-terminus in Domain I as already noted or at or near the C-terminus, as discussed before. One or more T cell epitopes can also be present as an N-terminal or C-terminal addition to the HBc sequence. A contemplated recombinant HBc chimer is substantially free of bound nucleic acid. A contemplated chimer particle that contains an added N-terminal or C-terminal Cys residue is also more stable after formation than is a similar particle that does not contain that added Cys.

A contemplated recombinant HBc chimer molecule is typically present and is used as a self-assembled particle. These particles are comprised of 180 to 240 chimer molecules (90 or 120 dimer pairs), usually 240 chimer molecules, that separate into protein molecules in the presence of disulfide reducing agents such as 2-mercaptoethanol, and the individual molecules are therefore thought to be bound together into the particle primarily by disulfide bonds.

Although not wishing to be bound by theory, it is believed that the observed enhanced stability and in some cases enhanced expression for a contemplated HBc chimer is due to the formation of an N-terminal cystine disulfide bond between chimer protein molecules of the particles. Regardless of whether present as a cysteine or a cystine, the N-terminal cysteine(s) residue is referred to as a cysteine inasmuch as that is the residue coded-for by the codon present in the nucleic acid from which the protein and assembled particle is expressed.

These particles are similar to the particles observed in patients infected with HBV, but these particles are non-infectious. Upon expression in various prokaryotic and eukaryotic hosts, the individual recombinant HBc chimer molecules assemble in the host into particles that can be readily harvested from the host cells, and purified, if desired.

As noted before, the HBc immunodominant loop is usually recited as being located at about positions 75 through 85 from the amino-terminus (N-terminus) of the intact protein. An immunogenic epitope-containing sequence of Domain II is placed into that immunodominant loop sequence. That placement can substantially eliminate the HBc immunogenicity of the HBc loop sequence, while presenting the immunogenic sequence or linker residue in an extremely immunogenic position in the assembled chimer particles.

In addition to the before-discussed N- and C-truncations, insertion of various epitopes and spacers, a contemplated chimer molecule can also contain conservative substitutions in the amino acid residues that constitute HBc Domains I, II, III and IV. Conservative substitutions are as defined before. An illustrative conservative substitution is seen in the replacement of residues at positions 2 and 3 (aspartic acid and isoleucine; DI) by glutamic acid and leucine (EL) residues that are encoded by an EcoRI restriction site used to add nucleic acids that code for a desired N-terminal epitope, including an N-terminal cysteine residue.

More rarely, a "nonconservative" change, e.g., replacement of a glycine with a tryptophan is contemplated. Analogous minor variations can also include amino acid deletions or insertions, or both. Guidance in determining which amino acid residues can be substituted, inserted, or deleted without abolishing biological activity or particle formation can be found using computer programs well known in the art, for example LASERGENE software (DNASTAR Inc., Madison, Wis.)

The HBc portion of a chimer molecule of the present invention; i.e., the portion having the HBc sequence, that has other than a sequence or residue of an added epitope, linker, flexible linker arm or heterologous residue(s) that are a restriction enzyme artifact, most preferably has the amino acid residue sequence of subtype ayw that is shown in FIG. 1 (SEQ ID NO: 1), less any portion or portions of the subtype ayw sequence that are absent because of truncation at one or both termini. Typically, that sequence is that of HBc positions 2 through 149. Somewhat less preferred are the corresponding amino acid residue sequences of subtypes adw, adw2 and adyw that are also shown in FIG. 1 (SEQ ID NOs: 2, 3 and 4). Less preferred still are the sequences of woodchuck and ground squirrel at aligned positions 2 through 149 that are the last two sequences of FIG. 1 (SEQ ID NOs: 5 and 6). As noted elsewhere, portions of different sequences from different mammalian HBc proteins can be used together in a single chimer.

When the HBc portion of a chimer molecule of the present invention as above described has other than a sequence of a mammalian HBc molecule corresponding to positions 2 through about 165, no more than about 20 percent of the amino acid residues are substituted as compared to SEQ ID NO: 1 from position 2 through 165. It is preferred that no more than about 10 percent, and more preferably no more than about 5 percent, and most preferably no more than about 3 percent of the amino acid residues are substituted as compared to SEQ ID NO: 1 from position 2 through 165.

A contemplated chimer of 164 HBc residues can therefore contain up to about 32 residues that are different from those of SEQ ID NO: 1 at positions 2 through 165, and preferably about 16 residues. More preferably, about 8 residues are different from the ayw sequence (SEQ ID NO: 1) at residue positions 2-165, and most preferably about 5 residues are different. Substitutions, other than in the immunodominant loop of Domain II or at the termini, are preferably in the non-helical portions of the chimer molecule and are typically between residues 2 to about 15 and residues 24 to about 50 to help assure particle formation. See, Koschel et al. (March 1999), *J. Virol.*, 73(3):2153-2160.

Where a HBc sequence is truncated at the C-terminus beyond position 165 or at the N-terminus, or contains one or more deletions in the immunogenic loop, the number of substituted residues is proportionally fewer because the total length of the sequence is less than 164 residues. Deletions elsewhere in the molecule are considered conservative substitutions for purposes of calculation.

In yet another aspect of the invention, one or preferably both cysteine residues at HBc positions 48 and 107 is replaced by another residue such as a preferred serine residue in any of the previously discussed HBc chimer molecules. Those self-assembled particles are more stable than are particles formed from otherwise identical HBc chimer molecules that contain both cysteine residues at positions 48 and 107 after storage at 37° C. in a 20 mM sodium phosphate buffer at pH 6.8 for a time period of 14 days. Thus, the absence of one or, more preferably, both cysteines at residue positions 48 and 107 enhances the storage stability of a particle that is otherwise stabilized by the presence of an N- or C-terminal cysteine or both.

The usually present HBc cysteine residues at positions 48 and 107 are thus replaced by other residues such as serine, threonine, leucine, isoleucine, asparagine or glutamine in all contemplated chimer molecules and the contemplated chimer molecules contain at least one N- or C-terminal cysteine residue that is not native to the HBc sequence. Thus, in some embodiments, it is preferred that the HBc sequence of Domain I include the residues of position 5 through position 75 along plus at least an N-terminal cysteine residue. In other embodiments, it is preferred that a contemplated chimer molecule contain not only an N-terminal cysteine residue, but also contain one cysteine residue within Domain IV as noted above that is alone or in an amino acid residue sequence. In yet other embodiments, a preferred chimer molecule contains only one or more C-terminal cysteine residues and Domain I is free of non-HBc cysteine residues. An HBc cysteine residue is present at about position 61 in each of the HBc sequences of FIG. 1.

Chimer Preparation

A contemplated chimeric HBc immunogen is typically prepared using the well-known techniques of recombinant DNA technology. Thus, sequences of nucleic acid that encode particular polypeptide sequences are added to and deleted from the precursor sequence that encodes HBc to form a nucleic acid that encodes a contemplated chimer.

An illustrative contemplated chimeric immunogen typically utilizes a cysteine residue present in the influenza A M2 sequence as the N-terminal cysteine. Primers for the preparation of such chimer molecules by in vitro mutagenesis of a polynucleotide encoding an HBc molecule are discussed hereinafter. When a cysteine-containing M2 polypeptide epitope is not present at the N-terminus, the N-terminal cysteine can be provided by in vitro mutagenesis using a primer that encodes just a cysteine-containing portion of the M2 polypeptide or a simple N-terminal start sequence such as Met-Cys- or Met-Gly-Cys-.

In yet another aspect of the invention, the recombinantly produced immunogenic chimer particles are administered to HBV-infected patients concurrently with recombinant hepatitis B surface antigen (HBsAg). The recombinant hepatitis B surface antigen can optionally contain one or both of the PreS1 or PreS2 regions.

Methods of manufacturing hepatitis B surface antigen are well known in the art. An example of production of recombinant hepatitis B surface antigen in yeast is described in U.S. Pat. No. 4,977,092. The HBc chimer particles and HBsAg can be present in the same container or can be presented as a kit in which the HBc chimer particles are present in one container, the HBsAg is present in a second container and the two are admixed prior to injection. A preferred dose of HBsAg is about 10 to about 100 µg, and most preferably about 20 to about 50 µg. The HBsAg is optionally formulated on aluminium hydroxide gel. In a preferred method of use, the combined HBc particles and HBsAg are administered in conjunction with and adjuvant such as MPL or RC-529.

Once immunized, the patient is maintained for a period of time sufficient for the induction of an immune response to the HBc chimer particles. The maintenance time typically lasts for a period of about three to about twelve weeks, and can include a booster, second immunizing administration of the vaccine. Subsequent booster administrations are also contemplated.

The production of anti-HBsAg or other antibodies is readily ascertained by obtaining a plasma or serum sample from the immunized patient and assaying the antibodies therein for their ability to bind to an appropriate antigen such as a synthetic HbsAg polypeptide antigen in an ELISA assay as described hereinafter or by another immunoassay such as a Western blot as is well known in the art.

Either of two strategies is preferred for placing the immunogenic epitope sequence, chemically reactive linker residue sequence or chemically non-reactive sequence into the loop sequence. The first strategy is referred to as replacement in which DNA that codes for a portion of the immunodominant loop is excised and replaced with DNA that encodes an immunogenic epitope such as a B cell sequence. The second strategy is referred to as insertion in which an immunogenic epitope is inserted between adjacent residues in the loop.

Site-directed mutagenesis using the polymerase chain reaction (PCR) is used in one exemplary replacement approach to provide a chimeric HBc DNA sequence that encodes a pair of different restriction sites, e.g. EcoRI and SacI, one near each end of the immunodominant loop-encoding DNA. Exemplary residues replaced are 76 through 81. The loop-encoding section is excised, a desired sequence that encodes the immunogenic B cell epitope is ligated into the restriction sites and the resulting DNA is used to express the HBc chimer. See, for example, Table 2 of Pumpens et al., (1995) *Intervirology*, 38:63-74 for exemplary uses of this technique.

Alternatively, a single restriction site or two sites can be encoded into the region by site-directed mutagenesis, the DNA cut with a restriction enzyme to provide "sticky" ends. The sticky ends can be used for ligation or made blunt with endonuclease and a blunt-ended heterologous DNA segment ligated into the cut region. Examples of this type of sequence replacement into HBc can be found in the work reported in Schodel et al., (1991) F. Brown et al. eds., *Vaccines* 91, Cold Spring Harbor Laboratory, Cold Spring Harbor, N.Y., pp.319-325; Schodel et al., *Behring Inst. Mitt.*, 1997(98): p. 114-119 and Schodel et al., *J. Exp. Med.*, (1994) 180(3): p. 1037-4, the latter two papers discussing the preparation of vaccines against *P. yoelii* and *P. berghei*, respectively.

The insertion position within the HBc immunogenic loop and the presence of loop residues can be of import to the activity of the immunogen. Thus, as is illustrated beforementioned published PCT applications PCT/US01/25625 and PCT/US01/41759, placement of a malarial B cell epitope between HBc residue positions 78 and 79 provides a particulate immunogen that is ten to one thousand times more immunogenic than placement of the same immunogen in an excised and replaced region between residues 76 and 81. In addition, placement of the same malarial immunogen between residues 78 and 79 as compared to between residues 77 and 78 provided an unexpected enhancement in immunogenicity of about 15-fold.

Insertion is therefore generally preferred. In an illustrative example of the insertion strategy, site-directed mutagenesis is used to create two restriction sites adjacent to each other and between codons encoding adjacent amino acid residues, such as those at residue positions 78 and 79. This technique adds twelve base pairs that encode four amino acid residues (two for each restriction site) between formerly adjacent residues in the HBc loop.

Upon cleavage with the restriction enzymes, ligation of the DNA coding for the immunogenic B cell epitope sequence and expression of the DNA to form HBc chimers, the HBc loop amino acid sequence is seen to be interrupted on its N-terminal side by the two residues encoded by the 5' restriction site, followed toward the C-terminus by the immunogenic B-cell epitope sequence, followed by two more immunogenic, non-loop residues encoded by the 3' restriction site and then the rest of the loop sequence. This same strategy can be used for insertion into Domain I of an N-terminal cysteine or N-terminal immunogenic sequence as was reported in Neirynck et al., (October 1999) *Nature Med.*, 5(10):1157-1163 or for insertion into Domain IV of a T cell epitope or one or more cysteine residues. A similar strategy using an insertion between residues 82 and 83 is reported in Schodel et al., (1990) F. Brown et al. eds., *Vaccines* 90, Cold Spring Harbor Laboratory, Cold Spring Harbor, N.Y., pp.193-198.

More specifically, a DNA sequence that encodes a C-terminal truncated HBc sequence (e.g., HBc149) is engineered to contain adjacent EcoRI and SacI sites between residues 78 and 79. Cleavage of that DNA with both enzymes provides one fragment that encodes HBc positions 1-78 3'-terminated with an EcoRI sticky end, whereas the other fragment has a 5'-terminal SacI sticky end and encodes residues of positions 79-149. Ligation of a synthetic nucleic acid having a 5' AATT overhang followed by a sequence that encodes a desired B cell epitope and a AGCT 3'overhang provides a HBc chimer sequence that encodes that B cell epitope flanked on each side by two heterologous residues [GlyIle (GI) and GluLeu (EL), respectively] between residues 78 and 79, while usually destroying the EcoRI site and preserving the SacI site.

A similar strategy for insertion of a cysteine-containing sequence in Domain IV, such as a malarial T cell epitope that contains the *P. falciparum* CS protein sequence from position 326 through position 345 and is referred to herein as PF/CS326-345 (Pf-UTC). Here, EcoRI and HindIII restriction sites are engineered into the HBc DNA sequence after amino acid residue position 149. After digestion with EcoRI and HindIII, a synthetic DNA having the above AATT 5'overhang followed by a T cell epitope-encoding sequence, one or more stop codons and a 3' AGCT overhang were ligated into the digested sequence to form a sequence that encoded HBc residues 1-149 followed by two heterologous residues (GI), the stop codon and the HindIII site.

PCR amplification using a forward primer having a SacI restriction site followed by a sequence encoding HBc beginning at residue position 79, followed by digestion with SacI and HindIII provided a sequence encoding HBc positions 79-149 plus the two added residues and the T cell epitope at the C-terminus. Digestion of the construct with SacI and ligation provides the complete gene encoding a desired recombinant HBc chimer immunogen having the sequence, from the N-terminus, of HBc positions 1-78, two added residues, the malarial B cell epitope, two added residues, HBc positions 79-149, two added residues, and the T cell epitope that is shown in FIG. 2C.

Similar techniques can be used to place a heterologous linker residue for conjugation of a B cell epitope into the loop region sequence. Contemplated linker residues include lysine (Lys), which is particularly preferred, aspartic acid (Asp), glutamic acid (Glu), cysteine (Cys) and tyrosine (Tyr).

It is noted that the amino acid residue sequence shown in SEQ ID NO:1 contains a Glu and an Asp residue at positions 77 and 78. Nonetheless, introduction of an additional, heterologous, carboxyl-containing residue is still contemplated. The chemical reactivity of the existing glutamic and aspartic acids may be reduced by other factors. For example, it is known in the art that a neighboring proline, such as that found at position 79, can neutralize and thereby reduce the chemical reactivity of a proximal carboxyl group.

Here, using the first noted insertion strategy, five heterologous residues are placed into the loop sequence; one that is the heterologous linker residue for conjugating a B cell epitope and two residues adjacent on either side of that one residue that are themselves also adjacent to loop sequence residues and are an expression product of the inserted restriction sites (restriction enzyme artifacts). It is noted that one can also use site-directed mutagenesis to add a single codon into the HBc loop sequence that encodes the heterologous linker residue for a B cell epitope.

It is noted that the preferred use of two heterologous residues on either side of (flanking) a B cell or T cell epitope is a matter of convenience. As a consequence, one can also use zero to three or more added residues that are not part of the HBc sequence on either or both sides of an inserted sequence. One or both ends of the insert and HBc nucleic acid can be "chewed back" with an appropriate nuclease (e.g. S1 nuclease) to provide blunt ends that can be ligated together. Added heterologous residues that are neither part of the inserted B cell or T cell epitopes nor a part of the HBc sequence are not counted in the number of residues present in a recited Domain, unless those residues are conservative replacements for residues already present, as where the residues GluLeu replace AspIle in some of the constructs discussed hereinafter.

It is also noted that one can also synthesize all or a part of a desired recombinant HBc chimer nucleic acid using well-known synthetic methods as is discussed and illustrated in U.S. Pat. No. 5,656,472 for the synthesis of the 177 base pair DNA that encodes the 59 residue ribulose bis-phosphate carboxylase-oxygenase signal peptide of *Nicotiana tabacum*. For example, one can synthesize Domains I and II with a blunt or a "sticky end" that can be ligated to Domains III and IV to provide a construct that expresses a contemplated HBc chimer that contains zero added residues to the N-terminal side of the B cell epitope and zero to three added residues on the C-terminal side or at the Domain II/III junction or at some other desired location.

An alternative insertion technique was reported in Clarke et al. (1991) F. Brown et al. eds., *Vaccines* 91, Cold Spring Harbor Laboratory, Cold Spring Harbor, N.Y., pp.313-318. Here, taking advantage of the degeneracy of the genetic code, those workers engineered a single restriction site corresponding to residues 80 and 81 that encoded the original residues present at those positions. Their expressed HBc chimers thereby contained no restriction site-encoded residues, and contained the residues of the HBc loop immediately adjacent to the inserted sequence.

A nucleic acid sequence (segment) that encodes a previously described HBc chimer molecule or a complement of that coding sequence is also contemplated herein. Such a nucleic acid segment is present in isolated and purified form in some preferred embodiments.

In living organisms, the amino acid residue sequence of a protein or polypeptide is directly related via the genetic code to the deoxyribonucleic acid (DNA) sequence of the gene that codes for the protein. Thus, through the well-known degeneracy of the genetic code additional DNAs and corresponding RNA sequences (nucleic acids) can be prepared as desired that encode the same chimer amino acid residue sequences, but are sufficiently different from a before-discussed gene sequence that the two sequences do not hybridize at high stringency, but do hybridize at moderate stringency.

High stringency conditions can be defined as comprising hybridization at a temperature of about 50°-55° C. in 6×SSC and a final wash at a temperature of 68° C. in 1-3×SSC. Moderate stringency conditions comprise hybridization at a temperature of about 50° C. to about 65° C. in 0.2 to 0.3 M NaCl, followed by washing at about 50° C. to about 55° C. in 0.2×SSC, 0.1% SDS (sodium dodecyl sulfate).

A nucleic sequence (DNA sequence or an RNA sequence) that (1) itself encodes, or its complement encodes, a chimer molecule whose HBc portion from residue position 4 through 136, when present, is that of SEQ ID NOs: 1, 2, 3, 4, 5 or 6 and (2) hybridizes with a DNA sequence of SEQ ID NOs:202, 203, 204, 205, 206 or 207, at least at moderate stringency (discussed above); and (3) whose HBc sequence shares at least 80 percent, and more preferably at least 90 percent, and even more preferably at least 95 percent, and most preferably 100 percent identity with a DNA sequence of SEQ ID NOs: 202, 203, 204, 205, 206 and 207, is defined as a DNA variant sequence. As is well-known, a nucleic acid sequence such as a contemplated nucleic acid sequence is expressed when operatively linked to an appropriate promoter in an appropriate expression system as discussed elsewhere herein.

An analog or analogous nucleic acid (DNA or RNA) sequence that encodes a contemplated chimer molecule is also contemplated as part of this invention. A chimer analog nucleic acid sequence or its complementary nucleic acid sequence encodes a HBc amino acid residue sequence that is at least 80 percent, and more preferably at least 90 percent, and most preferably is at least 95 percent identical to the HBc sequence portion from residue position 4 through residue position 136 shown in SEQ ID NOs: 1, 2, 3, 4, 5 or 6. This DNA or RNA is referred to herein as an "analog of" or "analogous to" a sequence of a nucleic acid of SEQ ID NOs: 202, 203, 204, 205, 206 and 207, and hybridizes with the nucleic acid sequence of SEQ ID NOs: 202, 203, 204, 205, 206 and 207 or their complements herein under moderate stringency hybridization conditions. A nucleic acid that encodes an analogous sequence, upon suitable transfection and expression, also produces a contemplated chimer.

Different hosts often have preferences for a particular codon to be used for encoding a particular amino acid residue. Such codon preferences are well known and a DNA sequence encoding a desired chimer sequence can be altered, using in vitro mutagenesis for example, so that host-preferred codons are utilized for a particular host in which the enzyme is to be expressed. In addition, one can also use the degeneracy of the genetic code to encode the HBc portion of a sequence of SEQ ID NOs: 202, 203, 204, 205, 206 or 207 that avoids substantial identity with a DNA of SEQ ID Nos: 1, 2, 3, 4, 5 or 6 or their complements. Thus, a useful analogous DNA sequence need not hybridize with the nucleotide sequences of SEQ ID NOs: 202, 203, 204, 205, 206 or 207 or a complement under conditions of moderate stringency, but can still provide a contemplated chimer molecule.

A recombinant nucleic acid molecule such as a DNA molecule, comprising a vector operatively linked to an exogenous nucleic acid segment (e.g., a DNA segment or sequence) that defines a gene that encodes a contemplated chimer, as discussed above, and a promoter suitable for driving the expression of the gene in a compatible host organism, is also contemplated in this invention. More particularly, also contemplated is a recombinant DNA molecule that comprises a vector comprising a promoter for driving the expression of the chimer in host organism cells operatively linked to a DNA segment that defines a gene for the HBc portion of a chimer or a DNA variant that has at least 90 percent identity to the chimer gene of SEQ ID NOs: 202, 203, 204, 205, 206 or 207 and hybridizes with that gene under moderate stringency conditions.

Further contemplated is a recombinant DNA molecule that comprises a vector containing a promoter for driving the expression of a chimer in host organism cells operatively linked to a DNA segment that is an analog nucleic acid sequence that encodes an amino acid residue sequence of a HBc chimer portion that is at least 80 percent identical, more preferably 90 percent identical, and most preferably 95 percent identical to the HBc portion of a sequence of SEQ ID NOs: 1, 2, 3, 4, 5 or 6. That recombinant DNA molecule, upon suitable transfection and expression in a host cell, provides a contemplated chimer molecule.

It is noted that because of the 30 amino acid residue N-terminal sequence of ground squirrel HBc does not align with any of the other HBc sequences, that sequence and its encoding nucleic acid sequences and their complements are not included in the above percentages of identity, nor are the portions of nucleic acid that encode that 30-residue sequence or its complement used in hybridization determinations. Similarly, sequences that are truncated at either or both of the HBc N- and C-termini are not included in identity calculations, nor are those sequences in which residues of the immunodominant loop are removed for insertion of an immunogenic epitope. Thus, only those HBc-encoding bases or HBc sequence residues that are present in a chimer molecule are included and compared to an aligned nucleic acid or amino acid residue sequence in the identity percentage calculations.

Inasmuch as the coding sequences for the gene disclosed herein is illustrated in SEQ ID NOs: 172, 173, 174, 175, 176 and 177, isolated nucleic acid segments, preferably DNA sequences, variants and analogs thereof can be prepared by in vitro mutagenesis, as is well known in the art and discussed in *Current Protocols In Molecular Biology*, Ausabel et al. eds., John Wiley & Sons (New York: 1987) p. 8.1.1-8.1.6, that begin at the initial ATG codon for a gene and end at or just downstream of the stop codon for each gene. Thus, a desired restriction site can be engineered at or upstream of the initiation codon, and at or downstream of the stop codon so that other genes can be prepared, excised and isolated.

As is well known in the art, so long as the required nucleic acid, illustratively DNA sequence, is present, (including start and stop signals), additional base pairs can usually be present at either end of the segment and that segment can still be utilized to express the protein. This, of course, presumes the absence in the segment of an operatively linked DNA sequence that represses expression, expresses a further product that consumes the enzyme desired to be expressed, expresses a product that consumes a wanted reaction product produced by that desired enzyme, or otherwise interferes with expression of the gene of the DNA segment.

Thus, so long as the DNA segment is free of such interfering DNA sequences, a DNA segment of the invention can be about 500 to about 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

DNA segments that encode the before-described chimer can be synthesized by chemical techniques, for example, the phosphotriester method of Matteucci et al. (1981) *J. Am. Chem. Soc*., 103:3185. Of course, by chemically synthesizing the coding sequence, any desired modifications can be made simply by substituting the appropriate bases for those encoding the native amino acid residue sequence. However, DNA segments including sequences discussed previously are preferred.

A contemplated HBc chimer can be produced (expressed) in a number of transformed host systems, typically host cells although expression in acellular, in vitro, systems is also contemplated. These host cellular systems include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g. baculovirus); plant cell systems transformed with virus expression vectors (e.g. cauliflower mosaic virus; tobacco mosaic virus) or with bacterial expression vectors (e.g., Ti plasmid); or appropriately transformed animal cell systems such as CHO, VERO or COS cells. The invention is not limited by the host cell employed.

DNA segments containing a gene encoding the HBc chimer are preferably obtained from recombinant DNA molecules (plasmid vectors) containing that gene. Vectors capable of directing the expression of a chimer gene into the protein of a HBc chimer is referred to herein as an "expression vector".

An expression vector contains expression control elements including the promoter. The chimer-coding gene is operatively linked to the expression vector to permit the promoter sequence to direct RNA polymerase binding and expression of the chimer-encoding gene. Useful in expressing the polypeptide coding gene are promoters that are inducible, viral, synthetic, constitutive as described by Poszkowski et al. (1989) *EMBO J*., 3:2719 and Odell et al. (1985) *Nature*, 313:810, as well as temporally regulated, spatially regulated, and spatiotemporally regulated as given in Chua et al. (1989) *Science*, 244:174-181.

One preferred promoter for use in prokaryotic cells such as *E. coli* is the Rec 7 promoter that is inducible by exogenously supplied nalidixic acid. A more preferred promoter is present in plasmid vector JHEX25 (available from Promega Corp., Madison Wis.) that is inducible by exogenously supplied isopropyl-β-D-thiogalacto-pyranoside (IPTG). A still more preferred promoter, the tac promoter, is present in plasmid vector pKK223-3 and is also inducible by exogenously supplied IPTG. The pKK223-3 plasmid can be successfully expressed in a number of *E. coli* strains, such as XL-1, TB1, BL21 and BLR, using about 25 to about 100 μM IPTG for induction. Surprisingly, concentrations of about 25 to about 50 μM IPTG have been found to provide optimal results in 2 L shaker flasks and fermentors.

Expression of a contemplated chimer molecule in other microbes such as Salmonella like *S. typhi* and *S. typhimurium* and *S. typhimurium-E. coli* hybrids, yeasts such as *S. cerivisiae* or *Pichia pastoris*, in mammalian cells such as Chinese hamster ovary (CHO) cells, in both monocot and dicot plant cells generally and particularly in dicot plant storage organs such as a root, seed or fruit as where an oral vaccine or inoculum is desired, and in insect cells such as those of *S. Frugiperda* cells or Trichoplusia by use of *Autographa californica* nuclear polyhedrosis virus (AcNPV) or baculovirus are discussed in detail in published before-mentioned application WO 02/14478 A2. These modes of expression, although contemplated, will therefore not be discussed further herein.

A variety of methods have been developed to operatively link DNA to vectors via complementary cohesive termini or blunt ends. For instance, complementary homopolymer tracts can be added to the DNA segment to be inserted into the vector DNA. The vector and DNA segment are then joined by hydrogen bonding between the complementary homopolymeric tails to form recombinant DNA molecules.

Alternatively, synthetic linkers containing one or more restriction endonuclease sites can be used to join the DNA segment to the expression vector, as noted before. The synthetic linkers are attached to blunt-ended DNA segments by incubating the blunt-ended DNA segments with a large excess of synthetic linker molecules in the presence of an enzyme that is able to catalyze the ligation of blunt-ended DNA molecules, such as bacteriophage T4 DNA ligase.

Thus, the products of the reaction are DNA segments carrying synthetic linker sequences at their ends. These DNA segments are then cleaved with the appropriate restriction endonuclease and ligated into an expression vector that has been cleaved with an enzyme that produces termini compatible with those of the synthetic linker. Synthetic linkers containing a variety of restriction endonuclease sites are commercially available from a number of sources including New England BioLabs, Beverly, Mass. A desired DNA segment can also be obtained using PCR technology in which the forward and reverse primers contain desired restriction sites that can be cut after amplification so that the gene can be inserted into the vector. Alternatively PCR products can be directly cloned into vectors containing T-overhangs (Promega Corp., A3600, Madison, Wis.) as is well known in the art.

The expressed chimeric protein self-assembles into particles within the host cells, whether in single cells or in cells within a multicelled host. The particle-containing cells are harvested using standard procedures, and the cells are lysed using a French pressure cell, lysozyme, sonicator, bead beater or a microfluidizer (Microfluidics International Corp., Newton Mass.). After clarification of the lysate, particles are precipitated with 45% ammonium sulfate, resuspended in 20 mM sodium phosphate, pH 6.8 and dialyzed against the same buffer. The dialyzed material is clarified by brief centrifugation and the supernatant subjected to gel filtration chromatography using Sepharose® CL-4B. Particle-containing fractions are identified, subjected to hydroxyapatite chromatography, and reprecipitated with ammonium sulfate prior to resuspension, dialysis and sterile filtration and storage at −70° C.

HBc Chimer Conjugates

Chimeric HBc particles to which a substance has been chemically (covalently) attached also form part of the invention. Specifically, peptide sequences corresponding to HBV surface antigen can be covalently linked to the chimeric particle. Non-HBV sequences can also advantageously be conjugated to the HBc chimer. Alternatively non-peptidic compounds can be advantageously linked to the HBc chimer particle. Such non-peptidic compounds can include oligonucleotides, saccharides, immunostimulatory alkylated saccharides.

Any chemically reactive moiety (hapten) can be linked to a contemplated HBc chimer or chimer particle such as a chimer particle containing a heterologous linker residue such as a lysine, glutamic or aspartic acid, cysteine or tyrosine in the loop region of Domain II. The molecule of interest typically is a B cell immunogen, but can be a immunostimulatory molecule or a peptide sequence aimed at targeting the chimer to specific receptors or cells of the immune system. The covalently bound hapten can be a polypeptide, a protein, a oligonucleotide, a carbohydrate (saccharide; i.e., oligo- or polysaccharide), or a non-polypeptide, non-carbohydrate chemical such as 2,4-dinitrobenzene or a medicament such as cocaine or nicotine.

A HBc chimer particle conjugate so formed is useful as an inoculum or vaccine, as is discussed hereinafter. Because the chimer protein self assembles upon expression and a conjugate is formed after expression, conjugate formation is typically done using the assembled particles as compared to the free protein molecules.

Methods for operatively linking individual hapten molecules to a protein or polypeptide through an amino acid residue side chain of the protein or polypeptide to form a pendently-linked immunogenic conjugate, e.g., a branched-chain polypeptide polymer, are well known in the art, and are described in detail in PCY WO 02/14478 A2 published on Feb. 21, 2002.

Inocula and Vaccines

A before-described recombinant HBc chimer immunogen preferably in particulate form is dissolved or dispersed in an immunogenic effective amount in a pharmaceutically acceptable vehicle composition that is preferably aqueous to form an inoculum or vaccine. When administered to a host animal in which antibodies are desired to be induced or a host animal having a chronic hepatitis B virus infection and thus in need of immunization such as a mammal (e.g., a mouse, dog, goat, sheep, horse, bovine, monkey, ape, or human) or bird (e.g., a chicken, turkey, duck or goose), an inoculum induces antibodies that immunoreact with an added B cell epitope such as a Pre-S2 B cell epitope present in the immunogen. In a vaccine, those induced antibodies are also believed to immunoreact in vivo with (bind to) the virus or virally-infected cells and protect the host from influenza infection. An inoculum can induce production of activated T cells in an immunized host animal, but those activated T cells are not protective, whereas activated T cells induced by a vaccine protect the host.

Thus, a composition that is a vaccine in one animal can be an inoculum an inoculum for another host, as where the antibodies are induced in a second host that is not infected by influenza A. In the present situation, it is believed that patients that are chronic carriers of HBV are protected primarily via activated T cells.

The amount of recombinant HBc chimer immunogen utilized in each immunization is referred to as an immunogenic effective amount and can vary widely, depending inter alia, upon the recombinant HBc chimer immunogen, animal host immunized, and the presence of an adjuvant in the vaccine, as discussed below. Immunogenic effective amounts for a vaccine and an inoculum provide the protection or antibody activity, respectively, discussed hereinbefore.

Vaccines or inocula typically contain a recombinant HBc chimer immunogen concentration of about 1 microgram to about 1 milligram per inoculation (unit dose), and preferably about 10 micrograms to about 50 micrograms per unit dose. Immunizations in mice typically contain 10 or 20 µg of chimer particles.

In a preferred embodiment of the invention, the chimeric HBc particle or chimeric particle with pendently linked haptens is administered to patients chronically infected with hepatitis B virus, in a manner to induce T-cell activation. Such a treatment includes repeated administration by injection. Most preferred methods of administration include intramuscular or subcutaneous injection, but alternative preferred methods include intradermal administration. Intradermal administration can be achieved by particulate bombardment using devices such as those developed by Powderject Pharmaceuticals, Plc (Oxford, England), or can be achieved by use of a patch.

Preferred patches for administration of the immunogenic particles have multiple short protuberances measuring about 50 to about 1000 micrometers long that serve to penetrate the epidermis and provide passage of the immunogenic particles from the patch into the dermis. Activators of Langerhans cells are preferably co-administered with intradermal administration. Activators include camphor, dimethyl sulfoxide, and diphenyl phthalate. If administration is achieved by intramuscular or subcutaneous injection, the chimeric HBc molecule particles are preferably administered in presence of a Th-1 promoting adjuvant.

The patient is administered one or more doses of the chimeric particles. The dose of the particles is preferably about 10 µg to about 500 µg, and most preferably about 20

µg to about 100 µg such that enhancement of T-cell response to the hepatitis B virus is induced. The enhancement of the immune response to the virus can be measured by the T cell response and/or the B cell response. A result of a contemplated method is that either or both of these responses to HBV is enhanced in the patient as compared to the patient's initial, pretreatment response.

In some aspects of the invention, an immunization regimen can include all or portions of the HbsAg molecule, including the Pre-S1 and Pre-S2 regions. Those immunizations can be given together, separately on the same or separate days, or as a series of several immunizations of one immunogen followed by several immunizations of the other immunogen.

T cell activation can be measured by a variety of techniques. In usual practice, a host animal is inoculated with a contemplated HBc chimer particle vaccine or inoculum, and peripheral mononuclear blood cells (PMBC) are thereafter collected. Those PMBC are then cultured in vitro in the presence of the T cell immunogen for a period of about three to five days. In the case of a T-cell response to HBV the T cell immunogen can be HBsAg, HBc, or fragments thereof. The cultured PMBC are then assayed for proliferation or secretion of a cytokine such as IL-2, GM-CSF of IFN-γ. Assays for T cell activation are well known in the art. See, for example, U.S. Pat. No. 5,478,726 and the art cited therein.

B cell response is measured as antibodies. In the case of HBV, the appearance of anti-surface antigen antibodies (including pre-S1 and pre-S2 regions is indicative of an enhanced immune response.

Vaccines typically contain a recombinant HBc chimer immunogen concentration of about 1 microgram to about 1 milligram per inoculation (unit dose), and preferably about 10 micrograms to about 50 micrograms per unit dose. The term "unit dose" as it pertains to a vaccine or inoculum of the present invention refers to physically discrete units suitable as unitary dosages for animals, each unit containing a predetermined quantity of active material calculated to individually or collectively produce the desired immunogenic effect in association with the required diluent; i.e., carrier, or vehicle.

Vaccines are typically prepared from a recovered recombinant HBc chimer immunogen by dispersing the immunogen, preferably in particulate form, in a physiologically tolerable (acceptable) diluent vehicle such as water, saline phosphate-buffered saline (PBS), acetate-buffered saline (ABS), 5% mannitol solution, Ringer's solution or the like to form an aqueous composition. The diluent vehicle can also include oleaginous materials such as peanut oil, squalane or squalene as is discussed hereinafter. The vehicle can further contain immunostimulatory molecules as is discussed hereinafter.

The preparation of vaccines that contain proteinaceous materials as active ingredients is also well understood in the art. Typically, such vaccines are prepared as parenterals, either as liquid solutions or suspensions; solid forms suitable for solution in, or suspension in, liquid prior to injection can also be prepared. The preparation can also be emulsified.

The immunogenic active ingredient is often mixed with excipients that are pharmaceutically acceptable and compatible with the active ingredient. Suitable excipients are, for example, water, saline, dextrose, glycerol, ethanol, or the like and combinations thereof. In addition, if desired, an inoculum or vaccine can contain minor amounts of auxiliary substances such as wetting or emulsifying agents, pH buffering agents that enhance the immunogenic effectiveness of the composition.

A contemplated vaccine advantageously also includes an adjuvant. Suitable adjuvants for vaccines and inocula of the present invention comprise those adjuvants that are capable of enhancing the antibody responses against B cell epitopes of the chimer, as well as adjuvants capable of enhancing cell mediated responses towards T cell epitopes contained in the chimer. Adjuvants are well known in the art (see, for example, *Vaccine Design—The Subunit and Adjuvant Approach*, 1995, Pharmaceutical Biotechnology, Volume 6, Eds. Powell, M. F., and Newman, M. J., Plenum Press, New York and London, ISBN 0-306-44867-X).

Exemplary adjuvants include complete Freund's adjuvant (CFA) that is not used in humans, incomplete Freund's adjuvant (IFA), squalene, squalane and alum [e.g., Alhydrogel™ (Superfos, Denmark)], which are materials well known in the art, and are available commercially from several sources.

Preferred adjuvants for use with immunogens of the present invention include aluminum or calcium salts (for example hydroxide or phosphate salts). A particularly preferred adjuvant for use herein is an aluminum hydroxide gel such as Alhydrogel™. For aluminum hydroxide gels, the chimer protein is admixed with the adjuvant so that about 50 to about 800 micrograms of aluminum are present per dose, and preferably between 400 and 600 micrograms are present. Calcium phosphate nanoparticles (CAP) are an adjuvant being developed by Biosante, Inc (Lincolnshire, Ill.). The immunogen of interest can be either coated to the outside of particles, or encapsulated inside on the inside [He et al. (November 2000) *Clin. Diagn. Lab. Immunol.*, 7(6): 899-903].

Another particularly preferred adjuvant for use with an immunogen of the present invention is an emulsion. A contemplated emulsion can be an oil-in-water emulsion or a water-in-oil emulsion. In addition to the immunogenic chimer protein particles, such emulsions comprise an oil phase of squalene, squalane, peanut oil or the like as are well known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate and mannide mono-oleate. An immunogen-containing emulsion is administered as an emulsion.

Preferably, such emulsions are water-in-oil emulsions that comprise squalene, glycerol and a surfactant such as mannide mono-oleate (Arlacel™ A), optionally with squalane, emulsified with the chimer protein particles in an aqueous phase. The oil phase preferably comprises about 0.1 to about 10 percent of the vaccine, and more preferably about 0.2 to about 1 percent. Alternative components of the oil-phase include alpha-tocopherol, mixed-chain di- and tri-glycerides, and sorbitan esters. Well-known examples of such emulsions include Montanide™ ISA-720, and Montanide™ ISA 703 (Seppic, Castres, France), each of which is understood to contain both squalene and squalane, with squalene predominating in each, but to a lesser extent in Montanide™ ISA 703. Most preferably, Montanide™ ISA-720 is used, and a ratio of oil-to-water of 7:3 (w/w) is used. Other preferred oil-in-water emulsion adjuvants include those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. No. 4,539,205, No. 4,643,992, No.

5,011,828 and No. 5,093,318, whose disclosures are incorporated by reference. Of these materials, 7-allyl-8-oxoguanosine (loxoribine) is particularly preferred. That molecule has been shown to be particularly effective in inducing an antigen-(immunogen-) specific response.

A preferred useful adjuvant includes monophosphoryl lipid A (MPL®), 3-deacyl monophosphoryl lipid A (3D-MPL®), a well-known adjuvant manufactured by Corixa Corp. of Seattle, Wash., formerly Ribi Immunochem, Hamilton, Mont. The adjuvant contains three components extracted from bacteria: monophosphoryl lipid (MPL®) A, trehalose dimycolate (TDM) and cell wall skeleton (CWS) (MPL+TDM+CWS) in a 2 percent squalene/Tween® 80 emulsion. This adjuvant can be prepared by the methods taught in GB 2122204B. A preferred form of 3-de-O-acylated monophosphoryl lipid A is in the form of an emulsion having a small particle size less than 0.2 µm in diameter (EP 0 689 454 B1).

Most preferred are a compound structurally related to MPL® adjuvant called aminoalkyl glucosamide phosphates (AGPs) such as those available from Corixa Corp under the designation RC-529 {2-[(R)-3-tetra-decanoyloxytetradecanoylamino]-ethyl-2-deoxy-4-O-phosphono-3-O-[(R)-3-tetradecanoyloxytetra-decanoyl]-2-[(R)-3-tetra-decanoyloxytetradecanoyl-amino]-p-D-glucopyranoside triethylammonium salt}. An RC-529 adjuvant is available in a squalene emulsion sold as RC-529SE and in an aqueous formulation as RC-529AF available from Corixa Corp. (See, U.S. Pat. No. 6,355,257 and U.S. Pat. No. 6,303,347; U.S. Pat. No. 6,113,918; and U.S. Publication No. 03-0092643.)

Additional most preferred adjuvants include CpG (also ODN; oligonucleotides containing the CpG nucleotide motif one or more times plus flanking sequences) available from Coley Pharmaceutical Group; the adjuvant designated QS21 available from Aquila Biopharmaceuticals, Inc.; SBAS2 (now ASO2) available from SKB (now Glaxo-SmithKline) that contains QS21 and MPL ion an oil-in-water emulsion; the so-called muramyl dipeptide analogues described in U.S. Pat. No. 4,767,842; and MF59 available from Chiron Corp. (see, U.S. Pat. No. 5,709,879 and U.S. Pat. No. 6,086,901).

More particularly, immunologically active saponin fractions having adjuvant activity derived from the bark of the South American tree *Quillaja Saponaria Molina* (e.g. Quil™ A) are also useful. Derivatives of Quil™ A, for example QS21 (an HPLC purified fraction derivative of Quil™ A), and the method of its production is disclosed in U.S. Pat. No. 5,057,540. In addition to QS21 (also known as QA21), other fractions such as QA17 are also disclosed.

The muramyl dipeptide adjuvants include
N-acetyl-muramyl-L-threonyl-D-isoglutamine (thur-MDP), N-acetyl-nor-muramyl-L-alanyl-D-isoglutamine (CGP 11637, referred to as nor-MDP), and N-acetyl-muramyl-L-alanyl-D-isoglutaminyl-L-alanine-2-(1'-2'-dipalmityol-sn-glycero-3-hydroxyphosphoryloxy)-ethylamine (CGP) 1983A, referred to as MTP-PE).

Preferred adjuvant mixtures further include combinations of 3D-MPL and QS21 (EP 0 671 948 B1), oil-in-water emulsions comprising 3D-MPL and QS21 (WO 95/17210, PCT/EP98/05714), 3D-MPL formulated with other carriers (EP 0 689 454 B1), QS21 formulated in cholesterol-containing liposomes (WO 96/33739), or immunostimulatory oligonucleotides (WO 96/02555). Alternative adjuvants include those described in WO 99/52549 and non-particulate suspensions of polyoxyethylene ether (UK Patent Application No. 9807805.8).

The use of an adjuvant that one or both of (a) an agonist for toll-like receptor-4 (TLR-4) such as an MPL® or a structurally related compound such as an RC-529 adjuvant or a Lipid A mimetic, and (b) an agonist for toll-like receptor-9 (TLR-9) such as a non-methylated oligo deoxynucleotide-containing the CpG motif is particularly preferred. Upon admixture in a pharmaceutically acceptable diluent with the before-described immunogenic HBc-containing particles or chemically linked to such immunogenic particles and immunization of a suitable host animal such as a human chronically infected with hepatitis B virus, such adjuvants enhance the production of gamma-producing CD 8+, CD 4+ T cells and cytotoxic T lymphocytes in the immunized host. Alum also can be present in such an adjuvant mixture. Initial results indicate that alum tends to enhance the Th2 immune response that favors production of IgG1-type antibodies, whereas the RC-529-type adjuvant favors a Th1 immune response that favors production of IgG2a and IgG2b antibodies and a T cell response when a T cell immunogen is present as is the case when HBc particles comprise the immunogen.

A most preferred adjuvant mixture comprises a stable water-in-oil emulsion further containing aminoalkyl glucosamine phosphates such as described in U.S. Pat. No. 6,113,918. Of the aminoalkyl glucosamine phosphates the molecule known as RC-529 {(2-[(R)-3-tetradecanoyloxytetradecanoylamino]ethyl 2-deoxy-4-O-phosphono-3-O-[(R)-3-tetradecanoyloxy-tetradecanoyl]-2-[(R)-3-tetradecanoyloxytetra-decanoylamino]-p-D-glucopyranoside triethylammonium salt.)} is the most preferred. A preferred oil-in-water emulsion is described in U.S. Pat. No. 6,630,161

In a preferred method of use, the adjuvant and immunogen are provided in the form of a kit. The kit comprises a container of recombinantly produced immunogenic chimer particles, and a container of adjuvant. The contents of the two containers are mixed together prior to use, and preferably, immediately prior to administration to the patient. In a most preferred method of use the recombinantly produced chimer particles are provided as a lyophilized cake. The lyophilized cake is reconstituted with an aqueous formulation of the adjuvant.

Adjuvants are utilized in an adjuvant amount, which can vary with the adjuvant, mammal and recombinant HBc chimer particle immunogen. Typical amounts can vary from about 1 µg to about 1 mg per immunization. Those skilled in the art know that appropriate concentrations or amounts can be readily determined.

A vaccine is typically formulated for parenteral administration. Exemplary immunizations are carried out sub-cutaneously (SC) intra-muscularly (IM), intravenously (IV), intraperitoneally (IP) or intra-dermally (ID). Additional formulations that are suitable for other modes of administration include suppositories and, in some cases, oral formulation. The use of a nasal spray for inoculation is also contemplated as discussed in Neirynck et al. (October 1999) *Nature Med.*, 5(10):1157-1163. For suppositories, traditional binders and carriers can include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like.

A vaccine composition takes the form of a solution, suspension, tablet, pill, capsule, sustained release formulation or powder, and contains an immunogenic effective amount of HBc chimer or HBc chimer conjugate, preferably as particles, as active ingredient. In a typical composition, an immunogenic effective amount of preferred HBc chimer or HBc chimer conjugate particles is about 1 µg to about 1 mg of active ingredient per dose, and more preferably about 5 µg to about 50 µg per dose, as noted before.

The HBc chimer particles and HBc chimer particle conjugates can be formulated into the vaccine as neutral or salt forms. Pharmaceutically acceptable salts, include the acid addition salts (formed with the free amino groups of the protein or hapten) and are formed with inorganic acids such as, for example, hydrochloric or phosphoric acids, or such organic acids as acetic, oxalic, tartaric, mandelic, and the like. Salts formed with the free carboxyl groups can also be derived form inorganic bases such as, for example, sodium, potassium, ammonium, calcium, or ferric hydroxides, and such organic bases as isopropylamine, trimethylamine, 2-ethylamino ethanol, histidine, procaine, and the like.

In yet another embodiment, a vaccine or inoculum is contemplated in which a gene encoding a contemplated HBc chimer is transfected into suitably attenuated enteric bacteria such as *S. typhi*, *S. typhimurium*, *S. typhimurium-E. coli* hybrids or *E. coli*. Exemplary attenuated or avirulent *S. typhi* and *S. typhimurium* and *S. typhimurium-E. coli* hybrids are discussed in the citations provided before. These vaccines and inocula are particularly contemplated for use against diseases that infect or are transmitted via mucosa of the nose, the gut and reproductive tract such as influenza, yeasts such as *Aspergiullus* and *Candida*, viruses such as polio, moot-and-mouth disease, hepatitis A, and bacteria such as *Cholera*, *Salmonella* and *E. coli* and where a mucosal IgA response is desired in addition to or instead of an IgG systemic response.

The enteric bacteria can be freeze dried, mixed with dry pharmaceutically acceptable diluents, made into tablets or capsules for ingestion and administered to or taken by the host animal as are usual solid phase medications. In addition, aqueous preparations of these bacterial vaccines are adapted for use in mucosal immunization as by oral, nasal, rectal or vaginal administration.

Oral immunization using plant matter containing contemplated chimeric molecule particles can be achieved by simple ingestion of the transgenic plant tissue such as a root like a carrot or seed such as rice or corn. In this case, the water of the mouth or gastrointestinal tract provides the usually used aqueous medium used for immunization and the surrounding plant tissue provides the pharmaceutically acceptable diluent.

The vaccines are administered in a manner compatible with the dosage formulation, and in such amount as are therapeutically effective and immunogenic. The quantity to be administered depends on the subject to be treated, capacity of the subject's immune system to synthesize antibodies, and degree of protection desired. Precise amounts of active ingredient required to be administered depend on the judgment of the practitioner and are peculiar to each individual. However, suitable dosage ranges are of the order of tens of micrograms active ingredient per individual. Suitable regimes for initial administration and booster shots are also variable, but are typified by an initial administration followed in intervals (weeks or months) by a subsequent injection or other administration.

It is noted that an alternative method of inducing a therapeutic immune response in HBV-infected individuals is to administer the immunogenic chimer particles to the patient's dendritic cells ex-vivo and to then re-administer the dendritic cells to the patient. Methods for isolating dendritic cells from the body and culturing them in the presence of antigen are well known in the art [Nestle et al (2001) *Nature Medicine* 7, 761-765 and citations therein].

Another aspect of the present invention is therefore a method for inducing a T cell response to HBc in patients chronically infected with HBV. That method comprises the steps of isolating dendritic cells from a patient's body, contacting the dendritic cells with immunogenic chimer particles and maintaining the contact to form activated dendritic cells, optionally stimulating the dendritic cells with a cytokine such as GMCSF, and then administering the activated dendritic cells to the patient.

The invention is illustrated by the following non-limiting examples.

EXAMPLE 1

B Cell Epitope-Containing Chimer Preparation

A. Preparation of plasmid vector pKK223-3N, a modified form of pKK223-3

Plasmid vector pKK223-3 (Pharmacia) was modified by the establishment of a unique NcoI restriction site to enable insertion of HBc genes as NcoI-HindIII restriction fragments and subsequent expression in *E. coli* host cells. To modify the pKK223-3 plasmid vector, a new SphI-HindIII fragment was prepared using the PCR primers pKK223-3/433-452-F and pKK223-NcoI-mod-R, and pKK223-3 as the template. This PCR fragment was cut with the restriction enzymes SphI and HindIII to provide a 467 bp fragment that was then ligated with a 4106 bp fragment of the pKK223-3 vector, to effectively replace the original 480 bp SphI-HindIII fragment. The resultant plasmid (pKK223-3N) is therefore 13 bp shorter than the parent plasmid and contains modified nucleotide sequence upstream of the introduced NcoI site (see FIG. 1 in which the dashes indicate the absent bases). The final plasmid, pKK223-3N, has a size of 4573 bp. Restriction sites in plasmid pKK223-3N are indicated in FIG. 1, and the nucleotide changes made to pKK223-3 to form plasmid pKK223-3N are indicated by an underline as shown below.

| | | |
|---|---|---|
| pKK223-3/433-452-F | GGTGCATGCAAGGAGATG | SEQ ID NO: 208 |
| pKK223-NcoI-mod-R | GCGAAGCTTCGGATC<u>ccatgg</u>TTTTTTCCTCCTTATGTGAAATTGTTATCCG-CTC | SEQ ID NO: 209 |

B. Preparation of V1 and V2 Cloning Vectors

Modified HBc149 genes, able to accept the directional insertion of synthetic dsDNA fragments into the immunodominant loop region, were constructed using PCR. [The plasmid accepting inserts between amino acids E77 and D78 was named V1, whereas the plasmid accepting inserts between D78 and P79 was named V2.] The HBc149 gene was amplified in two halves using two PCR primer pairs, one of which amplifies the amino terminus, the other amplifies the carboxyl terminus. For V1, the products of the PCR reactions (N- and C-terminus) are both 246 bp fragments; for V2, the products are a 249 bp (N-terminus) and a 243 bp fragment (C-terminus).

The N-terminal fragments prepared were digested with NcoI and EcoRI, and the C-terminal fragments were digested with EcoRI and HindIII. The V1 and V2 fragments pairs were then ligated together at the common EcoRI overhangs. The resultant NcoI-HindIII fragments were then ligated into the pKK223-3N vector, which had been prepared by digestion with NcoI and HindIII.

To insert B cell epitopes into the V1 and V2 plasmids, the plasmids were digested with EcoRI and SacI restriction enzymes. Synthetic dsDNA fragments containing 5' EcoRI and 3' SacI overhangs were then inserted. In both cases, V1 and V2, glycine-isoleucine (EcoRI) and glutamic acid-leucine (SacI) amino acid pairs, coded for by the restriction sites, flank the inserted B cell epitopes. The inserted restriction sites are underlined in the primers below.

Two expression vectors [V2.Pf1 (N-MGCELDP) and V2.Pf1 (N-MGCDIDP)] are prepared to determine the ability of N-terminal cysteine residues to stabilize chimer particles. To make the vector V2.Pf1 (N-MGCELDP), the oligonucleotides HBc (MGCELDP)-NcoI-F and HBc149/HindIII-R are used to amplify the hybrid HBc gene from vector V2.Pf1. The resultant 528 bp fragment is cleaved with NcoI and HindIII and inserted into pKK-223-3N, which had been cleaved with the same two enzymes.

To make the vector V2.Pf1 (N-MGCDIDP) the oligonucleotides HBc (MGCDIDP)-NcoI-F and HBc149/HindIII-R are used to amplify the hybrid HBc gene from vector

V1

HBc149/NcoI-F

5'-TTGGGCCATGGACATCGACCCTTA        SEQ ID NO: 210

HBc-E77/EcoRI-R

5'-GCGGAATTCCTTCCAAATTAACACCCACC    SEQ ID NO: 211

HBc-D78/EcoRI-SacI-F

5'-CGCGAATTCAAAAGAGCTCGATCCAGCGTCTAGAGAC    SEQ ID NO: 212

HBc149/HindIII-R

5'-CGCAAGCTTAAACAACAGTAGTCTCCGGAAG    SEQ ID NO: 213

V2

HBc149/NcoI-F

5'-TTGGGCCATGGACATCGACCCTTA        SEQ ID NO: 210

HBc-D78/EcoRI-R

5'-GCGGAATTCCATCTTCCAAATTAACACCCAC    SEQ ID NO: 214

HBc-P79/EcoRI-SacI-F

5'-CGCGAATTCAAAAGAGCTCCCAGCGTCTAGAGACCTAG    SEQ ID NO: 215

HBc149/HindIII-R

5'-CGCAAGCTTAAACAACAGTAGTCTCCGGAAG    SEQ ID NO: 213

Vectors to Express Chimer Particles Containing an N-Terminal Cysteine and the CS-Repeat Epitopes from *P. Falciparum* in the Immunodominant Loop V2.Pf1. The resultant 528 bp fragment is cleaved with NcoI and HindIII and inserted into pKK-223-3N, which has been cleaved with the same two enzymes.

HBc (MGCELDP)-NcoI-F

M  G  C  E  L  D  P  Y  K  E  F  G    SEQ ID NO: 216

5'-GCGCCATGGGGTGTGAGCTCGACCCTTATAAAGAATTTGG    SEQ ID NO: 217

HBc (MGCDIDP)-NcoI-F

M  G  C  D  I  D  P  Y  K  E  F  G    SEQ ID NO: 218

5'-GCGCCATGGGGTGTGACATCGACCCTTATAAAGAATTTGG    SEQ ID NO: 219

C. Preparation of V7 Cloning Vector

To enable the fusion of T cell epitopes to the C terminus of a HBc chimer, a new vector, V7, was constructed. Unique EcoRI and SacI restriction sites were inserted between valine-149 and the HindIII site to facilitate directional insertion of synthetic dsDNAs into EcoRI-HindIII (or EcoRI-SacI) restriction sites. The pair of PCR primers below was used to amplify the HBc 149 gene with a NcoI restriction site at the amino-terminus and EcoRI, SacI and HindIII sites at the carboxyl-terminus. The product of the PCR reaction (479 bp) was digested with NcoI/HindIII and cloned into pKK223-3N to form V7.

To insert T cell epitopes, the plasmid (V7) was digested EcoRI/HindIII (or EcoRI-SacI) and synthetic dsDNA fragments having EcoRI/HindIII (or EcoRI/SacI) overhangs, were ligated into V7. For all V7 constructs, the final amino acid of native HBc (valine-149) and the first amino acid of the inserted T cell epitope are separated by a glycine-isoleucine dipeptide sequence coded for by the nucleotides that form the EcoRI restriction site. For epitopes inserted at EcoRI/SacI, there are additional glutamic acid-leucine residues after the T cell epitope, prior to the termination codon, contributed by the SacI site. Restriction sites are again underlined in the primers shown.

```
HBc149/NcoI-F
5'-TTGGGCCATGGACATCGACCCTTA                          SEQ ID NO: 210

HBc149/SacI-EcoRI-H3-R
5'-CGCAAGCTTAGAGCTCTTGAATTCCAACAACAGTAGTCTCCG        SEQ ID NO: 220
```

D. Preparation of V12 Expression Constructs

V12 vectors, which contain B cell epitopes between amino acids 78 and 79, as well as T cell epitopes downstream of valine-149, are constructed from V2 and V7 vectors. The carboxyl terminus of a V7 vector containing a T cell epitope inserted at EcoRI/HindIII is amplified using two PCR primers (HBc-P79/SacI-F and pKK223-2/4515-32R) to provide a dsDNA fragment corresponding to amino acids 79-149 plus the T cell epitope, flanked with SacI and HindIII restriction sites.

The PCR products are cut with SacI and HindIII and then cloned into the desired V2 vector prepared by cutting with the same two enzymes. The PCR primers are amenable for the amplification of the carboxyl terminus of all V7 genes, irrespective of the T cell epitope present after amino acid 149 of the HBc gene.

One exception to the generality of this approach was in the preparation of the V12 constructs containing the Pf-CS (C17A) mutation, which were prepared from existing V12 constructs. In this case, V12 constructs were amplified with HBc149/NcoI-F (SEQ ID NO: 180) and the mis-match reverse PCR primer (SEQ ID NO: 292), which facilitated the C17A mutation. The resultant PCR product was digested with NcoI and HindIII and cloned back into pKK223-3N (previously cut with the same enzymes). Restriction sites are underlined.

```
HBc-P79/SacI-F      5'-CGCGAGCTCCCAGCGTCTAGAGACCTAG   SEQ ID NO: 221 pKK223-2/4515-32R   5'-GTATCAGGCTGAAAATC              SEQ ID NO: 222
```

E. *P. Falciparum* CS-repeat B cell Epitopes Inserted into V2

For V2 and V7 constructs, synthetic dsDNA fragments coding for the B (V2) or T cell epitope (V7) of interest are inserted into EcoRI/SacI restriction sites. Synthetic dsDNA fragments, encoding B and T cell epitopes of interest, are prepared by mixing complementary single stranded DNA oligonucleotides at equimolar concentrations, heating to 95° C. for 5 minutes, and then cooling to room temperature at a rate of −1° C. per minute. This annealing reaction is performed in TE buffer. The double-stranded DNAs are shown below with the encoded epitope sequence shown above. The pound symbol, #, is used in some of the amino acid residue sequences that follow to indicate the presence of a stop codon.

```
Pf1
   I  N  A  N  P  N  A  N  P  N  A  N  P  N  A
AATTAACGCTAATCCGAACGCTAATCCGAACGCTA
    TTGCGATTAGGCTTGCGATTAGGCTTGCGATTAGGCTTGCGAT
        N  P  E  L                         SEQ ID NO: 223
        ATCCGGAGCT                          SEQ ID NO: 224
          TAGGCC                            SEQ ID NO: 225
Pf3
   I  N  A  N  P  N  V  D  P  N  A  N  P  N  A  N  P
AATTAACGCTAATCCGAACGTTGACCCGAACGCTAATCCGAACGCTAATCCGA
    TTGCGATTAGGCTTGCAACTGGGCTTGCGATTAGGCTTGCGATTAGGCT
N  A  N  P  N  V  D  P  N  A  N  P  E  L       SEQ ID NO: 226
ACGCTAATCCGAACGTTGACCCGAACGCTAATCCGGAGCT        SEQ ID NO: 227
TGCGATTAGGCTTGCAACTGGGCTTGCGATTAGGCCTCGAGG      SEQ ID NO: 228
Pf3.1
   I  N  A  N  P  N  V  D  P  N  A  N  P  N  A  N  P
AATTAACGCGAATCCGAACGTGGATCCGAATGCCAACCCTAACGCCAACCC
    TTGCGCTTAGGCTTGCACCTAGGCTTACGGTTGGGATTGCGGTTGGG
          N  A  N  P  E  L                     SEQ ID NO: 229
          AAATGCGAACCCAGAGCT                   SEQ ID NO: 230
            TTTACGCTTGGGTC                     SEQ ID NO: 231
Pf3.2
   I  N  A  N  P  N  A  N  P  N  A  N  P  N  V  D  P
AATTAACGCGAATCCGAATGCCAACCCTAACGCCAACCCAAACGTGGATCCGA
    TTGCGCTTAGGCTTACGGTTGGGATTGCGGTTGGGTTTGCACCTAGGCT
        N  A  N  P  E  L                       SEQ ID NO: 232
        ATGCGAACCCAGAGCT                       SEQ ID NO: 233
          TACGCTTGGGTC                         SEQ ID NO: 234
Pf3.3
   I  N  A  N  P  N  V  D  P  N  A  N  P  N  A  N  P
AATTAACGCGAATCCGAACGTGGATCCAAATGCCAACCCTAACGCTAATCCAA
    TTGCGCTTAGGCTTGCACCTAGGTTTACGGTTGGGATTGCGATTAGGTT
N  A  N  P  N  V  D  P  N  A  N  P  E  L       SEQ ID NO: 235
ACGCCAACCCGAATGTTGACCCCAATGCCAATCCGGAGCT        SEQ ID NO: 236
TGCGGTTGGGCTTACAACTGGGGTTACGGTTAGGCC            SEQ ID NO: 237
Pf3.4
   I  N  P  N  V  D  P  N  A  N  P  N  A  N  P  N  A
AATTAATCCGAACGTGGATCCAAATGCCAACCCTAACGCTAATCCAAACGCCA
    TTAGGCTTGCACCTAGGTTTACGGTTGGGATTGCGATTAGGTTTGCGGT
          N  P  N  V  E  L                     SEQ ID NO: 238
```

```
            ACCCGAATGTTGAGCT                  SEQ ID NO: 239

TGGGCTTACAAC                      SEQ ID NO: 240

Pf3.5

I  N  P  N  V  D  P  N  A  N  P  N  A  N  P  N  A
AATTAATCCGAACGTGGATCCAAATGCCAACCCTAACGCTAATCCAAACGCCA
      TTAGGCTTGCACCTAGGTTTACGGTTGGGATTGCGATTAGGTTTGCGGT

N  P  N  V  D  P  E  L            SEQ ID NO: 241

ACCCGAATGTTGACCCTGAGCT            SEQ ID NO: 242

TGGGCTTACAACTGGGAC                SEQ ID NO: 243

Pf3.6

I  N  P  N  V  D  P  N  A  N  P  N  A  N  P  N  A
AATTAATCCGAACGTGGATCCAAATGCCAACCCTAACGCTAATCCAAACGCCA
      TTAGGCTTGCACCTAGGTTTACGGTTGGGATTGCGATTAGGTTTGCGGT

N  P  N  V  D  P  N  A  E  L      SEQ ID NO: 244

CCCGAATGTTGACCCTAATGCTGAGCT       SEQ ID NO: 245

TGGGCTTACAACTGGGATTACGAC          SEQ ID NO: 246

Pf3.7

I  N  V  D  P  N  A  N  P  N  A  N  P  N  A  N  P
AATTAACGTGGATCCAAATGCCAACCCTAACGCTAATCCAAACGCCAACCCGA
      TTGCACCTAGGTTTACGGTTGGGATTGCGATTAGGTTTGCGGTTGGGCT

N  V  E  L                        SEQ ID NO: 247

ATGTTGAGCT                        SEQ ID NO: 248

TACAAC                            SEQ ID NO: 249

Pf3.8

I  N  V  D  P  N  A  N  P  N  A  N  P  N  A  N  P
AATTAACGTGGATCCAAATGCCAACCCTAACGCTAATCCAAACGCCAACCCGA
      TTGCACCTAGGTTTACGGTTGGGATTGCGATTAGGTTTGCGGTTGGGCT

N  V  D  P  E  L                  SEQ ID NO: 250

ATGTTGACCCTGAGCT                  SEQ ID NO: 251

TACAACTGGGAC                      SEQ ID NO: 252

Pf3.9

I  N  V  D  P  N  A  N  P  N  A  N  P  N  A  N  P
AATTAACGTGGATCCAAATGCCAACCCTAACGCTAATCCAAACGCCAACCCGA
      TTGCACCTAGGTTTACGGTTGGGATTGCGATTAGGTTTGCGGTTGGGCT

N  V  D  P  N  A  E  L            SEQ ID NO: 253

ATGTTGACCCTAATGCTGAGCT            SEQ ID NO: 254

TACAACTGGGATTACGAC                SEQ ID NO: 255

Pf3.10

I  D  P  N  A  N  P  N  A  N  P  N  A  N  P
AATTGATCCAAATGCCAACCCTAACGCTAATCCAAACGCCAACC
```

```
                          -continued
   CTAGGTTTACGGTTGGGATTGCGATTAGGTTTGCGGTTGG

N   V   E   L                           SEQ ID NO: 256

CGAATGTTGAGCT                        SEQ ID NO: 257

GCTTACAAC                            SEQ ID NO: 258

Pf3.11

I   D   P   N   A   N   P   N   A   N   P   N   A   N   P   N   V

AATTGATCCAAATGCCAACCCTAACGCTAATCCAAACGCCAACCCGAATGTTG

CTAGGTTTACGGTTGGGATTGCGATTAGGTTTGCGGTTGGGCTTACAAC

D   P   E   L                           SEQ ID NO: 259

ACCCTGAGCT                           SEQ ID NO: 260

TGGGAC                               SEQ ID NO: 261

Pf3.12

I   D   P   N   A   N   P   N   A   N   P   N   A   N   P   N   V

AATTGATCCAATGCCAACCCTAACGCTAATCCAAACGCCAACCCGAATGTTG

CTAGGTTTACGGTTGGGATTGCGATTAGGTTTGCGGTTGGGCTTACAAC

D   P   N   A   E   L                   SEQ ID NO: 262

ACCCTAATGCCGAGCT                     SEQ ID NO: 263

TGGGATTACGGC                         SEQ ID NO: 264

F. P. falciparum universal T cell epitope

Pf-UTC (PF/CS326-345)

I   E   Y   L   N   K   I   Q   N   S   L   S   T   E   W   S   P

AATTGAATATCTGAACAAAATCCAGAACTCTCTGTCCACCGAATGGTCTCCGT

CTTATAGACTTGTTTTAGGTCTTGAGAGACAGGTGGCTTACCAGAGGCA

C   S   V   T   #   #                   SEQ ID NO: 265

GCTCCGTTACCTAGTA                     SEQ ID NO: 266

CGAGGCAATGGATCATTCGA                 SEQ ID NO: 267

P. vivax CS-repeat B cell epitopes

Pv-T1A

I   P   A   G   D   R   A   D   G   Q   P   A   G   D   R   A   A

AATTCCGGCTGGTGACCGTGCAGATGGCCAGCCAGCGGGTGACCGCGCTGCAG

GGCCGACCACTGGCACGTCTACCGGTCGGTCGCCCACTGGCGCGACGTC

G   Q   P   A   G   E   L                SEQ ID NO: 268

GCCAGCCGGCTGGCGAGCT                  SEQ ID NO: 269

CGGTCGGCCGACCGC                      SEQ ID NO: 270

Pv-T1B

I   D   R   A   A   G   Q   P   A   G   D   R   A   D   G   Q   P

AATTGACAGAGCAGCCGGACAACCAGCAGGCGATCGAGCAGACGGACAGCCCG

CTGTCTCGTCGGCCTGTTGGTCGTCCGCTAGCTCGTCTGCCTGTCGGGC

A   G   E   L                           SEQ ID NO: 271

CAGGGGAGCT                           SEQ ID NO: 272
```

```
                                -continued
            GTCCCC                                          SEQ ID NO: 273

Pv-T2A

I   A   N   G   A   G   N   Q   P   G   A   N   G   A   G   D   Q
AATTGCGAACGGCGCCGGTAATCAGCCGGGGGCAAACGGCGCGGGTGATCAAC
        CGCTTGCCGCGGCCATTAGTCGGCCCCCGTTTGCCGCGCCCACTAGTTG
            P   G   E   L                                   SEQ ID NO: 274
            CAGGGGAGCT                                      SEQ ID NO: 275
            GTCCCC                                          SEQ ID NO: 276

Pv-T2B

I   A   N   G   A   D   N   Q   P   G   A   N   G   A   D   D   Q
AATTGCGAACGGCGCCGATAATCAGCCGGGTGCAAACGGGGCGGATGACCAAC
        CGCTTGCCGCGGCTATTAGTCGGCCCACGTTTGCCCCGCCTACTGGTTG
            P   G   E   L                                   SEQ ID NO: 277
            CAGGCGAGCT                                      SEQ ID NO: 278
            GTCCGC                                          SEQ ID NO: 279

Pv-T2C

I   A   N   G   A   G   N   Q   P   G   A   N   G   A   G   D   Q
AATTGCGAACGGCGCCGGTAATCAGCCGGGAGCAAACGGCGCGGGGGATCAAC
        CGCTTGCCGCGGCCATTAGTCGGCCCTCGTTTGCCGCGCCCCCTAGTTG
P   G   A   N   G   A   D   N   Q   P   G   A   N   G   A   D   D
CAGGCGCCAATGGTGCAGACAACCAGCCTGGGGCGAATGGAGCCGATGACC
GTCCGCGGTTACCACGTCTGTTGGTCGGACCCCGCTTACCTCGGCTACTGG
            Q   P   G   E   L                               SEQ ID NO: 280
            AACCCGGCGAGCT                                   SEQ ID NO: 281
            TTGGGCCGC                                       SEQ ID NO: 282

PV-T3

I   A   P   G   A   N   Q   E   G   G   A   A   A   P   G   A   N
AATTGCGCCGGGCGCCAACCAGGAAGGTGGGGCTGCAGCGCCAGGAGCCAATC
        CGCGGCCCGCGGTTGGTCCTTCCACCCCGACGTCGCGGTCCTCGGTTAG
            Q   E   G   G   A   A   E   L                   SEQ ID NO: 283
            AAGAAGGCGGTGCAGCGGAGCT                          SEQ ID NO: 284
            TTCTTCCGCCACGTCGCC                              SEQ ID NO: 285
```

EXAMPLE 2

Assay Procedures

A. Antigenicity

1. Particle ELISA

Purified particles were diluted to a concentration of 10 µg/mL in coating buffer (50 mM sodium bicarbonate, pH 9.6) and coated onto the wells of ELISA strips (50 µL/well). The ELISA strips are incubated at room temperature overnight (about 18 hours). Next morning the wells are washed with ELISA wash buffer [phosphate buffered saline (PBS), pH 7.4, 0.05% Tween®-20] and blocked with 3% BSA in PBS for 1 hour (75 µL/well). ELISA strips are stored, dry, at −20° C. until needed.

To determine the antigenicity of particles, antisera are diluted using 1% BSA in PBS and 50 µL/well added to antigen-coated ELISA wells. Sera are incubated for 1 hour, washed with ELISA wash buffer and probed using an anti-mouse (IgG)-HRP (The Binding Site, San Diego, Calif.; HRP=horseradish peroxidase) conjugate (50 µL/well) or other appropriate antibody for 30 minutes. After washing with ELISA wash buffer the reaction is visualized by the addition of TM blue substrate (50 µL/well). After 10 minutes, the reaction is stopped by the addition of 1N $H_2SO_4$ (100 μL/well) and is read on an ELISA plate reader set at 450 nm.

2. Synthetic Peptide ELISA

A 20 amino acid residue synthetic peptide $(NANP)_5$ is diluted to a concentration of 2 μg/mL in coating buffer (50 mM sodium bicarbonate, pH 9.6) and coated onto the wells of ELISA strips (50 μL/well). Peptides are dried onto the wells by incubating overnight (about 18 hours), in a hood with the exhaust on. Next morning, the wells are washed with ELISA wash buffer (phosphate buffered saline, pH 7.4, 0.05% Tween®-20) and blocked with 3% BSA in PBS (75 μL/well) for 1 hour. ELISA strips are stored, dry, at −20° C. until needed.

To determine antibody antigenicity of particles, antisera (monoclonal or polyclonal) are diluted using 1% BSA in PBS, and 50 μL/well are added to antigen-coated ELISA wells. Sera are incubated for 1 hour, washed with ELISA wash buffer, and probed using an anti-mouse (IgG)-HRP conjugate (as above at 50 μL/well) or other appropriate antibody for 30 minutes, washed again with ELISA wash buffer, and then visualized by the addition of TM blue substrate (50 μL/well). After 10 minutes, the reaction is stopped by the addition of 1N $H_2SO_4$ (100 μL/well) and read on an ELISA plate reader set at 450 nm.

B. Immunogenicity of Particles

To assay the immunogenicity of particles, mice are immunized, IP, with 20 μg of particles in Freund's complete adjuvant, and then boosted at 4 weeks with 10 μg in Freund's incomplete adjuvant. Mice are bled at 2, 4, 6, and 8 weeks.

C. Thermal Stability Protocol

Purified particles are diluted to a concentration of 1 mg/mL using 50 mM $NaPO_4$, pH 6.8 and sodium azide is added to a final concentration of 0.02% to prevent bacterial growth. Particles are incubated at 37° C. and aliquots are taken at a desired time point. Samples are mixed with SDS-PAGE sample buffer (reducing) and run on 15% SDS-PAGE gels. Gels are stained using Coomassie Blue, and then analyzed.

D: Analytical Gel Filtration Analysis of Hybrid particles

Analytical gel filtration analysis of purified hybrid HBc particles is performed using a 25 mL Superose® 6 HR 10/30 chromatographic column (Amersham Pharmacia # 17-0537-01) and a BioCAD™ SPRINT Perfusion Chromatography System. The UV detector is set to monitor both wavelengths of 260 and 280 nm. The column is equilibrated with 3 column volumes (CV; about 75 mL) of buffer (50 mM $NaPO_4$, pH 6.8) at a flow rate of 0.75 mL/minute.

The particles to be analyzed are diluted to a concentration of 1 mg/mL using 50 mM $NaPO_4$, pH 6.8. 200 Microliters (μL) of the sample are then loaded onto a 200 μL loop and injected onto the column. The sample is eluted from the column with 50 mM $NaPO_4$, pH 6.8 at a flow rate of 0.75 mL/minute. Integration of the 280 nm trace was carried out using BioCAD™ software (PerSeptive™) to provide the results.

EXAMPLE 3

Determination of 280:260 Absorbance Ratios

Protein samples are diluted to a concentration of between 0.1 and 0.3 mg/mL using phosphate buffered saline (PBS), pH 7.4. The spectrophotometer is blanked, using PBS, and the absorbance of the protein sample is measured at wavelengths of 260 nm and 280 nm. The absorbance value determined for a sample at 280 nm is then divided by the absorbance value determined for the same sample at 260 nm to achieve the 280:260 absorbance ratio for a given sample. The ratios were obtained for several samples, including native particles (HBc183), HBc particles truncated after residue position 149 (HBc149), and several HBc chimers that are identified elsewhere herein, are shown below in Table 8. Full length particles ICC-1559 are a preparation of the particles first reported in Neirynck et al., (October 1999) Nature Med., 5(10):1157-1163, whereas full length particles ICC-1607 are similar particles in which the M2 polypeptide cysteines at polypeptide positions 17 and 19, ($X_{17}$ and $X_{19}$ of SEQ ID NO:9) were mutated to serine residues.

TABLE 8

| Particle Number | Full Length, (F) or C-Terminal Truncated, (T) | 280:260 Absorbance Ratio |
| --- | --- | --- |
| HBc183 | F | 0.84 |
| ICC-1532 | | |
| HBc149 | T | 1.59 |
| ICC-1438 | T | 1.57 |
| ICC-1473 | T | 1.64 |
| ICC-1475 | T | 1.04 |
| ICC-1492 | T | 1.33 |
| ICC-1559 | F | 0.68 |
| ICC-1560 | T | 1.36 |
| ICC-1590 | T | 1.51 |
| ICC-1603 | T | 1.68 |
| ICC-1604 | T | 1.40 |
| ICC-1605 | T | 1.26 |
| ICC-1607 | F | 0.73 |
| ICC-1600 | T | 1.23 |
| ICC-1601 | T | 1.12 |
| ICC-1634 | T | 0.92 |
| ICC-1632 | T | 0.96 |
| ICC-1642 | T | Not Done |
| ICC-1643 | T | 0.77 |

Example 4

Cysteine at the C-Terminus of Truncated HBc Particle

A. Addition of a Cysteine Residue to the C-terminus of Hybrid HBc Particles

Using the polymerase chain reaction (PCR), genes expressing hybrid HBc particles can be easily mutated to introduce a cysteine or cysteine-containing peptide to the C-terminus of an HBc chimer that contains an added cysteine at the N-terminus. For example, a PCR oligonucleotide primer that encodes SEQ ID NO:287 can be used, in concert with a suitable second primer, to amplify a hybrid HBc gene and incorporate a cysteine codon between codon V149 and the stop codon. An exemplary construct is that referred to as ICC-1492 that is discussed hereinafter. See also, the preparation of V2.Pf1 [N-M2(17-24/C19S)] that is discussed hereinafter.

Hepatitis B core particles can be truncated from 183 (or 185, depending on viral subtype) to 140 and retain the ability to assemble into particulate virus-like particles. Many groups have used particles truncated to amino acid 149 because amino acid 150 represents the first arginine residue of the arginine-rich C-terminal domain.

EXAMPLE 5

Influenza M2 Constructs

Recently, Neirynck et al., (October 1999) *Nature Med.*, 5(10):1157-1163 and WO 99/07839 reported the fusion of the 24 amino acid extracellular domain of M2 to the N-terminus of full-length HBc particles (HBc183), lacking amino acid residues 1-4. A schematic representation of that construct referred to herein as IM2HBc is shown below in which the 24-mer is linked to the N-terminus of HBc.

```
IM2HBc   MSLLTEVETPIRNEWGCRCNDSSD-HBc (5-183)  SEQ ID NO: 286
```

In one illustrative preparation, the M2 epitope was inserted into the immunodominant loop of hepatitis B core and particles referred to as ICC-1475 were successfully expressed and purified using techniques discussed previously for such insertions and purifications. A mutated version of the M2 epitope, in which two cysteine residues at M2 native positions 17 and 19 were substituted by alanine residues, was also expressed in the immunodominant loop (ICC-1473 particles) and the resulting particles purified. These two particles are illustrated schematically below.

```
ICC-1475 HBc(1-78)-GI-SLLTEVETPIRNEWGCRCNDSSD-EL-HBc(79-149)     SEQ ID NO: 287

ICC-1473 HBc(1-78)-GI-SLLTEVETPIRNEWGARANDSSD-EL-HBc(79-149)-C   SEQ ID NO: 288
```

The ICC-1473 particle construct yielded approximately 7-fold more purified particles when compared with the native sequence (ICC-1475). It remains to be determined if the mutation of the cysteine residues alters protective potential of the particles. However, epitopes delivered on the immunodominant loops of HBc are usually significantly more immunogenic as compared to when they are fused to other regions (including the N-terminus), and resulting particles exhibit reduced anti-HBc immunogenicity.

Particles have also been prepared in which the M2 N-terminal 24-mer epitope was fused to the N-terminus of C-terminal truncated hepatitis B core particles. That construct (ICC-1438) also contained the N-terminal pre-core sequence (SEQ ID NO:289). A similar construct was prepared that contained a single cysteine residue at the end of the hybrid protein (ICC-1492), in this case immediately after Val-149 of the HBc gene. These constructs are shown schematically below.

Residues contributed by EcoRI (GI) and SacI (EL) restriction sites are underlined. The pre-core sequence is recited between the underlined EL residues and "-HBc (2-149)".

Figure 10:
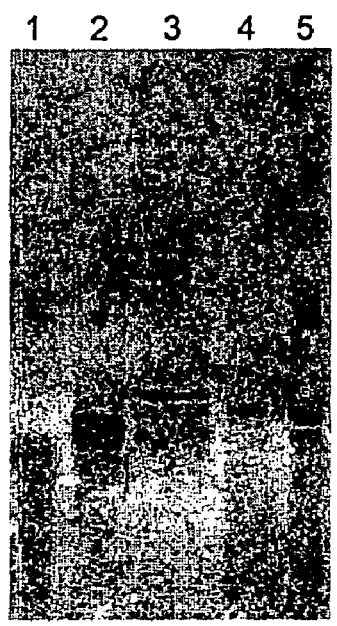
FIG. 10 is a photograph of an SDS-PAGE analysis under reducing conditions following particle preparation that shows the ICC-1438 monomer construct was unstable after aging (Lane 2) as compared to the ICC-1492 construct (Lane 3), with HBc-149 (Lane 1), ICC-1475 (Lane 4) and ICC-1473 (Lane 5) serving as additional molecular weight controls.

Analysis by SDS-PAGE as discussed elsewhere herein, showed that upon preparation, the ICC-1438 monomer construct was unstable (Lane 2) as compared to the ICC-1492 (Lane 3), with HBc-149 (Lane 1), ICC-1475 (Lane 4) and ICC-1473 (Lane 5) serving as additional molecular weight controls on the SDS-PAGE gel in FIG. 10. The instability of the ICC-1438 monomers was not evident using analytical gel filtration of particles.

Both ICC-1475 (FIG. 10, lane 4) and ICC-1473 (FIG. 10, lane 5) were expected to have slightly lower molecular weights than ICC-1438 and ICC-1492, because the former two contain the M2 epitope inserted directly into the immunodominant loop and therefore lack the pre-core sequence (SEQ ID NO:259) present in ICC-1438 and ICC-1498. As expected, ICC-1492 was larger than ICC-1475 and ICC-1473; however, ICC-1438, which is identical to ICC-1492 save the C-terminal cysteine residue, is clearly not larger than ICC-1475 and ICC-1473 due to an apparent cleavage.

A construct containing a M2 N-terminal extracellular sequence as discussed before linked to the HBc N-terminus (Domain I) or loop (Domain II) and also containing a cysteine residue at the C-terminus (Domain IV) of HBc is also contemplated.

To modify the amino-terminus of hybrid HBc particles containing immunodominant loop fusions to incorporate a cysteine residue, and minimal M2-derived sequence, a series of synthetic oligonucleotides are synthesized. To make V2.Pf1 (N-M2(17-24/C17S), the oligonucleotides M2(17-24/C17S)-NcoI-F and HBc149/HindIII-R are used to amplify the hybrid HBc gene from vector V2.Pf1. The resultant 546 bp fragment is cleaved with NcoI and HindIII and inserted into pKK-223-3N, which has been cleaved with the same two enzymes.

To make V2.Pf1 [N-M2(17-24/C19S)], the oligonucleotides M2(17-24/C19S)-NcoI-F and HBc149/HindIII-R are used to amplify the hybrid HBc gene in vector V2.Pf1. The

```
ICC-1438 MGISLLTEVETPIRNEWGCRCNDSSDELLGWLWGI-HBc(2-149)     SEQ ID NO:289

ICC-1492 MGISLLTEVETPIRNEWGCRCNDSSDELLGWLWGI-HBc(2-149)-C   SEQ ID NO:290
```

It should be noted that to guard against translation initiation from the natural HBc initiator methionine, the codon for that residue was mutated to code for an isoleucine residue.

resultant 540 bp fragment is cleaved with NcoI and HindIII and inserted into pKK-223-3N, which had been cleaved with the same two enzymes.

```
M2(17-24/C17S)-NcoI-F     M  G  S  R  C  N  D  S  S  D  I  D  P  Y  K  E  F  G   SEQ ID NO: 291
                         .GGCGCCATGGGGTCTAGATGTAACGATTCAAGTGACATCGACCCTTATAAAGAATTTCG  SEQ ID NO: 292
```

-continued

| M2(17-24/C19S)-NcoI-F | M G <u>C</u> N D S S D I D P Y K E F G | SEQ ID NO: 293 |

GCG<u>CCATGG</u>GGTGTAACGATTCAAGTGACATCGACCCTTATAAAGAATTTGG   SEQ ID NO: 294

EXAMPLE 6

HBc Chimer Molecules With and Without Both N- and C-Terminal Cysteine Residues A series of HBc chimer molecule-containing particles was prepared that contained residues 1-24 of the influenza A, M2 protein peptide-bonded at or near the N-terminus of HBc whose C-terminus was truncated at residue 149. The component chimeric protein molecules contained different N-terminal sequences that included an M2 sequence or variant, and some contained a C-terminal cysteine residue.

All purified particles listed in Table 9, hereinafter, were analyzed by analytical size exclusion chromatography to assess the retention of particulate structure following purification. Particles designated ICC-1603, which contain no N-terminal cysteine residues, displayed evidence of disassembly back to sub-particulate structures (FIG. 3) because the protein eluted in the 1500 second range (particles elute at approximately 1000 seconds).

Figure 4:
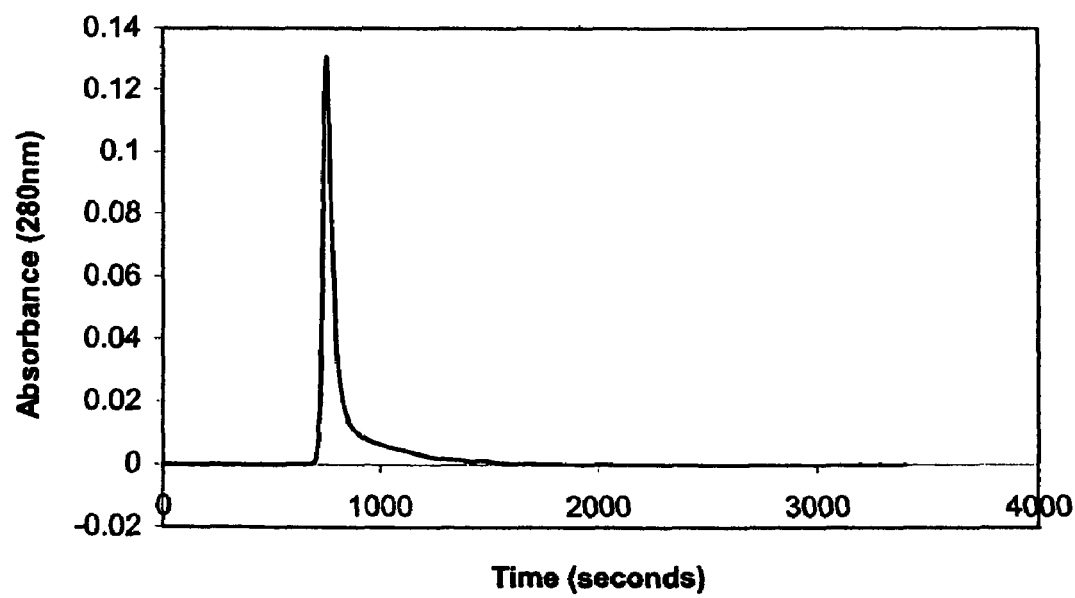
FIG. 4 is an analytical size exclusion chromatography elution profile for ICC-1590 particles as discussed for FIG. 3.

Similar analysis of particles ICC-1590, which are similar to ICC-1603 ICC-particles except for the mutation of two serine residues to cysteine residues in the N-terminal M2 sequence, revealed that that construct remained particulate following purification, with elution occurring at around 1000 seconds, which is typical for a hybrid particle (FIG. 4). There was no evidence of disassembly for ICC-1590 particles.

Figure 5:
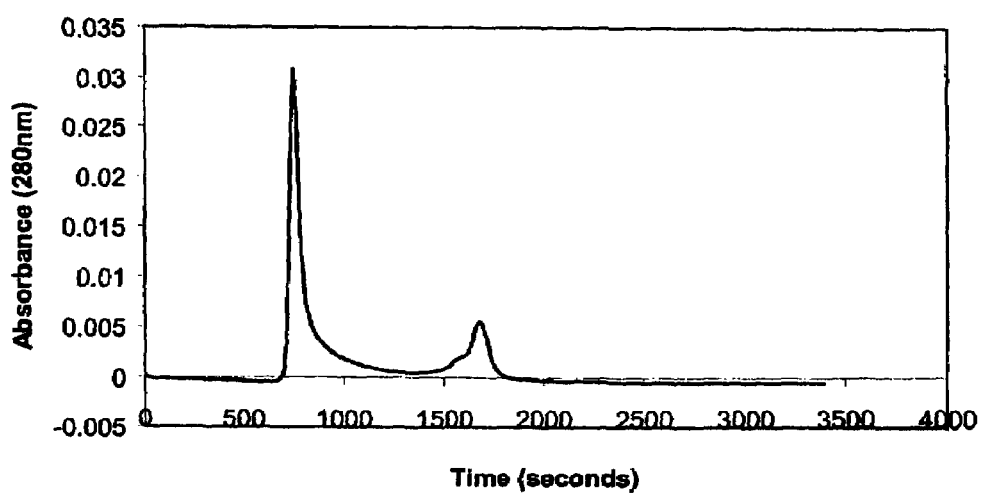
FIG. 5 is an analytical size exclusion chromatography elution profile for ICC-1560 particles as discussed for FIG. 3.

Analysis of ICC-1560 particles, whose chimer protein also has two N-terminal cysteine residues, revealed that it too was particulate following purification, although it did exhibit some degree of disassembly (FIG. 5), suggesting that the stabilization was not quite as robust as it was for ICC-1590 particles. Comparison of the N-terminal configurations of ICC-1590 and ICC-1560 particles (Table 11, hereinafter), shows that the relative position of the two cysteine residues in ICC-1560 particles is shifted by 3 amino acid residues relative to ICC-1590 particles via the deletion of three amino acid residues (DEL), indicating that the cysteine residues may be required to be a minimal distance from the start of the core gene to enable optimal cross-linking.

EXAMPLE 7

Figure 6:
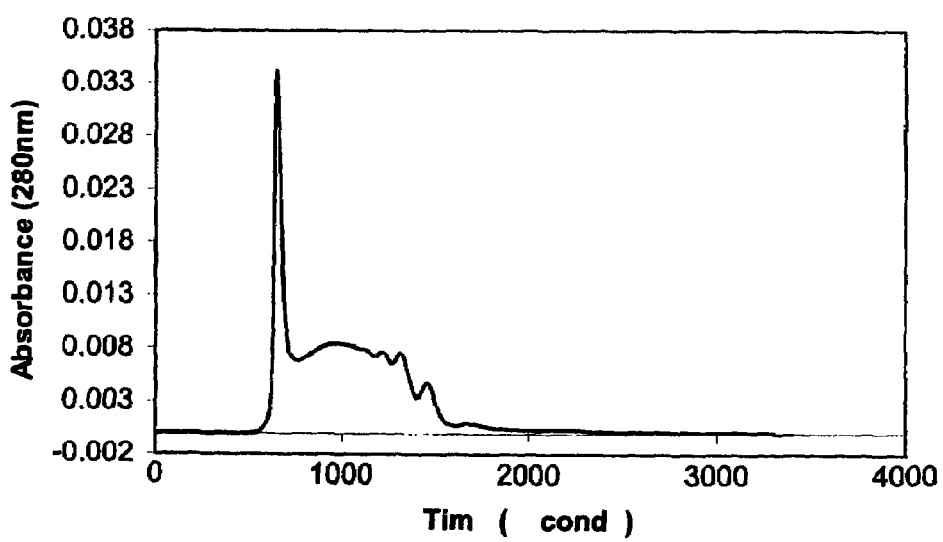
FIG. 6 is an analytical size exclusion chromatography elution profile for ICC-1605 particles as discussed for FIG. 3.

Particles With an M2 or M2 Variant Sequence and A C-Terminal Cysteine Residue ICC-1603 particles were shown in FIG. 3 to rapidly disassemble following purification. The HBc chimer molecules that comprise ICC-1605 particles are similar to those of ICC-1603 particles, except that the ICC-1605 component chimer molecules have a single C-terminal stabilizing cysteine. A plasmid was made to direct the expression of ICC-1605 particles to investigate if the addition of a C-terminal cysteine residue to ICC-1603 particles could impart greater stability on the particle. Following purification, ICC-1605 particles were analyzed using analytical size exclusion chromatography (FIG. 6).

The results of this study demonstrated that particle stabilization was more complete than for the ICC-1603 particles, but incomplete compared to ICC-1590 particles, which contains two amino-terminal cysteine residues and no C-terminal stabilizing cysteine. Although a significant amount of ICC-1605 remained particulate, there was evidence of a heterogeneous mixture of sub-particulate structures that eluted over a broad range. These observations suggest that for this hybrid particle (ICC-1603), C-terminal stabilization as found in ICC-1605 particles was less complete than for the N-terminal stabilization found in ICC-1590 particles.

Figure 7:
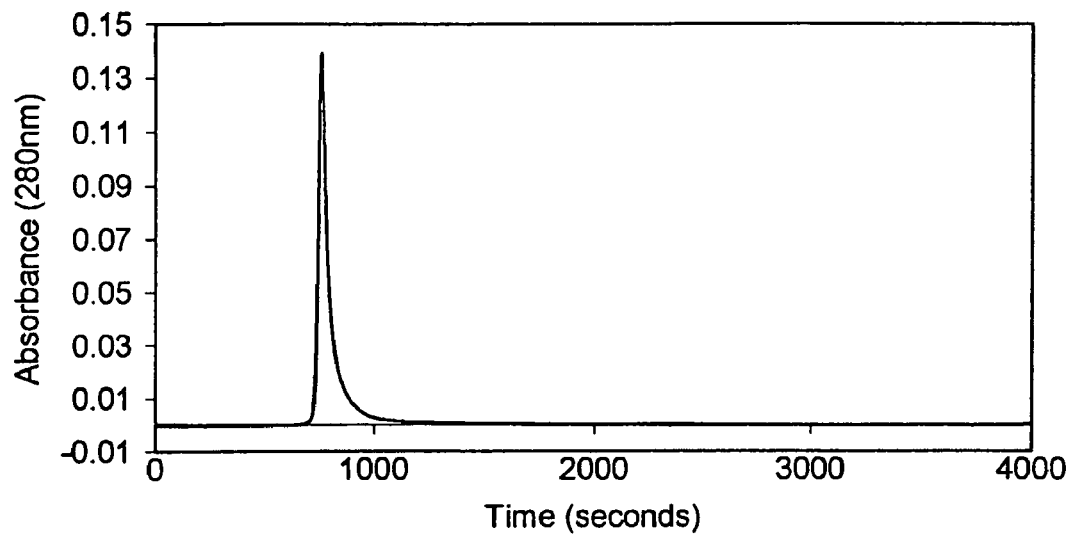
FIG. 7 is an analytical size exclusion chromatography elution profile for ICC-1604 particles as discussed for FIG. 3.

To investigate the compatibility of combined amino and carboxyl-terminal cysteine stabilization of hybrid particles, an expression plasmid was constructed to direct the expression of ICC-1604 particles. The component chimer molecules of ICC-1604 particles contain both the two amino-terminal stabilizing cysteine residues present in a native M2 polypeptide sequence (as in ICC-1590) as well as a C-terminal stabilizing cysteine (as in ICC-1605 particles). Analysis of ICC-1604 particles showed that they retained a homogeneous particulate state following purification (FIG. 7), indicating that the two stabilizing methods are complementary and can be used in concert with each other.

Alternative linker sequences between the N-terminus of HBc and the N-terminal cysteine residues were investigated using particles ICC-1438 and ICC-1492. Both of these particles contain the amino acid sequence ELLGWLWGIDI (SEQ ID NO:265) between the M2 fusion and amino acid D4 of HBc. The C-terminal nine amino acid residues of that sequence are derived from amino acids −6 of the HBc pre-core sequence to amino acid I3 of HBc, with the initiator codon of HBc mutated to an isoleucine to prevent translation initiation from this position, which would compromise the study. The HB pre-core sequence includes a cysteine at position −7.

Figure 8:
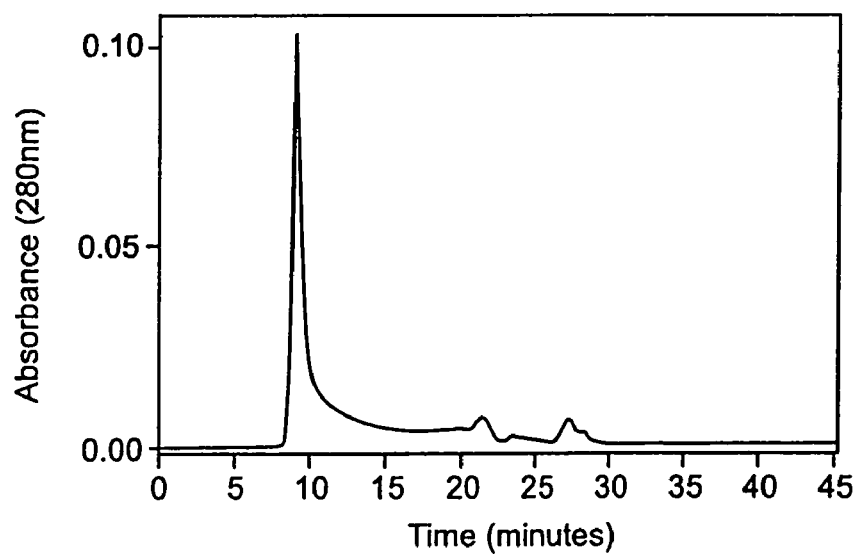
FIG. 8 is an analytical size exclusion chromatography elution profile for ICC-1438 particles as discussed for FIG. 3.
Figure 9:
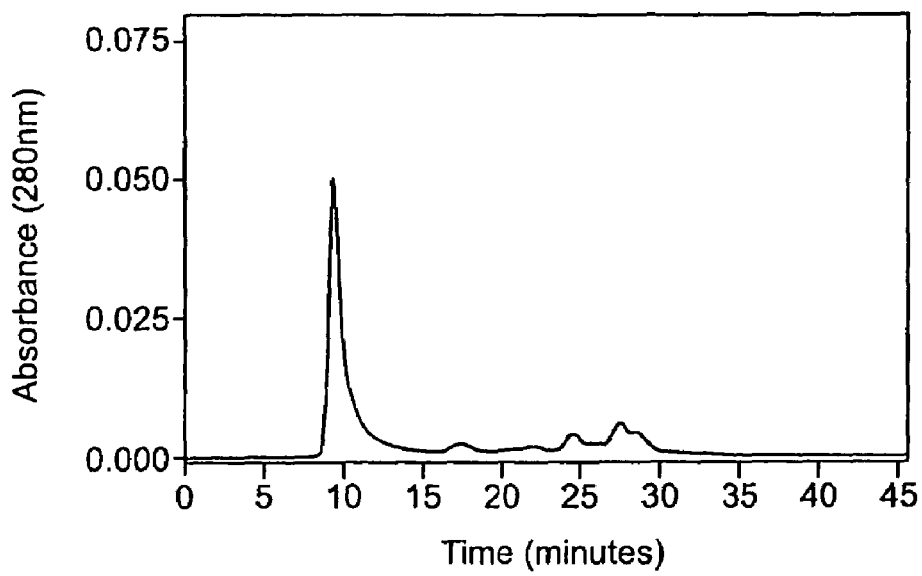
FIG. 9 is an analytical size exclusion chromatography elution profile for ICC-1492 particles as discussed for FIG. 3.

These particles differed only in the fact that the ICC-1438 component chimer molecule terminated at position 149 of HBc, whereas the ICC-1492 component chimer molecule terminated at 149 of HBc and contained a terminal cysteine at position 150 relative to the HBc of SEQ ID NO:1. When analyzed by analytical gel filtration, using an alternative but similar method to that discussed before, whereby particles elute at approximately 10 minutes, both constructs were shown to be particulate following purification (ICC-1438 in FIG. 8 and ICC-1492 in FIG. 10). This study demonstrated the compatibility of amino- and carboxyl-terminal cysteine stabilization of truncated particles, and the tolerance of substantial variability in the amino acid sequence and distance between the N-terminal cysteine residues and start of the HBc gene.

TABLE 9

| Construct Name | N-terminal Fusion | HBc N-term Start | Residues Between M2 and HBc | C-term End | Bound Nucleic Acid | C-term Cysteine Stab |
|---|---|---|---|---|---|---|
| ICC-1560 | M2 (1-24) | D4 | None | 149 | No | No |
| ICC-1603 | M2 (1-24) (2C > 2S) | D4 | EL | 149 | No | No |
| ICC-1590 | M2 (1-24) | D4 | EL | 149 | No | No |

TABLE 9-continued

| Construct Name | N-terminal Fusion | HBc N-term Start | Residues Between M2 and HBc | C-term End | Bound Nucleic Acid | C-term Cysteine Stab |
|---|---|---|---|---|---|---|
| ICC-1604 | M2 (1-24) | D4 | EL | 149 | No | Yes (C150) |
| ICC-1605 | M2 (1-24) (2C > 2S) | D4 | EL | 149 | No | Yes (C150) |
| ICC-1438 | M2 (1-24) | D2 | ELLGWLWGI | 149 | No | No |
| ICC-1492 | M2 (1-24) | D2 | ELLGWLWGI | 149 | No | Yes (C150) |

Table 10, below, shows an alignment that illustrates the configuration of the N-termini of HBeAg, and particles designated ICC-1590, ICC-1560, ICC-1603, ICC-1604 and ICC-1605. Sequences are aligned according to amino acid residue position 4 from the N-terminus of HBc of SEQ ID NO:1 that is shared by all constructs. N-terminal cysteine residues, when present, are underlined.

TABLE 10

| Construct Name | Sequence | SEQ ID NO |
|---|---|---|
| HBeAg | SKLCLGWLWGMDID | 295 |
| ICC-1590/ICC-1604 | MSLLTEVETPIRNEWGCRCNDSSDELD | 296 |
| ICC-1560 | MSLLTEVETPIRNEWGCRCNDSSD | 24 |
| ICC-1603/ICC-1605 | MSLLTEVETPIRNEWGSRSNDSSDELD | 297 |
| ICC-1438/ICC-1492 | MGISLLTEVETPIRNEWGCRCNDSSDELLGWLWGIDID | 298 |

Table 11, below, provides a tabulation of the results in which stability was assessed for particles containing an N-terminal influenza A M2 sequence or variant contemplated herein. As is seen, stable particles have been prepared from HBc chimer molecules that contain an N-terminal cysteine residue at a position of minus 14 (−14) relative to the N-terminus of the HBc sequence of SEQ ID NO:1 to about the N-terminus itself.

TABLE 11

| Construct Name | Amino Acids Between HBc D4 and N-terminal Cysteine Residues | | C-terminal Cysteine Stabilization | Stable Particle Formed |
|---|---|---|---|---|
| | Cys1 | Cys2 | | |
| HBeAg | — | 9 | No | No |
| ICC-1603 | — | — | No | No |
| ICC-1605 | — | — | Yes | Yes/No |
| ICC-1590 | 9 | 7 | No | Yes |
| ICC-1604 | 9 | 7 | Yes | Yes |
| ICC-1560 | 6 | 4 | No | Yes |
| ICC-1438 | 18 | 16 | No | Yes |
| ICC-1492 | 18 | 16 | Yes | Yes |

EXAMPLE 8

Partially Truncated HBc Particles: Synthesis of Expression Vectors for Expressing Partially Truncated Particles To prepare expression plasmids for expressing partially truncated HBc particles, a single amino terminal oligonucleotide PCR primer (HBc149/NcoI-F) was used in combination with a unique C-terminal primer. For example, to prepare the HBc156(E. Cr; ICC-1600 particles) expression plasmid, the primers HBc149/NcoI-F and HBc156(E. cR)-H3-R are used. Primers HBc149/NcoI-F and HBc156C (E. cR)-H3-R are used to prepare the HBc156(E. cR)+C (ICC-1601 particles) expression plasmids. The sequences of all primers used are displayed below.

In addition to truncating the particles—and in some cases the incorporating a C-terminal cysteine residue—codons that are optimal for expression in E. coli were also used. It is known that several arginine codons, particularly AGA and AGG are rarely used by E. coli and are believe to be problematic for efficient expression of proteins in E. coli by leading to stalling of polypeptide synthesis during translation, resulting in premature termination. Of the 16 arginine codons between 150 and 183 of HBc, 7 are encoded by the rare AGA codon and 2 are encoded by the very rare AGG codon. Therefore, in this study, all AGA and AGG codons were replaced with codons that are more frequently used by E. coli. To enable sequential replacement of the rare arginine codons, HBc156 genes are synthesized first (ICC-1600 and HBc156+C ICC-1601 particles), and then used as a template for the HBc163 constructs (ICC-1634 and HBc163+C ICC-1632 particles); the HBc163 constructs are thereafter used as template for the HBc171 constructs (ICC-1642 and HBC171+C ICC-1643 particles); finally, the HBc 171 constructs are used as a templates for the arginine codon optimized HBc182 and HBc183 constructs. A non-optimized HBc182 construct (ICC-1575) is also prepared for control purposes. All PCR products are cleaved with the restriction enzymes NcoI and HindIII and cloned into the expression vector pKK223-3N, which had been cut with the same enzymes as discussed before.

Amino Terminal Primer Sequence (NcoI restriction site is underlined):

```
HBc149/NcoI-F   5'-TTGGGCCATGGACATCGACCCTTA      SEQ ID NO:210
```

Carboxyl-Terminal Primer Sequences (HindIII restriction sites are underlined):

```
HBc156(E.cR)-H3-R   5'-GCGAAGCTTACTAAGGGGAGCGGCCTCGTCGACGAACAACAGTAGTCTCCGG
                                                                                    SEQ ID NO:299

HBc156C(E.cR)-H3-R 5'-GCGAAGCTTACTAACAAGGGGAGCGGCCTCGTCGACGAACAACAGTAGTCTCCGG
                                                                                    SEQ ID NO:300

HBc163(E.cR)-H3-R   5'-GCGAAGCTTACTAAGGCGAGGGAGTGCGCCGACGAGGGGAGCGGCCTCG
                                                                                    SEQ ID NO:301

HBc163C(E.cR)-H3-R 5'-GCGAAGCTTACTAACAAGGCGAGGGAGTGCGCCGACGAGGGGAGCGGCCTCG
                                                                                    SEQ ID NO:302

HBc171(E.cR)-H3-R   5'-GCGAAGCTTACTACGGCGATTGAGAGCGTCGACGGCGAGGCGAGGGAGT
                                                                                    SEQ ID NO:303

HBc171C(E.cR)-H3-R 5'-GCGAAGCTTACTAACACGGCGATTGAGAGCGTCGACGGCGAGGCGAGGGAGT
                                                                                    SEQ ID NO:304

HBc183(E.cR)-H3-R   5'-GCGAAGCTTACTAACATTGAGATTCCCGAGATTGAGATCGCCGGCGACGCGGCGATTGAGAGCGTC
                                                                                    SEQ ID NO:305

HBc182-H3-R         5'-GCGAAGCTTACTATTGAGATTCCCGAGATTGA
                                                                                    SEQ ID NO:306

HBc183-H3-R         5'-GGAAAGCTTACTAACATTGAGATTCCCG
                                                                                    SEQ ID NO:307

HBc149/HindIII-R    5'-CGCAAGCTTAAACAACAGTAGTCTCCGGAAG
                                                                                    SEQ ID NO:213

HBc149 + C/Hin-     5'-CGCAAGCTTACTAGCAAACAACAGTAGTCTCCGGAAG
dIII-R                                                                              SEQ ID NO:308
```

EXAMPLE 9

Particle Formulations

Formulation With Corixa 529-SE

The recombinant hepatitis B core particle solution after purification is filter sterilized. A quantity of solution containing the desired dose of immunogenic particles (typically 0.02 to 0.2 mg) is added to a vial. Corixa 529-SE (available from Corixa Corp., WA) is added at the desired concentration (typically 0.01 to 0.2 mg), and saline is added to bring the volume to 1 mL. The resulting admixture is agitated to substantial homogeneity.

Formulation With Alhydrogel and Corixa RC-529

Corixa RC-529 (typically 0.02 to 0.2 mg; available from Corixa Corp., WA) is added to aluminium hydroxide gel (1 mg). The recombinant purified immunogenic chimer particles are then added (typically at a dose of 0.02 to 2 mg), and saline added to bring the volume to 1 mL. The resulting admixture is agitated to substantial homogeneity.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A method of enhancing the production of one or more of gamma-producing CD 8+, CD 4+ T cells and cytotoxic T lymphocytes against hepatitis B virus that comprises;

(a) administering to a patient chronically infected with hepatitis B virus a T cell-stimulating amount of a composition comprising immunogenic particles dispersed in a squalene oil-in-water emulsion that includes an adjuvant comprised of a 2-[(R)-3-tetradecanoyloxytetra-decanoylamino]-ethyl-2-deoxy-4-O-phosphono-3-O-[(R)-3-tetradecanoyloxytetra-decanoyl]-2-[(R)-3-tetra-decanoyloxytetradecanoyl-amino]-p-D-glucopyranoside triethylammonium salt, said immunogenic particles comprising recombinant hepatitis B core (HBc) chimeric protein molecules, said chimeric protein molecules being up to about 550 amino acid residues in length and containing (i) an HBc sequence of at least about 125 of the N-terminal 165 amino acid residues of the HBc molecule that includes the HBc sequence of residue positions 4 through about 75 and about 85 through about 140, and includes an insert in the HBc immunodominant loop, said insert having a length of one to about 40 amino acid residues containing one or more chemically non-reactive heterologous amino acid residues that render the immunogenic particles less antigenic than the native HBc particles, (ii) one or both of (a') one to three cysteine residues at an amino acid position of the chimer molecule corresponding to amino acid position −20 to about +1 from the N-terminus of the HBc sequence of SEQ ID NO:1 [N-terminal cysteine residue(s)] in a sequence other than that of the HBc precore sequence and (b') one to about three cysteine residues toward the C-terminus of the molecule from the C-terminal residue of the HBc sequence and within about 30 residues from the C-terminus of the chimer molecule [C-terminal cysteine residue(s)], said chimer molecule (a') containing no more than about 5 percent conservatively substituted amino acid residues in the HBc sequence relative to one of SEQ ID NO:1-6 from position 2 through 165, (b') having one or both HBc cysteine residues at positions 48 and 107 replaced by another residue, while the HBc cysteine at residue at position 61 is present, and (c') self-assembling into particles that upon expression in a host cell are substantially free of binding to nucleic acids, and said particles being more stable than are particles formed from otherwise identical HBc chimer molecules that are free of any above-mentioned C-terminal cysteine residue(s) or N-terminal cysteine residue(s) or in which a C-terminal or an N-terminal cysteine residue(s) present in a contemplated chimer molecule is(are) replaced by another residue; and (b) maintaining said patient for a time sufficient to induce T cells activated against HBc.

2. The method according to claim 1 wherein said recombinant HBc chimeric protein molecules have both HBc cysteine residues at positions 48 and 107 are replaced by another residue, and the HBc cysteine at residue at position 61 present.

3. A method of enhancing the production of one or more of gamma-producing CD 8+, CD 4+ T cells and cytotoxic T lymphocytes against hepatitis B virus that comprises;

administering to a patient having a chronic hepatitis B virus infection a T cell-stimulating amount of a composition comprised of an immunogenic effective amount of immunogenic particles dispersed in a squalene oil-in-water emulsion that includes an adjuvant comprised of a 2-[(R)-3-tetra-decanoyloxytetradecanoyl-amino]-ethyl-2-deoxy-4-O-phosphono-3-O-[(R)-3-tetradecanoyloxytetra-decanoyl]-2-[(R)-3-tetra-decanoyloxytetradecanoyl-amino]-p-D-glucopyranoside triethylammonium salt, said immunogenic particles being comprised of recombinant hepatitis B virus core (HBc) protein chimer molecules that have a length of about 135 to about 525 amino acid residues and contain four peptide-linked amino acid residue sequence domains from the N-terminus that are denominated Domains I, II, III and IV, wherein (i) Domain I comprises about 71 to about 110 amino acid residues whose sequence includes (a') at least the sequence of the residues of position 4 through position 75 of HBc, and (b') zero to three cysteine residues at an amino acid position of the chimer molecule corresponding to amino acid position −20 to about +1 from the N-terminus of the HBc sequence of SEQ ID NO:1 [N-terminal cysteine residue(s)] in a sequence other than that of the HBc precore sequence;

(ii) Domain II comprises about 5 to about 250 amino acid residues peptide-bonded to HBc residue 75 of Domain I in which (a') zero to all residues in the sequence of HBc positions 76 through 85 are present peptide-bonded to (b') a sequence of one to about 245 amino acid residues that contain one or more chemically non-reactive heterologous amino acid residues that render the immunogenic particles less antigenic than the native HBc particles;

(iii) Domain III is an HBc sequence from position 86 through position 135 peptide-bonded to residue 85 of Domain II; and (iv) Domain IV comprises (a') five through fourteen residues of an HBc amino acid residue sequence from position 136 through 149 peptide-bonded to the residue of position 135 of Domain III, and (b') zero to three cysteine residues [C-terminal cysteine residue(s)] within about 30 residues from the C-terminus of the chimer molecule, said chimer molecule (i) having an amino acid residue sequence in which no more than about 5 percent of the amino acid residues are substituted in the HBc sequence of the chimer relative to one of SEQ ID NO:1-6 from position 2 through 165, (ii) self-assembling into particles on expression in a host cell, (iii) containing at least one N-terminal cysteine residue or C-terminal cysteine residue, and (iv) having one or both HBc cysteine residues at positions 48 and 107 replaced by another residue, while the HBc cysteine at residue at position 61 is present, said particles being substantially free of binding to nucleic acids and being more stable than are particles formed from otherwise identical HBc chimer molecules that are (i) free of any above-mentioned C-terminal cysteine residue(s) or N-terminal cysteine residue(s) or (ii) in which said cysteine residue(s) of (iii) present in a contemplated chimer molecule is(are) replaced by another residue.

4. The method according to claim 3 wherein said recombinant HBc chimeric protein molecules have both HBc cysteine residues at positions 48 and 107 are replaced by another residue, and the HBc cysteine at residue at position 61 present.

5. The method according to claim 3 wherein said recombinant HBc chimer protein molecule contains one to three C-terminal cysteine residue(s) within about 30 residues of the C-terminus of the chimer molecule.

6. The method according to claim 5 wherein the HBc sequence between amino acid residues 76 and 85 is present, but interrupted by said one or more chemically non-reactive heterologous amino acid residues.

7. The method according to claim 5 wherein said recombinant HBc chimer protein molecule contains 1 cysteine residue within about 30 residues from the C-terminus of the chimer molecule.

8. The method according to claim 7 wherein said cysteine residue is located within about five amino acid residues of the C-terminus of the chimer protein molecule.

9. A method of enhancing the production of one or more of gamma-producing CD 8+, CD 4+ T cells and cytotoxic T lymphocytes against hepatitis B virus that comprises;

(a) administering to a patient chronically infected with hepatitis B virus a T cell-stimulating amount of a composition comprising immunogenic particles dispersed in a squalene oil-in-water emulsion that includes an adjuvant comprised of a 2-[(R)-3-tetradecanoyloxytetra-decanoylamino]-ethyl-2-deoxy-4-O-phosphono-3-O-[(R)-3-tetradecanoyloxytetra-decanoyl]-2-[(R)-3-tetra-decanoyloxytetradecanoyl-amino]-p-D-glucopyranoside triethylammonium salt and optionally contains an agonist for toll-like receptor-9 (TLR-9), said immunogenic particles comprising recombinant hepatitis B core (HBc) chimeric protein molecules, said chimeric protein molecules being up to about 550 amino acid residues in length and containing (i) an HBc sequence of at least about 125 of the N-terminal 165 amino acid residues of the HBc molecule that includes the HBc sequence of residue positions 4 through about 75 and about 85 through about 140, and includes an insert in the HBc immunodominant loop, said insert having a length of one to about 40 amino acid residues and containing one or more chemically non-reactive heterologous amino acid residues that render the immunogenic particles less antigenic than the native HBc particles, (ii) one or both of (a') one to three cysteine residues at an amino acid position of the chimer molecule corresponding to amino acid position −20 to about +1 from the N-terminus of the HBc sequence of SEQ ID NO:1 [N-terminal cysteine residue(s)] in a sequence other than that of the HBc precore sequence and (b') one to about three cysteine residues toward the C-terminus of the molecule from the C-terminal residue of the HBc sequence and within about 30 residues from the C-terminus of the chimer molecule [C-terminal cysteine residue(s)], said chimer molecule (a') containing no more than about 5 percent conservatively substituted amino acid residues in the HBc sequence relative to one of SEQ ID NO:1-6 from position 2 through 165, (b') self-assembling into particles that upon expression in a host cell are substantially free of binding to nucleic acids, and said particles being more stable than are particles formed from otherwise identical HBc chimer molecules that are free of any above-mentioned C-terminal cysteine residue(s) or N-terminal cysteine residue(s) or in which a C-terminal or an N-terminal cysteine residue(s) present in a contemplated chimer molecule is(are) replaced by another residue; and (b) maintaining said patient for a time sufficient to induce T cells activated against HBc.

10. The method according to claim 9 wherein said adjuvant and said TLR-9 agonist, when present, are admixed with said pharmaceutically acceptable diluent and said immunogenic particles.

11. A method of enhancing the production of one or more of gamma-producing CD 8+, CD 4+ T cells and cytotoxic T lymphocytes against hepatitis B virus that comprises;

(a) administering to a patient chronically infected with hepatitis B virus a T cell-stimulating amount of a composition comprising immunogenic particles dispersed in a squalene oil-in-water emulsion that includes an adjuvant comprised of a 2-[(R)-3-tetradecanoyloxytetra-decanoylamino]-ethyl-2-deoxy-4-O-phosphono-3-O-[(R)-3-tetradecanoyloxytetra-decanoyl]-2-[(R)-3- tetradecanoyloxy-tetradecanoyl-amino]-p-D-glucopyranoside triethylammonium salt and an optional agonist for toll-like receptor-9 (TLR-9), said immunogenic particles comprising recombinant hepatitis B core (HBc) chimeric protein molecules, said chimeric protein molecules being up to about 550 amino acid residues in length, wherein said recombinant HBc chimeric protein molecules have one or both HBc cysteine residues at positions 48 and 107 replaced by another residue, and the HBc cysteine at residue at position 61 is present, said chimer protein molecules containing (i) an HBc sequence of at least about 125 of the N-terminal 165 amino acid residues of the HBc molecule that includes the HBc sequence of residue positions 4 through about 75 and about 85 through about 140, and includes an insert in the HBc immunodominant loop, said insert having a length of one to about 40 amino acid residues and containing one or more chemically non-reactive heterologous amino acid residues that render the immunogenic particles less antigenic than the native HBc particles, (ii) one or both of (a') one to three cysteine residues at an amino acid position of the chimer molecule corresponding to amino acid position −20 to about +1 from the N-terminus of the HBc sequence of SEQ ID NO:1 [N-terminal cysteine residue(s)] in a sequence other than that of the HBc precore sequence and (b') one to about three cysteine residues toward the C-terminus of the molecule from the C-terminal residue of the HBc sequence and within about 30 residues from the C-terminus of the chimer molecule [C-terminal cysteine residue(s)], said chimer molecule (a') containing no more than about 5 percent conservatively substituted amino acid residues in the HBc sequence relative to one of SEQ ID NO:1-6 from position 2 through 165, (b') self-assembling into particles that upon expression in a host cell are substantially free of binding to nucleic acids, and said particles being more stable than are particles formed from otherwise identical HBc chimer molecules that are free of any above-mentioned C-terminal cysteine residue(s) or N-terminal cysteine residue(s) or in which a C-terminal or an N-terminal cysteine residue(s) present in a contemplated chimer molecule is(are) replaced by another residue; and (b) maintaining said patient for a time sufficient to induce T cells activated against HBc.

12. A method of enhancing the production of one or more of gamma-producing CD 8+, CD 4+ T cells and cytotoxic T lymphocytes against hepatitis B virus that comprises;

administering to a patient having a chronic hepatitis B virus infection a T cell-stimulating amount of a composition comprised of an immunogenic effective amount of immunogenic particles dispersed in a squalene oil-in-water diluent emulsion that includes an adjuvant comprised of a 2-[(R)-3-tetradecanoyloxytetra-decanoylamino]-ethyl-2-deoxy-4-O-phosphono-3-O-[(R)-3-tetradecanoyloxytetra-decanoyl]-2-[(R)-3-tetra-decanoyloxytetradecanoyl-amino]-p-D-glucopyranoside triethylammonium salt, said immunogenic particles being comprised of recombinant hepatitis B virus core (HBc) protein chimer molecules that have a HBc sequence from position 2 through position 149 and contain four peptide-linked amino acid residue sequence domains from the N-terminus that are denominated Domains I, II, III and IV, wherein (i) Domain I comprises about 71 to about 110 amino acid residues whose sequence includes the sequence of the residues of position 2 through position 75 of HBc;

(ii) Domain II comprises amino acid residues peptide-bonded to HBc residue 75 of Domain I in which (a') all residues in the sequence of HBc positions 76 through 85 are present peptide-bonded to (b') a single chemically non-reactive heterologous amino acid residues that renders the immunogenic particles less antigenic than native HBc particles;

(iii) Domain III is an HBc sequence from position 86 through position 135 peptide-bonded to residue 85 of Domain II; and (iv) Domain IV comprises (a') fourteen residues of an HBc amino acid residue sequence from position 136 through 149 peptide-bonded to the residue of position 135 of Domain III, and (b') one C-terminal cysteine residue, said chimer molecule (i) having an amino acid residue sequence in which no more than about 5 percent of the amino acid residues are substituted in the HBc sequence of the chimer relative to one of SEQ ID NO:1-6 from position 2 through 149, (ii) self-assembling into particles on expression in a host cell, (iii) having both HBc cysteine residues at positions 48 and 107 replaced by another residue, while the HBc cysteine at residue at position 61 is present, said particles being substantially free of binding to nucleic acids and being more stable than are particles formed from otherwise identical HBc chimer molecules that are (i) free of an above-mentioned C-terminal cysteine residue or (ii) in which said C-terminal cysteine residue present in a contemplated chimer molecule is replaced by another residue.

* * * * *

SEQUENCE LISTING

<160> NUMBER OF SEQ ID NOS: 308

<210> SEQ ID NO 1
<211> LENGTH: 183
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Val Asn Leu Glu Asp Pro Ala
65                  70                  75                  80

Ser Arg Asp Leu Val Val Ser Tyr Val Asn Thr Asn Met Gly Leu Lys
                85                  90                  95

Phe Arg Gln Leu Leu Trp Phe His Ile Ser Cys Leu Thr Phe Gly Arg
            100                 105                 110

Glu Thr Val Ile Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 2
<211> LENGTH: 185
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Gln Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

```
Pro Pro Ala Tyr Arg Pro Pro Asn Ala Pro Ile Leu Ser Thr Leu Pro
        130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Ser Gln Ser Pro Arg Arg Arg
                165                 170                 175

Arg Ser Gln Ser Arg Glu Ser Gln Cys
            180                 185

<210> SEQ ID NO 3
<211> LENGTH: 185
<212> TYPE: PRT
<213> ORGANISM: Hepatitis B virus

<400> SEQUENCE: 3

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Val Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Pro Ser Gln Ser Pro Arg Arg Arg
                165                 170                 175

Arg Ser Gln Ser Arg Glu Ser Gln Cys
            180                 185

<210> SEQ ID NO 4
<211> LENGTH: 183
<212> TYPE: PRT
<213> ORGANISM: Hepatitis B virus

<400> SEQUENCE: 4

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ala Ala Leu Tyr Arg Asp Ala Leu Glu Ser Pro Glu His Cys
            35                  40                  45

Ser Pro His His Thr Ala Leu Arg Gln Ala Ile Leu Cys Trp Gly Asp
        50                  55                  60

Leu Met Thr Leu Ala Thr Trp Val Gly Thr Asn Leu Glu Asp Pro Ala
65                  70                  75                  80
```

```
Ser Arg Asp Leu Val Val Ser Tyr Val Asn Thr Asn Val Gly Leu Lys
                85                  90                  95

Phe Arg Gln Leu Leu Trp Phe His Ile Ser Cys Leu Thr Phe Gly Arg
               100                 105                 110

Glu Thr Val Leu Glu Tyr Leu Val Ser Phe Gly Val Trp Ile Arg Thr
               115                 120                 125

Pro Pro Ala Tyr Arg Pro Pro Asn Ala Pro Ile Leu Ser Thr Leu Pro
               130                 135                 140

Glu Thr Thr Val Val Arg Arg Arg Gly Arg Ser Pro Arg Arg Arg Thr
145                 150                 155                 160

Pro Ser Pro Arg Arg Arg Ser Gln Ser Pro Arg Arg Arg Ser
               165                 170                 175

Gln Ser Arg Glu Ser Gln Cys
               180

<210> SEQ ID NO 5
<211> LENGTH: 183
<212> TYPE: PRT
<213> ORGANISM: Marmota monax

<400> SEQUENCE: 5

Met Asp Ile Asp Pro Tyr Lys Glu Phe Gly Ser Ser Tyr Gln Leu Leu
1               5                   10                  15

Asn Phe Leu Pro Leu Asp Phe Phe Pro Asp Leu Asn Ala Leu Val Asp
                20                  25                  30

Thr Ala Thr Ala Leu Tyr Glu Glu Leu Thr Gly Arg Glu His Cys
            35                  40                  45

Ser Pro His His Thr Ala Ile Arg Gln Ala Leu Val Cys Trp Asp Glu
            50                  55                  60

Leu Thr Lys Leu Ile Ala Trp Met Ser Ser Asn Ile Thr Ser Glu Gln
65                  70                  75                  80

Val Arg Thr Ile Ile Val Asn His Val Asn Asp Thr Trp Gly Leu Lys
                85                  90                  95

Val Arg Gln Ser Leu Trp Phe His Leu Ser Cys Leu Thr Phe Gly Gln
               100                 105                 110

His Thr Val Gln Glu Phe Leu Val Ser Phe Gly Val Trp Ile Arg Thr
               115                 120                 125

Pro Ala Pro Tyr Arg Pro Pro Asn Ala Pro Ile Leu Ser Thr Leu Pro
               130                 135                 140

Glu His Thr Val Ile Arg Arg Arg Gly Gly Ala Arg Ala Ser Arg Ser
145                 150                 155                 160

Pro Arg Arg Arg Thr Pro Ser Pro Arg Arg Arg Ser Gln Ser Pro
               165                 170                 175

Arg Arg Arg Arg Ser Gln Cys
               180

<210> SEQ ID NO 6
<211> LENGTH: 217
<212> TYPE: PRT
<213> ORGANISM: Spermophilus variegatus

<400> SEQUENCE: 6

Met Tyr Leu Phe His Leu Cys Leu Val Phe Ala Cys Val Pro Cys Pro
1               5                   10                  15

Thr Val Gln Ala Ser Lys Leu Cys Leu Gly Trp Leu Trp Asp Met Asp
                20                  25                  30
```

```
Ile Asp Pro Tyr Lys Glu Phe Gly Ser Ser Tyr Gln Leu Leu Asn Phe
        35                  40                  45

Leu Pro Leu Asp Phe Phe Pro Asp Leu Asn Ala Leu Val Asp Thr Ala
 50                  55                  60

Ala Ala Leu Tyr Glu Glu Leu Thr Gly Arg Glu His Cys Ser Pro
 65                  70                  75                  80

His His Thr Ala Ile Arg Gln Ala Leu Val Cys Trp Glu Glu Leu Thr
                85                  90                  95

Arg Leu Ile Thr Trp Met Ser Glu Asn Thr Thr Glu Glu Val Arg Arg
             100                 105                 110

Ile Ile Val Asp His Val Asn Asn Thr Trp Gly Leu Lys Val Arg Gln
             115                 120                 125

Thr Leu Trp Phe His Leu Ser Cys Leu Thr Phe Gly Gly His Thr Val
         130                 135                 140

Gln Glu Phe Leu Val Ser Phe Gly Val Trp Ile Arg Thr Pro Ala Pro
145                 150                 155                 160

Tyr Arg Pro Pro Asn Ala Pro Ile Leu Ser Thr Leu Pro Glu His Thr
                 165                 170                 175

Val Ile Arg Arg Arg Gly Gly Ser Arg Ala Ala Arg Ser Pro Arg Arg
                180                 185                 190

Arg Thr Pro Ser Pro Arg Arg Arg Ser Gln Ser Pro Arg Arg Arg
             195                 200                 205

Arg Ser Gln Ser Pro Ala Ser Asn Cys
    210                 215

<210> SEQ ID NO 7
<211> LENGTH: 51
<212> TYPE: DNA
<213> ORGANISM: Artificial Sequence
<220> FEATURE:
<223> OTHER INFORMATION: plasmid pkk223

<400> SEQUENCE: 7
ttcacacagg aaacagaatt cccggggatc cgtcgacctg cagccaagct t          51

<210> SEQ ID NO 8
<211> LENGTH: 38
<212> TYPE: DNA
<213> ORGANISM: Artificial Sequence
<220> FEATURE:
<223> OTHER INFORMATION: plasmid pkk223

<400> SEQUENCE: 8
ttcacataag gaggaaaaaa ccatgggatc cgaagctt                         38

<210> SEQ ID NO 9
<211> LENGTH: 15
<212> TYPE: PRT
<213> ORGANISM: Streptococcus pneumoniae

<400> SEQUENCE: 9

Lys Leu Glu Glu Leu Ser Asp Lys Ile Asp Glu Leu Asp Ala Glu
 1               5                  10                  15

<210> SEQ ID NO 10
<211> LENGTH: 35
<212> TYPE: PRT
<213> ORGANISM: Streptococcus pneumoniae

<400> SEQUENCE: 10
```

```
Gln Lys Lys Tyr Asp Glu Asp Gln Lys Lys Thr Glu Glu Lys Ala Ala
1               5                   10                  15

Leu Glu Lys Ala Ala Ser Glu Glu Met Asp Lys Ala Val Ala Ala Val
            20                  25                  30

Gln Gln Ala
        35

<210> SEQ ID NO 11
<211> LENGTH: 27
<212> TYPE: PRT
<213> ORGANISM: Cryptosporidium parvum

<400> SEQUENCE: 11

Gln Asp Lys Pro Ala Asp Ala Pro Ala Ala Glu Ala Pro Ala Ala Glu
1               5                   10                  15

Pro Ala Ala Gln Gln Asp Lys Pro Ala Asp Ala
            20                  25

<210> SEQ ID NO 12
<211> LENGTH: 17
<212> TYPE: PRT
<213> ORGANISM: Human immunodeficiency virus

<400> SEQUENCE: 12

Arg Lys Arg Ile His Ile Gly Pro Gly Arg Ala Phe Tyr Ile Thr Lys
1               5                   10                  15

Asn

<210> SEQ ID NO 13
<211> LENGTH: 31
<212> TYPE: PRT
<213> ORGANISM: Foot-and-mouth disease virus

<400> SEQUENCE: 13

Tyr Asn Gly Glu Cys Arg Tyr Asn Arg Asn Ala Val Pro Asn Leu Arg
1               5                   10                  15

Gly Asp Leu Gln Val Leu Ala Gln Lys Val Ala Arg Thr Leu Pro
            20                  25                  30

<210> SEQ ID NO 14
<211> LENGTH: 10
<212> TYPE: PRT
<213> ORGANISM: Influenza A virus

<400> SEQUENCE: 14

Tyr Arg Asn Leu Leu Trp Leu Thr Glu Lys
1               5                   10

<210> SEQ ID NO 15
<211> LENGTH: 23
<212> TYPE: PRT
<213> ORGANISM: Influenza A virus

<400> SEQUENCE: 15

Ser Leu Leu Thr Glu Val Glu Thr Pro Ile Arg Asn Glu Trp Gly Cys
1               5                   10                  15

Arg Cys Asn Gly Ser Ser Asp
            20

<210> SEQ ID NO 16
<211> LENGTH: 23
```

```
<212> TYPE: PRT
<213> ORGANISM: Influenza A virus

<400> SEQUENCE: 16

Ser Leu Leu Thr Glu Val Glu Thr Pro Ile Arg Asn Glu Trp Gly Cys
 1               5                  10                  15

Arg Cys Asn Asp Ser Ser Asp
            20

<210> SEQ ID NO 17
<211> LENGTH: 21
<212> TYPE: PRT
<213> ORGANISM: Influenza A virus

<400> SEQUENCE: 17

Ser Leu Leu Thr Glu Val Glu Thr Pro Ile Arg Asn Glu Trp Gly Ala
 1               5                  10                  15

Arg Ala Asn Asp Ser
            20

<210> SEQ ID NO 18
<211> LENGTH: 19
<212> TYPE: PRT
<213> ORGANISM: Influenza A virus

<400> SEQUENCE: 18

Glu Gln Gln Ser Ala Val Asp Ala Asp Asp Ser His Phe Val Ser Ile
 1               5                  10                  15

Glu Leu Glu

<210> SEQ ID NO 19
<211> LENGTH: 23
<212> TYPE: PRT
<213> ORGANISM: Influenza A virus

<400> SEQUENCE: 19

Ser Leu Leu Thr Glu Val Glu Thr Pro Ile Arg Asn Glu Trp Gly Ser
 1               5                  10                  15

Arg Ser Asn Asp Ser Ser Asp
            20

<210> SEQ ID NO 20
<211> LENGTH: 23
<212> TYPE: PRT
<213> ORGANISM: Influenza A virus

<400> SEQUENCE: 20

Ser Leu Leu Thr Glu Val Glu Thr Pro Ile Arg Asn Glu Trp Gly Ser
 1               5                  10                  15

Arg Cys Asn Asp Ser Ser Asp
            20

<210> SEQ ID NO 21
<211> LENGTH: 23
<212> TYPE: PRT
<213> ORGANISM: Influenza A virus

<400> SEQUENCE: 21

Ser Leu Leu Thr Glu Val Glu Thr Pro Ile Arg Asn Glu Trp Gly Cys
 1               5                  10                  15

Arg Ser Asn Asp Ser Ser Asp
            20
```

```
<210> SEQ ID NO 22
<211> LENGTH: 23
<212> TYPE: PRT
<213> ORGANISM: Influenza A virus

<400> SEQUENCE: 22

Ser Leu Leu Thr Glu Val Glu Thr Pro Ile Arg Asn Glu Trp Gly Cys
1               5                   10                  15

Arg Ala Asn Asp Ser Ser Asp
            20

<210> SEQ ID NO 23
<211> LENGTH: 23
<212> TYPE: PRT
<213> ORGANISM: Influenza A virus

<400> SEQUENCE: 23

Ser Leu Leu Thr Glu Val Glu Thr Pro Ile Arg Asn Glu Trp Gly Ala
1               5                   10                  15

Arg Cys Asn Asp Ser Ser Asp
            20

<210> SEQ ID NO 24
<211> LENGTH: 24
<212> TYPE: PRT
<213> ORGANISM: Influenza A virus

<400> SEQUENCE: 24

Met Ser Leu Leu Thr Glu Val Glu Thr Pro Ile Arg Asn Glu Trp Gly
1               5                   10                  15

Cys Arg Cys Asn Asp Ser Ser Asp
            20

<210> SEQ ID NO 25
<211> LENGTH: 24
<212> TYPE: PRT
<213> ORGANISM: Influenza A virus

<400> SEQUENCE: 25

Met Ser Leu Leu Thr Glu Val Glu Thr Pro Ile Arg Asn Glu Trp Gly
1               5                   10                  15

Ser Arg Ser Asn Asp Ser Ser Asp
            20

<210> SEQ ID NO 26
<211> LENGTH: 35
<212> TYPE: PRT
<213> ORGANISM: Influenza A virus

<400> SEQUENCE: 26

Met Gly Ile Ser Leu Leu Thr Glu Val Glu Thr Pro Ile Arg Asn Glu
1               5                   10                  15

Trp Gly Cys Arg Cys Asn Asp Ser Ser Asp Glu Leu Leu Gly Trp Leu
            20                  25                  30

Trp Gly Ile
        35

<210> SEQ ID NO 27
<211> LENGTH: 24
<212> TYPE: PRT
<213> ORGANISM: Influenza A virus
```

-continued

<400> SEQUENCE: 27

Met Ser Leu Leu Thr Glu Val Glu Thr Pro Ile Arg Asn Glu Trp Gly
1               5                   10                  15

Ala Arg Ala Asn Asp Ser Ser Asp
            20

<210> SEQ ID NO 28
<211> LENGTH: 24
<212> TYPE: PRT
<213> ORGANISM: Influenza A virus

<400> SEQUENCE: 28

Met Ser Leu Leu Thr Glu Val Glu Thr Pro Ile Arg Asn Glu Trp Gly
1               5                   10                  15

Cys Arg Ala Asn Asp Ser Ser Asp
            20

<210> SEQ ID NO 29
<211> LENGTH: 24
<212> TYPE: PRT
<213> ORGANISM: Influenza A virus

<400> SEQUENCE: 29

Met Ser Leu Leu Thr Glu Val Glu Thr Pro Ile Arg Asn Glu Trp Gly
1               5                   10                  15

Ala Arg Cys Asn Asp Ser Ser Asp
            20

<210> SEQ ID NO 30
<211> LENGTH: 24
<212> TYPE: PRT
<213> ORGANISM: Influenza A virus

<400> SEQUENCE: 30

Met Ser Leu Leu Thr Glu Val Glu Thr Pro Ile Arg Asn Glu Trp Gly
1               5                   10                  15

Cys Arg Ser Asn Asp Ser Ser Asp
            20

<210> SEQ ID NO 31
<211> LENGTH: 24
<212> TYPE: PRT
<213> ORGANISM: Influenza A virus

<400> SEQUENCE: 31

Met Ser Leu Leu Thr Glu Val Glu Thr Pro Ile Arg Asn Glu Trp Gly
1               5                   10                  15

Ser Arg Cys Asn Asp Ser Ser Asp
            20

<210> SEQ ID NO 32
<211> LENGTH: 24
<212> TYPE: PRT
<213> ORGANISM: Hepatitis B virus
<220> FEATURE:
<221> NAME/KEY: MISC_FEATURE
<222> LOCATION: (1)..(1)
<223> OTHER INFORMATION: Xaa at position 1 is methionine or absent. If
      methionine then Xaa in positions 2 through 8 are not absent
<220> FEATURE:
<221> NAME/KEY: MISC_FEATURE
<222> LOCATION: (2)..(2)
<223> OTHER INFORMATION: Xaa at position 2 is serine or absent. If serine then Xaa in positions 3 through 8 are not absent.
<220> FEATURE:
<221> NAME/KEY: MISC_FEATURE
<222> LOCATION: (3)..(3)
<223> OTHER INFORMATION: Xaa at position 3 is leucine or absent. If
      leucine then Xaa in positions 4 through 8 are not absent.
<220> FEATURE:
<221> NAME/KEY: MISC_FEATURE
<222> LOCATION: (4)..(4)
<223> OTHER INFORMATION: Xaa at position 4 is leucine or absent. If
      leucine then Xaa in positions 5 through 8 are not absent.
<220> FEATURE:
<221> NAME/KEY: MISC_FEATURE
<222> LOCATION: (5)..(5)
<223> OTHER INFORMATION: Xaa at position 5 is threonine, proline or
      absent. If threonine or proline then Xaa in positions 6 through
      8 are not absent.
<220> FEATURE:
<221> NAME/KEY: MISC_FEATURE
<222> LOCATION: (6)..(6)
<223> OTHER INFORMATION: Xaa at position 6 is glutamic acid or absent.
      If glutamic acid then Xaa in positions 7 through 8 are not absent.
<220> FEATURE:
<221> NAME/KEY: MISC_FEATURE
<222> LOCATION: (7)..(7)
<223> OTHER INFORMATION: Xaa at position 7 is valine or absent. If
      valine then Xaa in position 8 is not absent.
<220> FEATURE:
<221> NAME/KEY: MISC_FEATURE
<222> LOCATION: (8)..(8)
<223> OTHER INFORMATION: Xaa at position 8 is glutamic acid or absent.
<220> FEATURE:
<221> NAME/KEY: MISC_FEATURE
<222> LOCATION: (10)..(10)
<223> OTHER INFORMATION: Xaa at position 10 is proline, leucine or
      histidine.
<220> FEATURE:
<221> NAME/KEY: MISC_FEATURE
<222> LOCATION: (11)..(11)
<223> OTHER INFORMATION: Xaa at position 11 is isoleucine or threonine.
<220> FEATURE:
<221> NAME/KEY: MISC_FEATURE
<222> LOCATION: (13)..(13)
<223> OTHER INFORMATION: Xaa at position 13 is asparagine or serine.
<220> FEATURE:
<221> NAME/KEY: MISC_FEATURE
<222> LOCATION: (14)..(14)
<223> OTHER INFORMATION: Xaa at position 14 glutamic acid or glycine.
<220> FEATURE:
<221> NAME/KEY: MISC_FEATURE
<222> LOCATION: (15)..(15)
<223> OTHER INFORMATION: Xaa at position 15 is tryptophan or absent.
<220> FEATURE:
<221> NAME/KEY: MISC_FEATURE
<222> LOCATION: (16)..(16)
<223> OTHER INFORMATION: Xaa at position 16 is glycine, glutamic acid or
      absent. If glycine or glutamic acid then Xaa in position 15 is
      not absent.
<220> FEATURE:
<221> NAME/KEY: MISC_FEATURE
<222> LOCATION: (17)..(17)
<223> OTHER INFORMATION: Xaa at position 17 is absent or present, if
      present Xaa in position 17 is cysteine, serine or alanine. If
      Xaa in position 17 is present then positions 15 through 16 are
      not absent.
<220> FEATURE:
<221> NAME/KEY: MISC_FEATURE
<222> LOCATION: (18)..(18)
<223> OTHER INFORMATION: Xaa at position 18 is arginine, lysine or
      absent. If arginine or lysine then Xaa in positions 15 through
      17 are not absent.
<220> FEATURE:
<221> NAME/KEY: MISC_FEATURE
<222> LOCATION: (19)..(19)
<223> OTHER INFORMATION: Xaa at position 19 is absent or present, if
      present Xaa in position 19 is cysteine, serine or alanine. If
      Xaa in position 19 is present then positions 15 through 18 are
      not absent.
<220> FEATURE:

```
<221> NAME/KEY: MISC_FEATURE
<222> LOCATION: (20)..(20)
<223> OTHER INFORMATION: Xaa at position 20 is asparagine, serine or
      absent.  If asparagine or serine then Xaa in positions 15 through
      19 are not absent.
<220> FEATURE:
<221> NAME/KEY: MISC_FEATURE
<222> LOCATION: (21)..(21)
<223> OTHER INFORMATION: Xaa at position 21 is aspartic acid, glycine or
      absent.  If aspartic acid or glycine then Xaa in positions 15
      through 20 are not absent.
<220> FEATURE:
<221> NAME/KEY: MISC_FEATURE
<222> LOCATION: (22)..(22)
<223> OTHER INFORMATION: Xaa at position 22 is serine or absent.  If
      serine then Xaa in positions 15 through 21 are not absent.
<220> FEATURE:
<221> NAME/KEY: MISC_FEATURE
<222> LOCATION: (23)..(23)
<223> OTHER INFORMATION: Xaa at position 23 is serine or absent.  If
      serine then Xaa in positions 15 through 22 are not absent.
<220> FEATURE:
<221> NAME/KEY: MISC_FEATURE
<222> LOCATION: (24)..(24)
<223> OTHER INFORMATION: Xaa at position 24 is aspartic acid or absent.
      If aspartic acid then Xaa in positions 15 through 23 are not
      absent.

<400> SEQUENCE: 32

Xaa Xaa Xaa Xaa Xaa Xaa Xaa Xaa Thr Xaa Xaa Arg Xaa Xaa Xaa Xaa
1               5                   10                  15

Xaa Xaa Xaa Xaa Xaa Xaa Xaa Xaa
            20

<210> SEQ ID NO 33
<211> LENGTH: 17
<212> TYPE: PRT
<213> ORGANISM: Influenza A virus

<400> SEQUENCE: 33

Asn Asn Ala Thr Phe Asn Tyr Thr Asn Val Asn Pro Ile Ser His Ile
1               5                   10                  15

Arg

<210> SEQ ID NO 34
<211> LENGTH: 142
<212> TYPE: PRT
<213> ORGANISM: Yersinia pestis

<400> SEQUENCE: 34

Asp Ile Leu Lys Val Ile Val Asp Ser Met Asn His His Gly Asp Ala
1               5                   10                  15

Arg Ser Lys Leu Arg Glu Glu Leu Ala Glu Leu Thr Ala Glu Leu Lys
            20                  25                  30

Ile Tyr Ser Val Ile Gln Ala Glu Ile Asn Lys His Leu Ser Ser Ser
        35                  40                  45

Gly Thr Ile Asn Ile His Asp Lys Ser Ile Asn Leu Met Asp Lys Asn
    50                  55                  60

Leu Tyr Gly Tyr Thr Asp Glu Glu Ile Phe Lys Ala Ser Ala Glu Tyr
65                  70                  75                  80

Lys Ile Leu Glu Lys Met Pro Gln Thr Thr Ile Gln Val Asp Gly Ser
                85                  90                  95

Glu Lys Lys Ile Val Ser Ile Lys Asp Phe Leu Gly Ser Glu Asn Lys
            100                 105                 110

Arg Thr Gly Ala Leu Gly Asn Leu Lys Asn Ser Tyr Ser Tyr Asn Lys
```

```
                  115                 120                 125
Asp Asn Asn Glu Leu Ser His Phe Ala Thr Thr Cys Ser Asp
    130                 135                 140

<210> SEQ ID NO 35
<211> LENGTH: 19
<212> TYPE: PRT
<213> ORGANISM: Haemophilus influenzae

<400> SEQUENCE: 35

Cys Ser Ser Ser Asn Asn Asp Ala Ala Gly Asn Gly Ala Ala Gln Phe
1               5                   10                  15

Gly Gly Tyr

<210> SEQ ID NO 36
<211> LENGTH: 11
<212> TYPE: PRT
<213> ORGANISM: Haemophilus influenzae

<400> SEQUENCE: 36

Asn Lys Leu Gly Thr Val Ser Tyr Gly Glu Glu
1               5                   10

<210> SEQ ID NO 37
<211> LENGTH: 16
<212> TYPE: PRT
<213> ORGANISM: Haemophilus influenzae

<400> SEQUENCE: 37

Asn Asp Glu Ala Ala Tyr Ser Lys Asn Arg Arg Ala Val Leu Ala Tyr
1               5                   10                  15

<210> SEQ ID NO 38
<211> LENGTH: 28
<212> TYPE: PRT
<213> ORGANISM: Moraxella catarrhalis

<400> SEQUENCE: 38

Leu Asp Ile Glu Lys Asp Lys Lys Lys Arg Thr Asp Glu Gln Leu Gln
1               5                   10                  15

Ala Glu Leu Asp Asp Lys Tyr Ala Gly Lys Gly Tyr
            20                  25

<210> SEQ ID NO 39
<211> LENGTH: 28
<212> TYPE: PRT
<213> ORGANISM: Moraxella catarrhalis

<400> SEQUENCE: 39

Leu Asp Ile Glu Lys Asn Lys Lys Lys Arg Thr Glu Ala Glu Leu Gln
1               5                   10                  15

Ala Glu Leu Asp Asp Lys Tyr Ala Gly Lys Gly Tyr
            20                  25

<210> SEQ ID NO 40
<211> LENGTH: 28
<212> TYPE: PRT
<213> ORGANISM: Moraxella catarrhalis

<400> SEQUENCE: 40

Ile Asp Ile Glu Lys Lys Gly Lys Ile Arg Thr Glu Ala Glu Leu Leu
1               5                   10                  15
```

Ala Glu Leu Asn Lys Asp Tyr Pro Gly Gln Gly Tyr
            20                  25

<210> SEQ ID NO 41
<211> LENGTH: 25
<212> TYPE: PRT
<213> ORGANISM: Porphyromonas gingivalis

<400> SEQUENCE: 41

Gly Val Ser Pro Lys Val Cys Lys Asp Val Thr Val Glu Gly Ser Asn
1               5                   10                  15

Glu Phe Ala Pro Val Gln Asn Leu Thr
            20                  25

<210> SEQ ID NO 42
<211> LENGTH: 20
<212> TYPE: PRT
<213> ORGANISM: Porphyromonas gingivalis

<400> SEQUENCE: 42

Arg Ile Gln Ser Thr Trp Arg Gln Lys Thr Val Asp Leu Pro Ala Gly
1               5                   10                  15

Thr Lys Tyr Val
            20

<210> SEQ ID NO 43
<211> LENGTH: 21
<212> TYPE: PRT
<213> ORGANISM: Trypanosoma cruzi

<400> SEQUENCE: 43

Lys Ala Ala Ile Ala Pro Ala Lys Ala Ala Ala Ala Pro Ala Lys Ala
1               5                   10                  15

Ala Thr Ala Pro Ala
            20

<210> SEQ ID NO 44
<211> LENGTH: 16
<212> TYPE: PRT
<213> ORGANISM: Plasmodium falciparum

<400> SEQUENCE: 44

Asn Ala Asn Pro Asn Ala Asn Pro Asn Ala Asn Pro Asn Ala Asn Pro
1               5                   10                  15

<210> SEQ ID NO 45
<211> LENGTH: 24
<212> TYPE: PRT
<213> ORGANISM: Plasmodium falciparum

<400> SEQUENCE: 45

Asn Ala Asn Pro Asn Val Asp Pro Asn Ala Asn Pro Asn Ala Asn Pro
1               5                   10                  15

Asn Ala Asn Pro Asn Val Asp Pro
            20

<210> SEQ ID NO 46
<211> LENGTH: 20
<212> TYPE: PRT
<213> ORGANISM: Plasmodium falciparum

<400> SEQUENCE: 46

Asn Ala Asn Pro Asn Val Asp Pro Asn Ala Asn Pro Asn Ala Asn Pro

```
1               5                   10                  15

Asn Ala Asn Pro
            20

<210> SEQ ID NO 47
<211> LENGTH: 20
<212> TYPE: PRT
<213> ORGANISM: Plasmodium falciparum

<400> SEQUENCE: 47

Asn Ala Asn Pro Asn Ala Asn Pro Asn Ala Asn Pro Asn Val Asp Pro
1               5                   10                  15

Asn Ala Asn Pro
            20

<210> SEQ ID NO 48
<211> LENGTH: 28
<212> TYPE: PRT
<213> ORGANISM: Plasmodium falciparum

<400> SEQUENCE: 48

Asn Ala Asn Pro Asn Val Asp Pro Asn Ala Asn Pro Asn Ala Asn Pro
1               5                   10                  15

Asn Ala Asn Pro Asn Val Asp Pro Asn Ala Asn Pro
            20                  25

<210> SEQ ID NO 49
<211> LENGTH: 20
<212> TYPE: PRT
<213> ORGANISM: Plasmodium falciparum

<400> SEQUENCE: 49

Asn Pro Asn Val Asp Pro Asn Ala Asn Pro Asn Ala Asn Pro Asn Ala
1               5                   10                  15

Asn Pro Asn Val
            20

<210> SEQ ID NO 50
<211> LENGTH: 22
<212> TYPE: PRT
<213> ORGANISM: Plasmodium falciparum

<400> SEQUENCE: 50

Asn Pro Asn Val Asp Pro Asn Ala Asn Pro Asn Ala Asn Pro Asn Ala
1               5                   10                  15

Asn Pro Asn Val Asp Pro
            20

<210> SEQ ID NO 51
<211> LENGTH: 24
<212> TYPE: PRT
<213> ORGANISM: Plasmodium falciparum

<400> SEQUENCE: 51

Asn Pro Asn Val Asp Pro Asn Ala Asn Pro Asn Ala Asn Pro Asn Ala
1               5                   10                  15

Asn Pro Asn Val Asp Pro Asn Ala
            20

<210> SEQ ID NO 52
<211> LENGTH: 18
<212> TYPE: PRT
```

<213> ORGANISM: Plasmodium falciparum

<400> SEQUENCE: 52

Asn Val Asp Pro Asn Ala Asn Pro Asn Ala Asn Pro Asn Ala Asn Pro
1               5                   10                  15

Asn Val

<210> SEQ ID NO 53
<211> LENGTH: 20
<212> TYPE: PRT
<213> ORGANISM: Plasmodium falciparum

<400> SEQUENCE: 53

Asn Val Asp Pro Asn Ala Asn Pro Asn Ala Asn Pro Asn Ala Asn Pro
1               5                   10                  15

Asn Val Asp Pro
            20

<210> SEQ ID NO 54
<211> LENGTH: 22
<212> TYPE: PRT
<213> ORGANISM: Plasmodium falciparum

<400> SEQUENCE: 54

Asn Val Asp Pro Asn Ala Asn Pro Asn Ala Asn Pro Asn Ala Asn Pro
1               5                   10                  15

Asn Val Asp Pro Asn Ala
            20

<210> SEQ ID NO 55
<211> LENGTH: 16
<212> TYPE: PRT
<213> ORGANISM: Plasmodium falciparum

<400> SEQUENCE: 55

Asp Pro Asn Ala Asn Pro Asn Ala Asn Pro Asn Ala Asn Pro Asn Val
1               5                   10                  15

<210> SEQ ID NO 56
<211> LENGTH: 18
<212> TYPE: PRT
<213> ORGANISM: Plasmodium falciparum

<400> SEQUENCE: 56

Asp Pro Asn Ala Asn Pro Asn Ala Asn Pro Asn Ala Asn Pro Asn Val
1               5                   10                  15

Asp Pro

<210> SEQ ID NO 57
<211> LENGTH: 20
<212> TYPE: PRT
<213> ORGANISM: Plasmodium falciparum

<400> SEQUENCE: 57

Asp Pro Asn Ala Asn Pro Asn Ala Asn Pro Asn Ala Asn Pro Asn Val
1               5                   10                  15

Asp Pro Asn Ala
            20

<210> SEQ ID NO 58
<211> LENGTH: 19
<212> TYPE: PRT

<213> ORGANISM: Plasmodium vivax

<400> SEQUENCE: 58

Gly Asp Arg Ala Asp Gly Gln Pro Ala Gly Asp Arg Ala Asp Gly Gln
1               5                   10                  15

Pro Ala Gly

<210> SEQ ID NO 59
<211> LENGTH: 18
<212> TYPE: PRT
<213> ORGANISM: Plasmodium vivax

<400> SEQUENCE: 59

Arg Ala Asp Asp Arg Ala Ala Gly Gln Pro Ala Gly Asp Gly Gln Pro
1               5                   10                  15

Ala Gly

<210> SEQ ID NO 60
<211> LENGTH: 18
<212> TYPE: PRT
<213> ORGANISM: Plasmodium vivax

<400> SEQUENCE: 60

Ala Asn Gly Ala Gly Asn Gln Pro Gly Ala Asn Gly Ala Gly Asp Gln
1               5                   10                  15

Pro Gly

<210> SEQ ID NO 61
<211> LENGTH: 18
<212> TYPE: PRT
<213> ORGANISM: Plasmodium vivax

<400> SEQUENCE: 61

Ala Asn Gly Ala Asp Asn Gln Pro Gly Ala Asn Gly Ala Asp Asp Gln
1               5                   10                  15

Pro Gly

<210> SEQ ID NO 62
<211> LENGTH: 18
<212> TYPE: PRT
<213> ORGANISM: Plasmodium vivax

<400> SEQUENCE: 62

Ala Asn Gly Ala Gly Asn Gln Pro Gly Ala Asn Gly Ala Asp Asn Gln
1               5                   10                  15

Pro Gly

<210> SEQ ID NO 63
<211> LENGTH: 18
<212> TYPE: PRT
<213> ORGANISM: Plasmodium vivax

<400> SEQUENCE: 63

Ala Asn Gly Ala Gly Asn Gln Pro Gly Ala Asn Gly Ala Asp Asp Gln
1               5                   10                  15

Pro Gly

<210> SEQ ID NO 64
<211> LENGTH: 22
<212> TYPE: PRT
<213> ORGANISM: Plasmodium vivax

<400> SEQUENCE: 64

Ala Pro Gly Ala Asn Gln Glu Gly Gly Ala Ala Pro Gly Ala Asn
1               5                   10                  15

Gln Glu Gly Gly Ala Ala
            20

<210> SEQ ID NO 65
<211> LENGTH: 36
<212> TYPE: PRT
<213> ORGANISM: Plasmodium vivax

<400> SEQUENCE: 65

Ala Asn Gly Ala Gly Asn Gln Pro Gly Ala Asn Gly Ala Gly Asp Gln
1               5                   10                  15

Pro Gly Ala Asn Gly Ala Asp Asn Gln Pro Gly Ala Asn Gly Ala Asp
            20                  25                  30

Asp Gln Pro Gly
        35

<210> SEQ ID NO 66
<211> LENGTH: 16
<212> TYPE: PRT
<213> ORGANISM: Plasmodium berghei

<400> SEQUENCE: 66

Asp Pro Pro Pro Pro Asn Pro Asn Asp Pro Pro Pro Asn Pro Asn
1               5                   10                  15

<210> SEQ ID NO 67
<211> LENGTH: 24
<212> TYPE: PRT
<213> ORGANISM: Plasmodium yoelii

<400> SEQUENCE: 67

Gln Gly Pro Gly Ala Pro Gln Gly Pro Gly Ala Pro Gln Gly Pro Gly
1               5                   10                  15

Ala Pro Gln Gly Pro Gly Ala Pro
            20

<210> SEQ ID NO 68
<211> LENGTH: 15
<212> TYPE: PRT
<213> ORGANISM: Streptococcus sobrinus

<400> SEQUENCE: 68

Lys Pro Arg Pro Ile Tyr Glu Ala Lys Leu Ala Gln Asn Gln Lys
1               5                   10                  15

<210> SEQ ID NO 69
<211> LENGTH: 16
<212> TYPE: PRT
<213> ORGANISM: Streptococcus sobrinus

<400> SEQUENCE: 69

Ala Lys Ala Asp Tyr Glu Ala Lys Leu Ala Gln Tyr Glu Lys Asp Leu
1               5                   10                  15

<210> SEQ ID NO 70
<211> LENGTH: 9
<212> TYPE: PRT
<213> ORGANISM: Shigella flexneri -continued

```
<400> SEQUENCE: 70

Lys Asp Arg Thr Leu Ile Glu Gln Lys
1               5

<210> SEQ ID NO 71
<211> LENGTH: 15
<212> TYPE: PRT
<213> ORGANISM: respiratory syncytial virus

<400> SEQUENCE: 71

Cys Ser Ile Cys Ser Asn Asn Pro Thr Cys Trp Ala Ile Cys Lys
1               5                   10                  15

<210> SEQ ID NO 72
<211> LENGTH: 25
<212> TYPE: PRT
<213> ORGANISM: Entamoeba histolytica

<400> SEQUENCE: 72

Val Glu Cys Ala Ser Thr Val Cys Gln Asn Asp Asn Ser Cys Pro Ile
1               5                   10                  15

Ile Ala Asp Val Glu Lys Cys Asn Gln
            20                  25

<210> SEQ ID NO 73
<211> LENGTH: 34
<212> TYPE: PRT
<213> ORGANISM: Schistosoma japonicum

<400> SEQUENCE: 73

Asp Leu Gln Ser Glu Ile Ser Leu Ser Leu Glu Asn Gly Glu Leu Ile
1               5                   10                  15

Arg Arg Ala Lys Ser Ala Glu Ser Leu Ala Ser Glu Leu Gln Arg Arg
            20                  25                  30

Val Asp

<210> SEQ ID NO 74
<211> LENGTH: 34
<212> TYPE: PRT
<213> ORGANISM: Schistosoma mansoni

<400> SEQUENCE: 74

Asp Leu Gln Ser Glu Ile Ser Leu Ser Leu Glu Asn Ser Glu Leu Ile
1               5                   10                  15

Arg Arg Ala Lys Ala Ala Glu Ser Leu Ala Ser Asp Leu Gln Arg Arg
            20                  25                  30

Val Asp

<210> SEQ ID NO 75
<211> LENGTH: 26
<212> TYPE: PRT
<213> ORGANISM: Bovine Inhibin

<400> SEQUENCE: 75

Ser Thr Pro Pro Leu Pro Trp Pro Trp Ser Pro Ala Ala Leu Arg Leu
1               5                   10                  15

Leu Gln Arg Pro Pro Glu Glu Pro Ala Ala
            20                  25

<210> SEQ ID NO 76
<211> LENGTH: 17
```

<212> TYPE: PRT
<213> ORGANISM: Ebola virus

<400> SEQUENCE: 76

Ala Thr Gln Val Glu Gln His His Arg Arg Thr Asp Asn Asp Ser Thr
1               5                   10                  15

Ala

<210> SEQ ID NO 77
<211> LENGTH: 17
<212> TYPE: PRT
<213> ORGANISM: Ebola virus

<400> SEQUENCE: 77

His Asn Thr Pro Val Tyr Lys Leu Asp Ile Ser Glu Ala Thr Gln Val
1               5                   10                  15

Glu

<210> SEQ ID NO 78
<211> LENGTH: 17
<212> TYPE: PRT
<213> ORGANISM: Ebola virus

<400> SEQUENCE: 78

Gly Lys Leu Gly Leu Ile Thr Asn Thr Ile Ala Gly Val Ala Val Leu
1               5                   10                  15

Ile

<210> SEQ ID NO 79
<211> LENGTH: 14
<212> TYPE: PRT
<213> ORGANISM: Escherichia coli

<400> SEQUENCE: 79

Cys Cys Glu Leu Cys Cys Tyr Pro Ala Cys Ala Gly Cys Asn
1               5                   10

<210> SEQ ID NO 80
<211> LENGTH: 18
<212> TYPE: PRT
<213> ORGANISM: Escherichia coli

<400> SEQUENCE: 80

Asn Thr Phe Tyr Cys Cys Glu Leu Cys Cys Tyr Pro Ala Cys Ala Gly
1               5                   10                  15

Cys Asn

<210> SEQ ID NO 81
<211> LENGTH: 18
<212> TYPE: PRT
<213> ORGANISM: Escherichia coli

<400> SEQUENCE: 81

Ser Ser Asn Tyr Cys Cys Glu Leu Cys Cys Tyr Pro Ala Cys Ala Gly
1               5                   10                  15

Cys Asn

<210> SEQ ID NO 82
<211> LENGTH: 42
<212> TYPE: PRT
<213> ORGANISM: Alzheimer's disease b-Amyloid

```
<400> SEQUENCE: 82

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 83
<211> LENGTH: 17
<212> TYPE: PRT
<213> ORGANISM: Alzheimer's disease b-Amyloid

<400> SEQUENCE: 83

Asp Ala Glu Phe Arg His Asp Ser Gly Tyr Glu Val His His Gln Lys
1               5                   10                  15

Leu

<210> SEQ ID NO 84
<211> LENGTH: 11
<212> TYPE: PRT
<213> ORGANISM: Alzheimer's disease b-Amyloid

<400> SEQUENCE: 84

Glu Asp Val Gly Ser Asn Lys Gly Ala Ile Ile
1               5                   10

<210> SEQ ID NO 85
<211> LENGTH: 33
<212> TYPE: PRT
<213> ORGANISM: Alzheimer's disease b-Amyloid

<400> SEQUENCE: 85

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly

<210> SEQ ID NO 86
<211> LENGTH: 13
<212> TYPE: PRT
<213> ORGANISM: Neisseria meningitidis

<400> SEQUENCE: 86

Tyr Val Ala Val Glu Asn Gly Val Ala Lys Lys Val Ala
1               5                   10

<210> SEQ ID NO 87
<211> LENGTH: 15
<212> TYPE: PRT
<213> ORGANISM: Neisseria meningitidis

<400> SEQUENCE: 87

His Phe Val Gln Gln Thr Pro Lys Ser Gln Pro Thr Leu Val Pro
1               5                   10                  15

<210> SEQ ID NO 88
<211> LENGTH: 13
<212> TYPE: PRT
<213> ORGANISM: Neisseria meningitidis
```

```
<400> SEQUENCE: 88

His Val Val Val Asn Asn Lys Val Ala Thr His Val Pro
1               5                   10

<210> SEQ ID NO 89
<211> LENGTH: 12
<212> TYPE: PRT
<213> ORGANISM: Neisseria meningitidis

<400> SEQUENCE: 89

Pro Leu Gln Asn Ile Gln Pro Gln Val Thr Lys Arg
1               5                   10

<210> SEQ ID NO 90
<211> LENGTH: 21
<212> TYPE: PRT
<213> ORGANISM: Neisseria meningitidis

<400> SEQUENCE: 90

Ala Gln Ala Ala Asn Gly Gly Ala Ala Ser Gly Gln Val Lys Val Thr
1               5                   10                  15

Lys Val Thr Lys Ala
            20

<210> SEQ ID NO 91
<211> LENGTH: 10
<212> TYPE: PRT
<213> ORGANISM: Neisseria meningitidis

<400> SEQUENCE: 91

Tyr Val Asp Glu Gln Ser Lys Tyr His Ala
1               5                   10

<210> SEQ ID NO 92
<211> LENGTH: 15
<212> TYPE: PRT
<213> ORGANISM: Neisseria meningitidis

<400> SEQUENCE: 92

His Phe Val Gln Asn Lys Gln Asn Gln Pro Pro Thr Leu Val Pro
1               5                   10                  15

<210> SEQ ID NO 93
<211> LENGTH: 18
<212> TYPE: PRT
<213> ORGANISM: Neisseria meningitidis

<400> SEQUENCE: 93

Lys Pro Ser Ser Thr Asn Ala Lys Thr Gly Asn Lys Val Glu Val Thr
1               5                   10                  15

Lys Ala

<210> SEQ ID NO 94
<211> LENGTH: 17
<212> TYPE: PRT
<213> ORGANISM: Neisseria meningitidis

<400> SEQUENCE: 94

Tyr Trp Thr Thr Val Asn Thr Gly Ser Ala Thr Thr Thr Thr Phe Val
1               5                   10                  15

Pro
```

```
<210> SEQ ID NO 95
<211> LENGTH: 11
<212> TYPE: PRT
<213> ORGANISM: Neisseria meningitidis

<400> SEQUENCE: 95

Tyr Val Asp Glu Lys Lys Lys Met Val His Ala
1               5                   10

<210> SEQ ID NO 96
<211> LENGTH: 13
<212> TYPE: PRT
<213> ORGANISM: Neisseria meningitidis

<400> SEQUENCE: 96

His Tyr Thr Arg Gln Asn Asn Ala Asp Val Phe Val Pro
1               5                   10

<210> SEQ ID NO 97
<211> LENGTH: 14
<212> TYPE: PRT
<213> ORGANISM: Neisseria meningitidis

<400> SEQUENCE: 97

Tyr Tyr Thr Lys Asp Thr Asn Asn Leu Thr Leu Val Pro
1               5                   10

<210> SEQ ID NO 98
<211> LENGTH: 14
<212> TYPE: PRT
<213> ORGANISM: Neisseria meningitidis

<400> SEQUENCE: 98

Pro Pro Gln Lys Asn Gln Ser Gln Pro Val Val Thr Lys Ala
1               5                   10

<210> SEQ ID NO 99
<211> LENGTH: 14
<212> TYPE: PRT
<213> ORGANISM: Neisseria meningitidis

<400> SEQUENCE: 99

Pro Pro Ser Lys Gly Gln Thr Gly Asn Lys Val Thr Lys Gly
1               5                   10

<210> SEQ ID NO 100
<211> LENGTH: 14
<212> TYPE: PRT
<213> ORGANISM: Neisseria meningitidis

<400> SEQUENCE: 100

Pro Pro Ser Lys Ser Gln Pro Gln Val Lys Val Thr Lys Ala
1               5                   10

<210> SEQ ID NO 101
<211> LENGTH: 18
<212> TYPE: PRT
<213> ORGANISM: Neisseria meningitidis

<400> SEQUENCE: 101

Gln Pro Gln Thr Ala Asn Thr Gln Gln Gly Gly Lys Val Lys Val Thr
1               5                   10                  15

Lys Ala
```

```
<210> SEQ ID NO 102
<211> LENGTH: 18
<212> TYPE: PRT
<213> ORGANISM: Neisseria meningitidis

<400> SEQUENCE: 102

Gln Pro Gln Val Thr Asn Gly Val Gln Gly Asn Gln Val Lys Val Thr
1               5                   10                  15

Lys Ala

<210> SEQ ID NO 103
<211> LENGTH: 18
<212> TYPE: PRT
<213> ORGANISM: Neisseria meningitidis

<400> SEQUENCE: 103

Gln Pro Ser Lys Ala Gln Gly Gln Thr Asn Asn Gln Val Lys Val Thr
1               5                   10                  15

Lys Ala

<210> SEQ ID NO 104
<211> LENGTH: 20
<212> TYPE: PRT
<213> ORGANISM: Neisseria meningitidis

<400> SEQUENCE: 104

Pro Pro Ser Ser Asn Gln Gly Lys Asn Gln Ala Gln Thr Gly Asn Thr
1               5                   10                  15

Val Thr Lys Ala
            20

<210> SEQ ID NO 105
<211> LENGTH: 18
<212> TYPE: PRT
<213> ORGANISM: Neisseria meningitidis

<400> SEQUENCE: 105

Pro Pro Ser Lys Ser Gln Gly Lys Thr Gly Asn Gln Val Lys Val Thr
1               5                   10                  15

Lys Ala

<210> SEQ ID NO 106
<211> LENGTH: 18
<212> TYPE: PRT
<213> ORGANISM: Neisseria meningitidis

<400> SEQUENCE: 106

Pro Pro Ser Lys Ser Gln Gly Thr Asn Asn Gln Val Lys Val Thr
1               5                   10                  15

Lys Ala

<210> SEQ ID NO 107
<211> LENGTH: 18
<212> TYPE: PRT
<213> ORGANISM: Neisseria meningitidis

<400> SEQUENCE: 107

Pro Pro Ser Lys Ser Gln Pro Gly Gln Val Lys Val Thr Lys Val Thr
1               5                   10                  15

Lys Ala
```

<210> SEQ ID NO 108
<211> LENGTH: 24
<212> TYPE: PRT
<213> ORGANISM: Neisseria meningitidis

<400> SEQUENCE: 108

Gln Leu Gln Leu Thr Glu Gln Pro Ser Ser Thr Asn Gly Gln Thr Gly
1               5                   10                  15

Asn Gln Val Lys Val Thr Lys Ala
            20

<210> SEQ ID NO 109
<211> LENGTH: 24
<212> TYPE: PRT
<213> ORGANISM: Neisseria meningitidis

<400> SEQUENCE: 109

Gln Leu Gln Leu Thr Glu Ala Pro Ser Lys Ser Gln Gly Ala Ala Ser
1               5                   10                  15

Asn Gln Val Lys Val Thr Lys Ala
            20

<210> SEQ ID NO 110
<211> LENGTH: 19
<212> TYPE: PRT
<213> ORGANISM: Neisseria meningitidis

<400> SEQUENCE: 110

Ser Ala Tyr Thr Pro Ala His Val Tyr Val Asp Asn Lys Val Ala Lys
1               5                   10                  15

His Val Ala

<210> SEQ ID NO 111
<211> LENGTH: 21
<212> TYPE: PRT
<213> ORGANISM: Neisseria meningitidis

<400> SEQUENCE: 111

Ser Ala Tyr Thr Pro Ala His Phe Val Gln Asn Lys Gln Asn Asn Asn
1               5                   10                  15

Pro Thr Leu Val Pro
            20

<210> SEQ ID NO 112
<211> LENGTH: 12
<212> TYPE: PRT
<213> ORGANISM: Neisseria meningitidis

<400> SEQUENCE: 112

Val Glu Gly Arg Asn Tyr Gln Leu Gln Leu Thr Glu
1               5                   10

<210> SEQ ID NO 113
<211> LENGTH: 12
<212> TYPE: PRT
<213> ORGANISM: Neisseria meningitidis

<400> SEQUENCE: 113

Pro Ala Gln Asn Ser Lys Ser Ala Tyr Thr Pro Ala
1               5                   10

<210> SEQ ID NO 114
<211> LENGTH: 22

```
<212> TYPE: PRT
<213> ORGANISM: Neisseria meningitidis

<400> SEQUENCE: 114

Gln Leu Gln Leu Thr Glu Pro Pro Ser Lys Asn Gln Ala Gln Thr Gln
1               5                   10                  15

Asn Lys Val Thr Lys Ala
            20

<210> SEQ ID NO 115
<211> LENGTH: 16
<212> TYPE: PRT
<213> ORGANISM: Neisseria meningitidis

<400> SEQUENCE: 115

Gly Arg Asp Ala Phe Glu Leu Phe Leu Leu Gly Ser Gly Ser Asp Glu
1               5                   10                  15

<210> SEQ ID NO 116
<211> LENGTH: 31
<212> TYPE: PRT
<213> ORGANISM: Neisseria meningitidis

<400> SEQUENCE: 116

Arg His Ala Asn Val Gly Arg Asp Ala Phe Glu Leu Phe Leu Leu Gly
1               5                   10                  15

Ser Gly Ser Asp Glu Ala Lys Gly Thr Asp Pro Leu Lys Asn His
            20                  25                  30

<210> SEQ ID NO 117
<211> LENGTH: 18
<212> TYPE: PRT
<213> ORGANISM: Neisseria meningitidis

<400> SEQUENCE: 117

Gly Arg Asp Ala Phe Asn Leu Phe Leu Leu Gly Arg Ile Gly Asp Asp
1               5                   10                  15

Asp Glu

<210> SEQ ID NO 118
<211> LENGTH: 17
<212> TYPE: PRT
<213> ORGANISM: Neisseria meningitidis

<400> SEQUENCE: 118

Gly Arg Asn Ala Phe Glu Leu Phe Leu Ile Gly Ser Ala Thr Ser Asp
1               5                   10                  15

Gln

<210> SEQ ID NO 119
<211> LENGTH: 15
<212> TYPE: PRT
<213> ORGANISM: Neisseria meningitidis

<400> SEQUENCE: 119

Gln Val Lys Val Thr Lys Ala Lys Ser Arg Ile Arg Thr Lys Ile
1               5                   10                  15

<210> SEQ ID NO 120
<211> LENGTH: 13
<212> TYPE: PRT
<213> ORGANISM: Neisseria meningitidis
```

```
<400> SEQUENCE: 120

Thr Leu Val Pro Ala Val Val Gly Lys Pro Gly Ser Asp
1               5                   10

<210> SEQ ID NO 121
<211> LENGTH: 17
<212> TYPE: PRT
<213> ORGANISM: Neisseria meningitidis

<400> SEQUENCE: 121

His Ala Lys Ala Ser Ser Ser Leu Gly Ser Ala Lys Gly Phe Ser Pro
1               5                   10                  15

Arg

<210> SEQ ID NO 122
<211> LENGTH: 15
<212> TYPE: PRT
<213> ORGANISM: Neisseria meningitidis

<400> SEQUENCE: 122

Thr Arg Tyr Lys Asn Tyr Lys Ala Pro Ser Thr Asp Phe Lys Leu
1               5                   10                  15

<210> SEQ ID NO 123
<211> LENGTH: 18
<212> TYPE: PRT
<213> ORGANISM: Neisseria meningitidis

<400> SEQUENCE: 123

Ser Leu Asn Arg Ala Ser Val Asp Leu Gly Gly Ser Asp Ser Phe Ser
1               5                   10                  15

Gln Thr

<210> SEQ ID NO 124
<211> LENGTH: 21
<212> TYPE: PRT
<213> ORGANISM: Neisseria meningitidis

<400> SEQUENCE: 124

Gly Lys Val Asn Thr Val Lys Asn Val Arg Ser Gly Glu Leu Ser Ala
1               5                   10                  15

Gly Val Arg Val Lys
            20

<210> SEQ ID NO 125
<211> LENGTH: 21
<212> TYPE: PRT
<213> ORGANISM: Neisseria meningitidis

<400> SEQUENCE: 125

Gly Lys Val Asn Thr Val Lys Asn Val Arg Ser Gly Glu Leu Ser Val
1               5                   10                  15

Gly Val Arg Val Lys
            20

<210> SEQ ID NO 126
<211> LENGTH: 13
<212> TYPE: PRT
<213> ORGANISM: Homo sapiens

<400> SEQUENCE: 126

Ala Pro Glu Trp Pro Gly Ser Arg Asp Lys Arg Thr Leu
```

```
1               5              10
```

<210> SEQ ID NO 127
<211> LENGTH: 9
<212> TYPE: PRT
<213> ORGANISM: Homo sapiens

<400> SEQUENCE: 127

```
Glu Asp Gly Gln Val Met Asp Val Asp
1               5
```

<210> SEQ ID NO 128
<211> LENGTH: 8
<212> TYPE: PRT
<213> ORGANISM: Homo sapiens

<400> SEQUENCE: 128

```
Ser Thr Thr Gln Glu Gly Glu Leu
1               5
```

<210> SEQ ID NO 129
<211> LENGTH: 10
<212> TYPE: PRT
<213> ORGANISM: Homo sapiens

<400> SEQUENCE: 129

```
Gly His Thr Phe Glu Asp Ser Thr Lys Lys
1               5                  10
```

<210> SEQ ID NO 130
<211> LENGTH: 8
<212> TYPE: PRT
<213> ORGANISM: Homo sapiens

<400> SEQUENCE: 130

```
Gly Gly Gly His Phe Pro Pro Thr
1               5
```

<210> SEQ ID NO 131
<211> LENGTH: 6
<212> TYPE: PRT
<213> ORGANISM: Homo sapiens

<400> SEQUENCE: 131

```
Pro Gly Thr Ile Asn Ile
1               5
```

<210> SEQ ID NO 132
<211> LENGTH: 5
<212> TYPE: PRT
<213> ORGANISM: Homo sapiens

<400> SEQUENCE: 132

```
Phe Thr Pro Pro Thr
1               5
```

<210> SEQ ID NO 133
<211> LENGTH: 8
<212> TYPE: PRT
<213> ORGANISM: Homo sapiens

<400> SEQUENCE: 133

```
Ile Asn His Arg Gly Tyr Trp Val
1               5
```

```
<210> SEQ ID NO 134
<211> LENGTH: 17
<212> TYPE: PRT
<213> ORGANISM: Homo sapiens

<400> SEQUENCE: 134

Gly Glu Phe Cys Ile Asn His Arg Gly Tyr Trp Val Cys Gly Asp Pro
1               5                   10                  15
Ala

<210> SEQ ID NO 135
<211> LENGTH: 14
<212> TYPE: PRT
<213> ORGANISM: Homo sapiens

<400> SEQUENCE: 135

Met Ala Pro Glu Trp Pro Gly Ser Arg Asp Lys Arg Thr Leu
1               5                   10

<210> SEQ ID NO 136
<211> LENGTH: 10
<212> TYPE: PRT
<213> ORGANISM: Homo sapiens

<400> SEQUENCE: 136

Met Glu Asp Gly Gln Val Met Asp Val Asp
1               5                   10

<210> SEQ ID NO 137
<211> LENGTH: 9
<212> TYPE: PRT
<213> ORGANISM: Homo sapiens

<400> SEQUENCE: 137

Met Ser Thr Thr Gln Glu Gly Glu Leu
1               5

<210> SEQ ID NO 138
<211> LENGTH: 11
<212> TYPE: PRT
<213> ORGANISM: Homo sapiens

<400> SEQUENCE: 138

Met Gly His Thr Phe Glu Asp Ser Thr Lys Lys
1               5                   10

<210> SEQ ID NO 139
<211> LENGTH: 9
<212> TYPE: PRT
<213> ORGANISM: Homo sapiens

<400> SEQUENCE: 139

Met Gly Gly Gly His Phe Pro Pro Thr
1               5

<210> SEQ ID NO 140
<211> LENGTH: 7
<212> TYPE: PRT
<213> ORGANISM: Homo sapiens

<400> SEQUENCE: 140

Met Pro Gly Thr Ile Asn Ile
1               5
```

<210> SEQ ID NO 141
<211> LENGTH: 6
<212> TYPE: PRT
<213> ORGANISM: Homo sapiens

<400> SEQUENCE: 141

Met Phe Thr Pro Pro Thr
1               5

<210> SEQ ID NO 142
<211> LENGTH: 9
<212> TYPE: PRT
<213> ORGANISM: Homo sapiens

<400> SEQUENCE: 142

Met Ile Asn His Arg Gly Tyr Trp Val
1               5

<210> SEQ ID NO 143
<211> LENGTH: 18
<212> TYPE: PRT
<213> ORGANISM: Homo sapiens

<400> SEQUENCE: 143

Met Gly Glu Phe Cys Ile Asn His Arg Gly Tyr Trp Val Cys Gly Asp
1               5                   10                  15

Pro Ala

<210> SEQ ID NO 144
<211> LENGTH: 21
<212> TYPE: PRT
<213> ORGANISM: Hepatitis B virus

<400> SEQUENCE: 144

Met Gly Thr Asn Leu Ser Val Pro Asn Pro Leu Gly Phe Phe Pro Asp
1               5                   10                  15

His Gln Leu Asp Pro
            20

<210> SEQ ID NO 145
<211> LENGTH: 8
<212> TYPE: PRT
<213> ORGANISM: Hepatitis B virus

<400> SEQUENCE: 145

Pro Leu Gly Phe Phe Pro Asp His
1               5

<210> SEQ ID NO 146
<211> LENGTH: 10
<212> TYPE: PRT
<213> ORGANISM: Hepatitis B virus

<400> SEQUENCE: 146

Pro Leu Gly Phe Phe Pro Asp His Gln Leu
1               5                   10

<210> SEQ ID NO 147
<211> LENGTH: 26
<212> TYPE: PRT
<213> ORGANISM: Hepatitis B virus

<400> SEQUENCE: 147

Met Gln Trp Asn Ser Thr Ala Phe His Gln Thr Leu Gln Asp Pro Arg
1               5                   10                  15

Val Arg Gly Leu Tyr Leu Pro Ala Gly Gly
            20                  25

<210> SEQ ID NO 148
<211> LENGTH: 15
<212> TYPE: PRT
<213> ORGANISM: Hepatitis B virus

<400> SEQUENCE: 148

Met Gln Trp Asn Ser Thr Ala Phe His Gln Thr Leu Gln Asp Pro
1               5                   10                  15

<210> SEQ ID NO 149
<211> LENGTH: 15
<212> TYPE: PRT
<213> ORGANISM: Hepatitis B virus

<400> SEQUENCE: 149

Met Gln Trp Asn Ser Thr Ala Leu His Gln Ala Leu Gln Asp Pro
1               5                   10                  15

<210> SEQ ID NO 150
<211> LENGTH: 6
<212> TYPE: PRT
<213> ORGANISM: Hepatitis B virus

<400> SEQUENCE: 150

Gln Asp Pro Arg Val Arg
1               5

<210> SEQ ID NO 151
<211> LENGTH: 6
<212> TYPE: PRT
<213> ORGANISM: Hepatitis B virus

<400> SEQUENCE: 151

Gln Asp Gly Arg Val Arg
1               5

<210> SEQ ID NO 152
<211> LENGTH: 13
<212> TYPE: PRT
<213> ORGANISM: Hepatitis B virus

<400> SEQUENCE: 152

Asp Pro Arg Val Arg Gly Leu Tyr Leu Pro Ala Gly Gly
1               5                   10

<210> SEQ ID NO 153
<211> LENGTH: 13
<212> TYPE: PRT
<213> ORGANISM: Hepatitis B virus

<400> SEQUENCE: 153

Asp Pro Arg Val Arg Gly Leu Tyr Phe Pro Ala Gly Gly
1               5                   10

<210> SEQ ID NO 154
<211> LENGTH: 7
<212> TYPE: PRT
<213> ORGANISM: Artificial Sequence
<220> FEATURE:
<223> OTHER INFORMATION: linker peptide

```
<400> SEQUENCE: 154

Gly Ser Gly Asp Glu Gly Gly
1               5

<210> SEQ ID NO 155
<211> LENGTH: 10
<212> TYPE: PRT
<213> ORGANISM: Artificial Sequence
<220> FEATURE:
<223> OTHER INFORMATION: flexible linker arm

<400> SEQUENCE: 155

Gly Gly Gly Gly Ser Gly Gly Gly Gly Thr
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Flexible linker arm sequence

<400> SEQUENCE: 156

Gly Gly Gly Gly Ser Gly Gly Gly Gly
1               5

<210> SEQ ID NO 157
<211> LENGTH: 8
<212> TYPE: PRT
<213> ORGANISM: Artificial Sequence
<220> FEATURE:
<223> OTHER INFORMATION: Flexible linker arm sequence

<400> SEQUENCE: 157

Gly Gly Gly Gly Ser Gly Gly Gly
1               5

<210> SEQ ID NO 158
<211> LENGTH: 16
<212> TYPE: PRT
<213> ORGANISM: HIV

<400> SEQUENCE: 158

Gly Pro Lys Glu Pro Phe Arg Asp Tyr Val Asp Arg Phe Tyr Lys Cys
1               5                   10                  15

<210> SEQ ID NO 159
<211> LENGTH: 17
<212> TYPE: PRT
<213> ORGANISM: Corynebacterium diphtheriae

<400> SEQUENCE: 159

Phe Gln Val Val His Asn Ser Tyr Asn Arg Pro Ala Tyr Ser Pro Gly
1               5                   10                  15

Cys

<210> SEQ ID NO 160
<211> LENGTH: 25
<212> TYPE: PRT
<213> ORGANISM: Borrelia burgdorferi

<400> SEQUENCE: 160

Val Glu Ile Lys Glu Gly Thr Val Thr Leu Lys Arg Glu Ile Asp Lys
1               5                   10                  15
```

```
Asn Gly Lys Val Thr Val Ser Leu Cys
         20                  25

<210> SEQ ID NO 161
<211> LENGTH: 19
<212> TYPE: PRT
<213> ORGANISM: Borrelia burgdorferi

<400> SEQUENCE: 161

Thr Leu Ser Lys Asn Ile Ser Lys Ser Gly Glu Val Ser Val Glu Leu
1               5                   10                  15

Asn Asp Cys

<210> SEQ ID NO 162
<211> LENGTH: 11
<212> TYPE: PRT
<213> ORGANISM: Influenza A virus

<400> SEQUENCE: 162

Ser Ser Val Ser Ser Phe Glu Arg Phe Glu Cys
1               5                   10

<210> SEQ ID NO 163
<211> LENGTH: 10
<212> TYPE: PRT
<213> ORGANISM: Influenza A virus

<400> SEQUENCE: 163

Leu Ile Asp Ala Leu Leu Gly Asp Pro Cys
1               5                   10

<210> SEQ ID NO 164
<211> LENGTH: 9
<212> TYPE: PRT
<213> ORGANISM: Influenza A virus

<400> SEQUENCE: 164

Thr Leu Ile Asp Ala Leu Leu Gly Cys
1               5

<210> SEQ ID NO 165
<211> LENGTH: 21
<212> TYPE: PRT
<213> ORGANISM: Trypanosoma cruzi

<400> SEQUENCE: 165

Ser His Asn Phe Thr Leu Val Ala Ser Val Ile Ile Glu Glu Ala Pro
1               5                   10                  15

Ser Gly Asn Thr Cys
            20

<210> SEQ ID NO 166
<211> LENGTH: 16
<212> TYPE: PRT
<213> ORGANISM: Plasmodium falciparum

<400> SEQUENCE: 166

Ser Val Gln Ile Pro Lys Val Pro Tyr Pro Asn Gly Ile Val Tyr Cys
1               5                   10                  15

<210> SEQ ID NO 167
<211> LENGTH: 16
<212> TYPE: PRT
```

-continued

<210> SEQ ID NO 167
<211> LENGTH: (not shown)
<212> TYPE: PRT
<213> ORGANISM: Plasmodium falciparum

<400> SEQUENCE: 167

Asp Phe Asn His Tyr Tyr Thr Leu Lys Thr Gly Leu Glu Ala Asp Cys
1               5                   10                  15

<210> SEQ ID NO 168
<211> LENGTH: 18
<212> TYPE: PRT
<213> ORGANISM: Plasmodium falciparum

<400> SEQUENCE: 168

Pro Ser Asp Lys His Ile Glu Gln Tyr Lys Lys Ile Lys Asn Ser Ile
1               5                   10                  15

Ser Cys

<210> SEQ ID NO 169
<211> LENGTH: 20
<212> TYPE: PRT
<213> ORGANISM: Plasmodium falciparum

<400> SEQUENCE: 169

Glu Tyr Leu Asn Lys Ile Gln Asn Ser Leu Ser Thr Glu Trp Ser Pro
1               5                   10                  15

Cys Ser Val Thr
            20

<210> SEQ ID NO 170
<211> LENGTH: 19
<212> TYPE: PRT
<213> ORGANISM: Plasmodium vivax

<400> SEQUENCE: 170

Tyr Leu Asp Lys Val Arg Ala Thr Val Gly Thr Glu Trp Thr Pro Cys
1               5                   10                  15

Ser Val Thr

<210> SEQ ID NO 171
<211> LENGTH: 20
<212> TYPE: PRT
<213> ORGANISM: Plasmodium yoelii

<400> SEQUENCE: 171

Glu Phe Val Lys Gln Ile Ser Ser Gln Leu Thr Glu Glu Trp Ser Gln
1               5                   10                  15

Cys Ser Val Thr
            20

<210> SEQ ID NO 172
<211> LENGTH: 16
<212> TYPE: PRT
<213> ORGANISM: Streptococcus sobrinus

<400> SEQUENCE: 172

Lys Pro Arg Pro Ile Tyr Glu Ala Lys Leu Ala Gln Asn Gln Lys Cys
1               5                   10                  15

<210> SEQ ID NO 173
<211> LENGTH: 17
<212> TYPE: PRT
<213> ORGANISM: Streptococcus sobrinus

<400> SEQUENCE: 173

-continued

Ala Lys Ala Asp Tyr Glu Ala Lys Leu Ala Gln Tyr Glu Lys Asp Leu
1               5                   10                  15

Cys

<210> SEQ ID NO 174
<211> LENGTH: 16
<212> TYPE: PRT
<213> ORGANISM: Lymphocytic choriomeningitis virus

<400> SEQUENCE: 174

Arg Pro Gln Ala Ser Gly Val Tyr Met Gly Asn Leu Thr Ala Gln Cys
1               5                   10                  15

<210> SEQ ID NO 175
<211> LENGTH: 16
<212> TYPE: PRT
<213> ORGANISM: Clostridium tetani

<400> SEQUENCE: 175

Gln Tyr Ile Lys Ala Asn Ser Lys Phe Ile Gly Ile Thr Glu Leu Cys
1               5                   10                  15

<210> SEQ ID NO 176
<211> LENGTH: 19
<212> TYPE: PRT
<213> ORGANISM: Neisseria meningitidis

<400> SEQUENCE: 176

Ala Ile Trp Gln Val Glu Gln Lys Ala Ser Ile Ala Gly Thr Asp Ser
1               5                   10                  15

Gly Trp Cys

<210> SEQ ID NO 177
<211> LENGTH: 19
<212> TYPE: PRT
<213> ORGANISM: Neisseria meningitidis

<400> SEQUENCE: 177

Asn Tyr Lys Asn Gly Gly Phe Phe Val Gln Tyr Gly Gly Ala Tyr Lys
1               5                   10                  15

Arg His Cys

<210> SEQ ID NO 178
<211> LENGTH: 19
<212> TYPE: PRT
<213> ORGANISM: Neisseria meningitidis

<400> SEQUENCE: 178

His Asn Ser Gln Thr Glu Val Ala Ala Thr Leu Ala Tyr Arg Phe Gly
1               5                   10                  15

Asn Val Cys

<210> SEQ ID NO 179
<211> LENGTH: 19
<212> TYPE: PRT
<213> ORGANISM: Neisseria meningitidis

<400> SEQUENCE: 179

Thr Pro Arg Val Ser Tyr Ala His Gly Phe Lys Gly Leu Val Asp Asp
1               5                   10                  15

Ala Asp Cys

```
<210> SEQ ID NO 180
<211> LENGTH: 19
<212> TYPE: PRT
<213> ORGANISM: Neisseria meningitidis

<400> SEQUENCE: 180

Arg Phe Gly Asn Ala Val Pro Arg Ile Ser Tyr Ala His Gly Phe Asp
1               5                   10                  15

Phe Ile Cys

<210> SEQ ID NO 181
<211> LENGTH: 19
<212> TYPE: PRT
<213> ORGANISM: Neisseria meningitidis

<400> SEQUENCE: 181

Ala Phe Lys Tyr Ala Arg His Ala Asn Val Gly Arg Asn Ala Phe Glu
1               5                   10                  15

Leu Phe Cys

<210> SEQ ID NO 182
<211> LENGTH: 20
<212> TYPE: PRT
<213> ORGANISM: Neisseria meningitidis

<400> SEQUENCE: 182

Ser Gly Ala Trp Leu Lys Arg Asn Thr Gly Ile Gly Asn Tyr Thr Gln
1               5                   10                  15

Ile Asn Ala Cys
            20

<210> SEQ ID NO 183
<211> LENGTH: 16
<212> TYPE: PRT
<213> ORGANISM: Neisseria meningitidis

<400> SEQUENCE: 183

Ala Gly Glu Phe Gly Thr Leu Arg Ala Gly Arg Val Ala Asn Gln Cys
1               5                   10                  15

<210> SEQ ID NO 184
<211> LENGTH: 16
<212> TYPE: PRT
<213> ORGANISM: Neisseria meningitidis

<400> SEQUENCE: 184

Ile Gly Asn Tyr Thr Gln Ile Asn Ala Ala Ser Val Gly Leu Arg Cys
1               5                   10                  15

<210> SEQ ID NO 185
<211> LENGTH: 16
<212> TYPE: PRT
<213> ORGANISM: Neisseria meningitidis

<400> SEQUENCE: 185

Gly Arg Asn Tyr Gln Leu Gln Leu Thr Glu Gln Pro Ser Arg Thr Cys
1               5                   10                  15

<210> SEQ ID NO 186
<211> LENGTH: 16
<212> TYPE: PRT
<213> ORGANISM: Neisseria meningitidis
```

```
<400> SEQUENCE: 186

Ser Gly Ser Val Gln Phe Val Pro Ala Gln Asn Ser Lys Ser Ala Cys
1               5                   10                  15

<210> SEQ ID NO 187
<211> LENGTH: 16
<212> TYPE: PRT
<213> ORGANISM: Neisseria meningitidis

<400> SEQUENCE: 187

His Ala Asn Val Gly Arg Asp Ala Phe Asn Leu Phe Leu Leu Gly Cys
1               5                   10                  15

<210> SEQ ID NO 188
<211> LENGTH: 16
<212> TYPE: PRT
<213> ORGANISM: Neisseria meningitidis

<400> SEQUENCE: 188

Leu Gly Arg Ile Gly Asp Asp Glu Ala Lys Gly Thr Asp Pro Cys
1               5                   10                  15

<210> SEQ ID NO 189
<211> LENGTH: 16
<212> TYPE: PRT
<213> ORGANISM: Neisseria meningitidis

<400> SEQUENCE: 189

Ser Val Gln Phe Val Pro Ala Gln Asn Ser Lys Ser Ala Tyr Lys Cys
1               5                   10                  15

<210> SEQ ID NO 190
<211> LENGTH: 16
<212> TYPE: PRT
<213> ORGANISM: Neisseria meningitidis

<400> SEQUENCE: 190

Asn Tyr Ala Phe Lys Tyr Ala Lys His Ala Asn Val Gly Arg Asp Cys
1               5                   10                  15

<210> SEQ ID NO 191
<211> LENGTH: 16
<212> TYPE: PRT
<213> ORGANISM: Neisseria meningitidis

<400> SEQUENCE: 191

Ala His Gly Phe Asp Phe Ile Glu Arg Gly Lys Lys Gly Glu Asn Cys
1               5                   10                  15

<210> SEQ ID NO 192
<211> LENGTH: 16
<212> TYPE: PRT
<213> ORGANISM: Neisseria meningitidis

<400> SEQUENCE: 192

Gly Val Asp Tyr Asp Phe Ser Lys Arg Thr Ser Ala Ile Val Ser Cys
1               5                   10                  15

<210> SEQ ID NO 193
<211> LENGTH: 16
<212> TYPE: PRT
<213> ORGANISM: Neisseria meningitidis

<400> SEQUENCE: 193
```

```
His Asp Asp Met Pro Val Ser Val Arg Tyr Asp Ser Pro Asp Phe Cys
1               5                   10                  15

<210> SEQ ID NO 194
<211> LENGTH: 27
<212> TYPE: PRT
<213> ORGANISM: Neisseria meningitidis

<400> SEQUENCE: 194

Arg Phe Gly Asn Ala Val Pro Arg Ile Ser Tyr Ala His Gly Phe Asp
1               5                   10                  15

Phe Ile Glu Arg Gly Lys Lys Gly Glu Asn Cys
            20                  25

<210> SEQ ID NO 195
<211> LENGTH: 24
<212> TYPE: PRT
<213> ORGANISM: Neisseria meningitidis

<400> SEQUENCE: 195

Asn Tyr Ala Phe Lys Tyr Ala Lys His Ala Asn Val Gly Arg Asp Ala
1               5                   10                  15

Phe Asn Leu Phe Leu Leu Gly Cys
            20

<210> SEQ ID NO 196
<211> LENGTH: 26
<212> TYPE: PRT
<213> ORGANISM: Neisseria meningitidis

<400> SEQUENCE: 196

Ser Gly Ala Trp Leu Lys Arg Asn Thr Gly Ile Gly Asn Tyr Thr Gln
1               5                   10                  15

Ile Asn Ala Ala Ser Val Gly Leu Arg Cys
            20                  25

<210> SEQ ID NO 197
<211> LENGTH: 20
<212> TYPE: PRT
<213> ORGANISM: Neisseria meningitidis

<400> SEQUENCE: 197

Ser Gly Ser Val Gln Phe Val Pro Ala Gln Asn Ser Lys Ser Ala Tyr
1               5                   10                  15

Thr Pro Ala Cys
            20

<210> SEQ ID NO 198
<211> LENGTH: 19
<212> TYPE: PRT
<213> ORGANISM: Neisseria meningitidis

<400> SEQUENCE: 198

Thr Gly Ala Asn Asn Thr Ser Thr Val Ser Asp Tyr Phe Arg Asn Arg
1               5                   10                  15

Ile Thr Cys

<210> SEQ ID NO 199
<211> LENGTH: 19
<212> TYPE: PRT
<213> ORGANISM: Neisseria meningitidis
```

```
<400> SEQUENCE: 199

Ile Tyr Asp Phe Lys Leu Asn Asp Lys Phe Asp Lys Phe Lys Pro Tyr
1               5                   10                  15

Ile Gly Cys

<210> SEQ ID NO 200
<211> LENGTH: 19
<212> TYPE: PRT
<213> ORGANISM: Neisseria meningitidis

<400> SEQUENCE: 200

Leu Ser Ala Ile Tyr Asp Phe Lys Leu Asn Asp Lys Phe Lys Pro Tyr
1               5                   10                  15

Ile Gly Cys

<210> SEQ ID NO 201
<211> LENGTH: 19
<212> TYPE: PRT
<213> ORGANISM: Neisseria meningitidis

<400> SEQUENCE: 201

Asn Gly Trp Tyr Ile Asn Pro Trp Ser Glu Val Lys Phe Asp Leu Asn
1               5                   10                  15

Ser Arg Cys

<210> SEQ ID NO 202
<211> LENGTH: 549
<212> TYPE: DNA
<213> ORGANISM: Hepatitis B virus

<400> SEQUENCE: 202
atggacatcg acccttataa agaatttgga gctactgtgg agttactctc gttttttgcct    60 tctgacttct ttccttcagt acgagatctt ctagataccg cctcagctct gtatcgggaa   120
gccttagagt ctcctgagca ttgttcacct caccatactg cactcaggca agcaattctt   180 tgctggggggg aactaatgac tctagctacc tgggtgggtg ttaatttgga agatccagcg   240
tctagagacc tagtagtcag ttatgtcaac actaatatgg gcctaaagtt caggcaactc   300
ttgtggtttc acatttcttg tctcactttt ggaagagaaa cagttataga gtatttggtg   360
tctttcggag tgtggattcg cactcctcca gcttatagac caccaaatgc ccctatccta   420
tcaacacttc cggagactac tgttgttaga cgacgaggg ggtcccctag aagaagaact   480
ccctcgcctc gcagacgaag gtctcaatcg ccgcgtcgca gaagatctca atctcgggaa   540
tctcaatgt                                                           549

<210> SEQ ID NO 203
<211> LENGTH: 555
<212> TYPE: DNA
<213> ORGANISM: Hepatitis B virus

<400> SEQUENCE: 203
atggacattg acccttataa agaatttgga gctactgtgg agttactctc gttttttgcct    60 tctgacttct ttccttccgt acgagatctc ctagacaccg cctcagctct gtatcgagaa   120
gccttagagt ctcctgagca ttgctcacct caccatactg cactcaggca agccattctc   180 tgctggggggg aattgatgac tctagctacc tgggtgggta ataatttgca agatccagca   240
tccagagatc tagtagtcaa ttatgttaat actaacatgg gtttaaagat caggcaacta   300
```

```
ttgtggtttc atatatcttg ccttactttt ggaagagaga ctgtacttga atatttggtc    360
tctttcggag tgtggattcg cactcctcca gcctatagac caccaaatgc ccctatctta    420
tcaacacttc cggaaactac tgttgttaga cgacgggacc gaggcaggtc cctagaaga    480 agaactccct cgcctcgcag acgcagatct caatcgccgc gtcgcagaag atctcaatct    540
cgggaatctc aatgt                                                    555
```

<210> SEQ ID NO 204
<211> LENGTH: 555
<212> TYPE: DNA
<213> ORGANISM: Hepatitis B virus

<400> SEQUENCE: 204

```
atggacattg acccttataa agaatttgga gctactgtgg agttactctc gttttttgcct   60 tctgacttct ttccttccgt cagagatctc ctagacaccg cctcagctct gtatcgagaa   120
gccttagagt ctcctgagca ttgctcacct caccatactg cactcaggca agccattctc   180
tgctgggggg aattgatgac tctagctacc tgggtgggta ataatttgga agatccagca   240
tctagggatc ttgtagtaaa ttatgttaat actaacgtgg gtttaaagat caggcaacta   300
ttgtggtttc atatatcttg ccttactttt ggaagagaga ctgtacttga atatttggtc   360
tctttcggag tgtggattcg cactcctcca gcctatagac caccaaatgc ccctatctta   420
tcaacacttc cggaaactac tgttgttaga cgacgggacc gaggcaggtc cctagaaga   480 agaactccct cgcctcgcag acgcagatct ccatcgccgc gtcgcagaag atctcaatct   540
cgggaatctc aatgt                                                   555
```

<210> SEQ ID NO 205
<211> LENGTH: 549
<212> TYPE: DNA
<213> ORGANISM: Hepatitis B virus

<400> SEQUENCE: 205

```
atggacattg acccttataa agaatttgga gctactgtgg agttactctc gttttttgcct   60 tctgacttct ttccttccgt acgagatctt ctagataccg ccgcagctct gtatcgggat   120
gccttagagt ctcctgagca ttgttcacct caccatactg cactcaggca agcaattctt   180
tgctggggag acttaatgac tctagctacc tgggtgggta ctaatttaga agatccagca   240
tctagggacc tagtagtcag ttatgtcaac actaatgtgg gcctaaagtt cagacaatta   300
ttgtggtttc acatttcttg tctcactttt ggaagagaaa cggttctaga gtatttggtg   360
tcttttggag tgtggattcg cactcctcca gcttatagac caccaaatgc ccctatccta   420
tcaacgcttc cggagactac tgttgttaga cgacgaggca ggtcccctag aagaagaact   480
ccctcgcctc gcagacgaag atctcaatcg ccgcgtcgca agatctca atctcgggaa   540 tctcaatgt                                                          549
```

<210> SEQ ID NO 206
<211> LENGTH: 549
<212> TYPE: DNA
<213> ORGANISM: Marmota monax

<400> SEQUENCE: 206

```
atggctttgg ggcatggaca tagatcctta taaagaattt ggttcatctt atcagttgtt   60 gaatttctt cctttggact tctttcctga tcttaatgct ttggtggaca ctgctactgc   120
cttgtatgaa gaagaactaa caggtaggga acattgctct ccgcaccata cagctattag   180
```

-continued

```
acaagcttta gtatgctggg atgaattaac taaattgata gcttggatga gctctaacat    240
aacttctgaa caagtaagaa caatcattgt aaatcatgtc aatgatacct ggggacttaa    300
ggtgagacaa agtttatggt ttcatttgtc atgtctcact ttcggacaac atacagttca    360
agaattttta gtaagttttg gagtatggat caggactcca gctccatata gacctcctaa    420
tgcacccatt ctctcgactc ttccggaaca tacagtcatt aggagaagag gaggtgcaag    480
agcttctagg tcccccagaa gacgcactcc ctctcctcgc aggagaagat ctcaatcacc    540
gcgtcgcag                                                            549
```

<210> SEQ ID NO 207
<211> LENGTH: 651
<212> TYPE: DNA
<213> ORGANISM: Spermophilus variegatus

<400> SEQUENCE: 207

```
atgtatcttt ttcacctgtg ccttgttttt gcctgtgttc catgtcctac tgttcaagcc     60
tccaagctgt gccttggatg gctttgggac atggacatag atccctataa agaatttggt    120
tcttcttatc agttgttgaa ttttcttcct ttggactttt ttcctgatct caatgcattg    180
gtggacactg ctgctgctct ttatgaagaa gaattaacag gtagggagca ttgttctcct    240
catcatactg ctattagaca ggccttagtg tgttgggaag aattaactag attaattaca    300
tggatgagtg aaaatacaac agaagaagtt agaagaatta ttgttgatca tgtcaataat    360
acttggggac ttaaagtaag acagacttta tggtttcatt tatcatgtct tacttttgga    420
caacacacag ttcaagaatt tttggttagt tttggagtat ggattagaac tccagctcct    480
tatagaccac ctaatgcacc cattttatca actcttccgg aacatacagt cattaggaga    540
agaggaggtt caagagctgc taggtccccc cgaagacgca ctccctctcc tcgcaggaga    600
aggtctcaat caccgcgtcg cagacgctct caatctccag cttccaactg c             651
```

<210> SEQ ID NO 208
<211> LENGTH: 18
<212> TYPE: PRT
<213> ORGANISM: Artificial Sequence
<220> FEATURE:
<223> OTHER INFORMATION: Amplification primer containing a restriction endonuclease site

<400> SEQUENCE: 208

Gly Gly Thr Gly Cys Ala Thr Gly Cys Ala Ala Gly Gly Ala Gly Ala
1               5                   10                  15

Thr Gly

<210> SEQ ID NO 209
<211> LENGTH: 55
<212> TYPE: DNA
<213> ORGANISM: Artificial Sequence
<220> FEATURE:
<223> OTHER INFORMATION: Amplification primer containing a restriction endonuclease site

<400> SEQUENCE: 209

```
gcgaagcttc ggatcccatg gttttttcct ccttatgtga aattgttatc cgctc           55
```

<210> SEQ ID NO 210
<211> LENGTH: 24
<212> TYPE: DNA
<213> ORGANISM: Artificial Sequence

```
<220> FEATURE:
<223> OTHER INFORMATION: Amplification primer containing a restriction
      endonuclease site

<400> SEQUENCE: 210
ttgggccatg gacatcgacc ctta                                           24

<210> SEQ ID NO 211
<211> LENGTH: 29
<212> TYPE: DNA
<213> ORGANISM: Artificial Sequence
<220> FEATURE:
<223> OTHER INFORMATION: Amplification primer containing a restriction
      endonuclease site

<400> SEQUENCE: 211
gcggaattcc ttccaaatta acacccacc                                      29

<210> SEQ ID NO 212
<211> LENGTH: 38
<212> TYPE: DNA
<213> ORGANISM: Artificial Sequence
<220> FEATURE:
<223> OTHER INFORMATION: Amplification primer containing a restriction
      endonuclease site

<400> SEQUENCE: 212
cgcgaattca aaaagagctc gatccagcgt ctagagac                            38

<210> SEQ ID NO 213
<211> LENGTH: 31
<212> TYPE: DNA
<213> ORGANISM: Artificial Sequence
<220> FEATURE:
<223> OTHER INFORMATION: Amplification primer containing a restriction
      endonuclease site

<400> SEQUENCE: 213
cgcaagctta acaacagta gtctccggaa g                                    31

<210> SEQ ID NO 214
<211> LENGTH: 31
<212> TYPE: PRT
<213> ORGANISM: Artificial Sequence
<220> FEATURE:
<223> OTHER INFORMATION: Amplification primer containing a restriction
      endonuclease site

<400> SEQUENCE: 214

Gly Cys Gly Gly Ala Ala Thr Thr Cys Cys Ala Thr Cys Thr Thr Cys
1               5                   10                  15

Cys Ala Ala Ala Thr Thr Ala Ala Cys Ala Cys Cys Cys Ala Cys
            20                  25                  30

<210> SEQ ID NO 215
<211> LENGTH: 39
<212> TYPE: PRT
<213> ORGANISM: Artificial Sequence
<220> FEATURE:
<223> OTHER INFORMATION: Amplification primer containing a restriction
      endonuclease site

<400> SEQUENCE: 215

Cys Gly Cys Gly Ala Ala Thr Thr Cys Ala Ala Ala Ala Gly Ala
1               5                   10                  15

Gly Cys Thr Cys Cys Cys Ala Gly Cys Gly Thr Cys Thr Ala Gly Ala
```

```
            20                  25                  30
Gly Ala Cys Cys Thr Ala Gly
        35

<210> SEQ ID NO 216
<211> LENGTH: 12
<212> TYPE: PRT
<213> ORGANISM: Artificial Sequence
<220> FEATURE:
<223> OTHER INFORMATION: Amplification primer containing a restriction
      endonuclease site

<400> SEQUENCE: 216

Met Gly Cys Glu Leu Asp Pro Tyr Lys Glu Phe Gly
1               5                   10

<210> SEQ ID NO 217
<211> LENGTH: 40
<212> TYPE: DNA
<213> ORGANISM: Artificial Sequence
<220> FEATURE:
<223> OTHER INFORMATION: Amplification primer containing a restriction
      endonuclease site

<400> SEQUENCE: 217
gcgccatggg gtgtgagctc gacccttata aagaatttgg                              40

<210> SEQ ID NO 218
<211> LENGTH: 12
<212> TYPE: PRT
<213> ORGANISM: Artificial Sequence
<220> FEATURE:
<223> OTHER INFORMATION: Amplification primer containing a restriction
      endonuclease site

<400> SEQUENCE: 218

Met Gly Cys Asp Ile Asp Pro Tyr Lys Glu Phe Gly
1               5                   10

<210> SEQ ID NO 219
<211> LENGTH: 40
<212> TYPE: DNA
<213> ORGANISM: Artificial Sequence
<220> FEATURE:
<223> OTHER INFORMATION: Amplification primer containing a restriction
      endonuclease site

<400> SEQUENCE: 219
gcgccatggg gtgtgacatc gacccttata aagaatttgg                              40

<210> SEQ ID NO 220
<211> LENGTH: 42
<212> TYPE: DNA
<213> ORGANISM: Artificial Sequence
<220> FEATURE:
<223> OTHER INFORMATION: Amplification primer containing a restriction
      endonuclease site

<400> SEQUENCE: 220
cgcaagctta gagctcttga attccaacaa cagtagtctc cg                           42

<210> SEQ ID NO 221
<211> LENGTH: 28
<212> TYPE: DNA
<213> ORGANISM: Artificial Sequence
<220> FEATURE:
<223> OTHER INFORMATION: Amplification primer containing a restriction
``` endonuclease site

<400> SEQUENCE: 221
cgcgagctcc cagcgtctag agacctag                                      28

<210> SEQ ID NO 222
<211> LENGTH: 17
<212> TYPE: DNA
<213> ORGANISM: Artificial Sequence
<220> FEATURE:
<223> OTHER INFORMATION: Amplification primer containing a restriction
      endonuclease site

<400> SEQUENCE: 222
gtatcaggct gaaaatc                                                  17

<210> SEQ ID NO 223
<211> LENGTH: 19
<212> TYPE: PRT
<213> ORGANISM: Plasmodium falciparum

<400> SEQUENCE: 223

Ile Asn Ala Asn Pro Asn Ala Asn Pro Asn Ala Asn Pro Asn Ala Asn
1               5                   10                  15

Pro Glu Leu

<210> SEQ ID NO 224
<211> LENGTH: 57
<212> TYPE: DNA
<213> ORGANISM: Plasmodium falciparum

<400> SEQUENCE: 224
aattaacgct aatccgaacg ctaatccgaa cgctaatccg aacgctaatc cggagct     57

<210> SEQ ID NO 225
<211> LENGTH: 49
<212> TYPE: DNA
<213> ORGANISM: Plasmodium falciparum

<400> SEQUENCE: 225
ccggattagc gttcggatta gcgttcggat tagcgttcgg attagcgtt              49

<210> SEQ ID NO 226
<211> LENGTH: 31
<212> TYPE: PRT
<213> ORGANISM: Plasmodium falciparum

<400> SEQUENCE: 226

Ile Asn Ala Asn Pro Asn Val Asp Pro Asn Ala Asn Pro Asn Ala Asn
1               5                   10                  15

Pro Asn Ala Asn Pro Asn Val Asp Pro Asn Ala Asn Pro Glu Leu
                20                  25                  30

<210> SEQ ID NO 227
<211> LENGTH: 93
<212> TYPE: DNA
<213> ORGANISM: Plasmodium falciparum

<400> SEQUENCE: 227
aattaacgct aatccgaacg ttgacccgaa cgctaatccg aacgctaatc cgaacgctaa   60
tccgaacgtt gacccgaacg ctaatccgga gct                                93

<210> SEQ ID NO 228
<211> LENGTH: 92
<212> TYPE: DNA
<213> ORGANISM: Plasmodium falciparum

<400> SEQUENCE: 228
ggagctccgg attagcgttc gggtcaacgt tcggattagc gttcggatta gcgttcggat    60
tagcgttcgg gtccaacgtt cggattagcg tt    92

<210> SEQ ID NO 229
<211> LENGTH: 23
<212> TYPE: PRT
<213> ORGANISM: Plasmodium falciparum

<400> SEQUENCE: 229

Ile Asn Ala Asn Pro Asn Val Asp Pro Asn Ala Asn Pro Asn Ala Asn
1               5                   10                  15

Pro Asn Ala Asn Pro Glu Leu
            20

<210> SEQ ID NO 230
<211> LENGTH: 69
<212> TYPE: DNA
<213> ORGANISM: Plasmodium falciparum

<400> SEQUENCE: 230
aattaacgcg aatccgaacg tggatccgaa tgccaaccct aacgccaacc caaatgcgaa    60
cccagagct    69

<210> SEQ ID NO 231
<211> LENGTH: 61
<212> TYPE: DNA
<213> ORGANISM: Plasmodium falciparum

<400> SEQUENCE: 231
ctgggttcgc atttggggttg gcgttagggt tggcattcgg atccacgttc ggattcgcgt    60
t    61

<210> SEQ ID NO 232
<211> LENGTH: 23
<212> TYPE: PRT
<213> ORGANISM: Plasmodium falciparum

<400> SEQUENCE: 232

Ile Asn Ala Asn Pro Asn Ala Asn Pro Asn Ala Asn Pro Asn Val Asp
1               5                   10                  15

Pro Asn Ala Asn Pro Glu Leu
            20

<210> SEQ ID NO 233
<211> LENGTH: 69
<212> TYPE: DNA
<213> ORGANISM: Plasmodium falciparum

<400> SEQUENCE: 233
aattaacgcg aatccgaatg ccaaccctaa cgccaaccca acgtggatc cgaatgcgaa    60 cccagagct    69

<210> SEQ ID NO 234
<211> LENGTH: 61
<212> TYPE: DNA

-continued

<213> ORGANISM: Plasmodium falciparum

<400> SEQUENCE: 234

```
ctgggttcgc attcggatcc acgtttgggt tggcgttagg gttggcattc ggattcgcgt    60
t                                                                    61
```

<210> SEQ ID NO 235
<211> LENGTH: 31
<212> TYPE: PRT
<213> ORGANISM: Plasmodium falciparum

<400> SEQUENCE: 235

```
Ile Asn Ala Asn Pro Asn Val Asp Pro Asn Ala Asn Pro Asn Ala Asn
 1               5                  10                  15
Pro Asn Ala Asn Pro Asn Val Asp Pro Asn Ala Asn Pro Glu Leu
            20                  25                  30
```

<210> SEQ ID NO 236
<211> LENGTH: 93
<212> TYPE: DNA
<213> ORGANISM: Plasmodium falciparum

<400> SEQUENCE: 236

```
aattaacgcg aatccgaacg tggatccaaa tgccaaccct aacgctaatc caaacgccaa    60
cccgaatgtt gaccccaatg ccaatccgga gct                                 93
```

<210> SEQ ID NO 237
<211> LENGTH: 85
<212> TYPE: DNA
<213> ORGANISM: Plasmodium falciparum

<400> SEQUENCE: 237

```
ccggattggc attggggtca acattcgggt tggcgtttgg attagcgtta gggttggcat    60
ttggatccac gttcggattc gcgtt                                          85
```

<210> SEQ ID NO 238
<211> LENGTH: 23
<212> TYPE: PRT
<213> ORGANISM: Plasmodium falciparum

<400> SEQUENCE: 238

```
Ile Asn Pro Asn Val Asp Pro Asn Ala Asn Pro Asn Ala Asn Pro Asn
 1               5                  10                  15
Ala Asn Pro Asn Val Glu Leu
            20
```

<210> SEQ ID NO 239
<211> LENGTH: 69
<212> TYPE: DNA
<213> ORGANISM: Plasmodium falciparum

<400> SEQUENCE: 239

```
aattaatccg aacgtggatc caaatgccaa ccctaacgct aatccaaacg ccaacccgaa    60
tgttgagct                                                            69
```

<210> SEQ ID NO 240
<211> LENGTH: 61
<212> TYPE: DNA
<213> ORGANISM: Plasmodium falciparum

<400> SEQUENCE: 240

```
caacattcgg gttggcgttg ggattagcgt tagggttggc atttggatcc acgttcggat    60
t                                                                   61
```

<210> SEQ ID NO 241
<211> LENGTH: 25
<212> TYPE: PRT
<213> ORGANISM: Plasmodium falciparum

<400> SEQUENCE: 241

Ile Asn Pro Asn Val Asp Pro Asn Ala Asn Pro Asn Ala Asn Pro Asn
1               5                   10                  15

Ala Asn Pro Asn Val Asp Pro Glu Leu
            20                  25

<210> SEQ ID NO 242
<211> LENGTH: 75
<212> TYPE: DNA
<213> ORGANISM: Plasmodium falciparum

<400> SEQUENCE: 242

```
aattaatccg aacgtggatc caaatgccaa ccctaacgct aatccaaacg ccaacccgaa    60
tgttgaccct gagct                                                    75
```

<210> SEQ ID NO 243
<211> LENGTH: 67
<212> TYPE: DNA
<213> ORGANISM: Plasmodium falciparum

<400> SEQUENCE: 243

```
cagggtcaac attcggggttg gcgtttggat tagcgttagg gttggcattt ggatccacgt    60
tcggatt                                                             67
```

<210> SEQ ID NO 244
<211> LENGTH: 27
<212> TYPE: PRT
<213> ORGANISM: Plasmodium falciparum

<400> SEQUENCE: 244

Ile Asn Pro Asn Val Asp Pro Asn Ala Asn Pro Asn Ala Asn Pro Asn
1               5                   10                  15

Ala Asn Pro Asn Val Asp Pro Asn Ala Glu Leu
            20                  25

<210> SEQ ID NO 245
<211> LENGTH: 81
<212> TYPE: DNA
<213> ORGANISM: Plasmodium falciparum

<400> SEQUENCE: 245

```
aattaatccg aacgtggatc caaatgccaa ccctaacgct aatccaaacg ccaacccgaa    60
tgttgaccct aatgctgagc t                                             81
```

<210> SEQ ID NO 246
<211> LENGTH: 73
<212> TYPE: DNA
<213> ORGANISM: Plasmodium falciparum

<400> SEQUENCE: 246

```
cagcattagg gtcaacattc gggttggcgt ttggattagc gttagggttg gcatttggat    60
```

```
ccacgttcgg att                                                          73

<210> SEQ ID NO 247
<211> LENGTH: 21
<212> TYPE: PRT
<213> ORGANISM: Plasmodium falciparum

<400> SEQUENCE: 247

Ile Asn Val Asp Pro Asn Ala Asn Pro Asn Ala Asn Pro Asn Ala Asn
1               5                   10                  15

Pro Asn Val Glu Leu
            20

<210> SEQ ID NO 248
<211> LENGTH: 63
<212> TYPE: DNA
<213> ORGANISM: Plasmodium falciparum

<400> SEQUENCE: 248
aattaacgtg gatccaaatg ccaaccctaa cgctaatcca aacgccaacc cgaatgttga      60
gct                                                                   63

<210> SEQ ID NO 249
<211> LENGTH: 55
<212> TYPE: DNA
<213> ORGANISM: Plasmodium falciparum

<400> SEQUENCE: 249
caacattcgg gttggcgttt ggattagcgt tagggttggc atttggatcc acgtt           55

<210> SEQ ID NO 250
<211> LENGTH: 23
<212> TYPE: PRT
<213> ORGANISM: Plasmodium falciparum

<400> SEQUENCE: 250

Ile Asn Val Asp Pro Asn Ala Asn Pro Asn Ala Asn Pro Asn Ala Asn
1               5                   10                  15

Pro Asn Val Asp Pro Glu Leu
            20

<210> SEQ ID NO 251
<211> LENGTH: 69
<212> TYPE: DNA
<213> ORGANISM: Plasmodium falciparum

<400> SEQUENCE: 251
aattaacgtg gatccaaatg ccaaccctaa cgctaatcca aacgccaacc cgaatgttga      60
ccctgagct                                                             69

<210> SEQ ID NO 252
<211> LENGTH: 61
<212> TYPE: DNA
<213> ORGANISM: Plasmodium falciparum

<400> SEQUENCE: 252
cagggtcaac attcgggttg gcgtttggat tagcgttagg gttggcattt ggatccacgt      60
t                                                                     61

<210> SEQ ID NO 253
<211> LENGTH: 25
```

```
<212> TYPE: PRT
<213> ORGANISM: Plasmodium falciparum

<400> SEQUENCE: 253

Ile Asn Val Asp Pro Asn Ala Asn Pro Asn Ala Asn Pro Asn Ala Asn
1               5                   10                  15
Pro Asn Val Asp Pro Asn Ala Glu Leu
            20                  25

<210> SEQ ID NO 254
<211> LENGTH: 75
<212> TYPE: DNA
<213> ORGANISM: Plasmodium falciparum

<400> SEQUENCE: 254
aattaacgtg gatccaaatg ccaaccctaa cgctaatcca aacgccaacc cgaatgttga      60
ccctaatgct gagct                                                      75

<210> SEQ ID NO 255
<211> LENGTH: 67
<212> TYPE: DNA
<213> ORGANISM: Plasmodium falciparum

<400> SEQUENCE: 255
cagcattagg gtcaacattc gggttggcgt ttggattagc gttaggttg gcatttggat       60 ccacgtt                                                               67

<210> SEQ ID NO 256
<211> LENGTH: 19
<212> TYPE: PRT
<213> ORGANISM: Plasmodium falciparum

<400> SEQUENCE: 256

Ile Asp Pro Asn Ala Asn Pro Asn Ala Asn Pro Asn Ala Asn Pro Asn
1               5                   10                  15
Val Glu Leu

<210> SEQ ID NO 257
<211> LENGTH: 57
<212> TYPE: DNA
<213> ORGANISM: Plasmodium falciparum

<400> SEQUENCE: 257
aattgatcca atgccaacc ctaacgctaa tccaaacgcc aacccgaatg ttgagct          57

<210> SEQ ID NO 258
<211> LENGTH: 49
<212> TYPE: DNA
<213> ORGANISM: Plasmodium falciparum

<400> SEQUENCE: 258
caacattcgg gttggcgttt ggattagcgt tagggttggc atttggatc                  49

<210> SEQ ID NO 259
<211> LENGTH: 21
<212> TYPE: PRT
<213> ORGANISM: Plasmodium falciparum

<400> SEQUENCE: 259

Ile Asp Pro Asn Ala Asn Pro Asn Ala Asn Pro Asn Ala Asn Pro Asn
1               5                   10                  15
```

-continued

Val Asp Pro Glu Leu
            20

<210> SEQ ID NO 260
<211> LENGTH: 63
<212> TYPE: DNA
<213> ORGANISM: Plasmodium falciparum

<400> SEQUENCE: 260
aattgatcca aatgccaacc ctaacgctaa tccaaacgcc aacccgaatg ttgaccctga    60
gct                                                                  63

<210> SEQ ID NO 261
<211> LENGTH: 55
<212> TYPE: DNA
<213> ORGANISM: Plasmodium falciparum

<400> SEQUENCE: 261
cagggtcaac attcgggttg gcgtttggat tagcgttagg gttggcattt ggatc          55

<210> SEQ ID NO 262
<211> LENGTH: 23
<212> TYPE: PRT
<213> ORGANISM: Plasmodium falciparum

<400> SEQUENCE: 262

Ile Asp Pro Asn Ala Asn Pro Asn Ala Asn Pro Asn Ala Asn Pro Asn
1               5                   10                  15

Val Asp Pro Asn Ala Glu Leu
            20

<210> SEQ ID NO 263
<211> LENGTH: 69
<212> TYPE: DNA
<213> ORGANISM: Plasmodium falciparum

<400> SEQUENCE: 263
aattgatcca aatgccaacc ctaacgctaa tccaaacgcc aacccgaatg ttgaccctaa    60
tgccgagct                                                            69

<210> SEQ ID NO 264
<211> LENGTH: 61
<212> TYPE: DNA
<213> ORGANISM: Plasmodium falciparum

<400> SEQUENCE: 264
cggcattagg gtcaacattc gggttggcgt ttggattagc gttagggttg gcatttggat    60
c                                                                    61

<210> SEQ ID NO 265
<211> LENGTH: 21
<212> TYPE: PRT
<213> ORGANISM: Plasmodium falciparum

<400> SEQUENCE: 265

Ile Glu Tyr Leu Asn Lys Ile Gln Asn Ser Leu Ser Thr Glu Trp Ser
1               5                   10                  15

Pro Cys Ser Val Thr
            20

<210> SEQ ID NO 266

<211> LENGTH: 69
<212> TYPE: DNA
<213> ORGANISM: Plasmodium falciparum

<400> SEQUENCE: 266
aattgaatat ctgaacaaaa tccagaactc tctgtccacc gaatggtctc cgtgctccgt    60
tacctagta                                                           69

<210> SEQ ID NO 267
<211> LENGTH: 69
<212> TYPE: DNA
<213> ORGANISM: Plasmodium falciparum

<400> SEQUENCE: 267
agcttactag gtaacggagc acggagacaa ttcggtggac agagagttct ggattttgtt    60
cagatattc                                                           69

<210> SEQ ID NO 268
<211> LENGTH: 24
<212> TYPE: PRT
<213> ORGANISM: Plasmodium vivax

<400> SEQUENCE: 268

Ile Pro Ala Gly Asp Arg Ala Asp Gly Gln Pro Ala Gly Asp Arg Ala
1               5                   10                  15

Ala Gly Gln Pro Ala Gly Glu Leu
            20

<210> SEQ ID NO 269
<211> LENGTH: 72
<212> TYPE: DNA
<213> ORGANISM: Plasmodium vivax

<400> SEQUENCE: 269
aattccggct ggtgaccgtg cagatggcca gccagcgggt gaccgcgctg caggccagcc    60
ggctggcgag ct                                                       72

<210> SEQ ID NO 270
<211> LENGTH: 64
<212> TYPE: DNA
<213> ORGANISM: Plasmodium vivax

<400> SEQUENCE: 270
cgccagccgg ctggcctgca gcgcggtcac ccgctggctg gccatctgca cggtcaccag    60
ccgg                                                                64

<210> SEQ ID NO 271
<211> LENGTH: 21
<212> TYPE: PRT
<213> ORGANISM: Plasmodium vivax

<400> SEQUENCE: 271

Ile Asp Arg Ala Ala Gly Gln Pro Ala Gly Asp Arg Ala Asp Gly Gln
1               5                   10                  15

Pro Ala Gly Glu Leu
            20

<210> SEQ ID NO 272
<211> LENGTH: 63
<212> TYPE: DNA
<213> ORGANISM: Plasmodium vivax -continued

<400> SEQUENCE: 272
aattgacaga gcagccggac aaccagcagg cgatcgagca gacggacagc ccgcagggga    60
gct                                                                 63

<210> SEQ ID NO 273
<211> LENGTH: 55
<212> TYPE: DNA
<213> ORGANISM: Plasmodium vivax

<400> SEQUENCE: 273
cccctgcggg ctgtccgtct gctcgatcgc ctgctggttg tccggctgct ctgtc         55

<210> SEQ ID NO 274
<211> LENGTH: 21
<212> TYPE: PRT
<213> ORGANISM: Plasmodium vivax

<400> SEQUENCE: 274

Ile Ala Asn Gly Ala Gly Asn Gln Pro Gly Ala Asn Gly Ala Gly Asp
1               5                   10                  15

Gln Pro Gly Glu Leu
            20

<210> SEQ ID NO 275
<211> LENGTH: 63
<212> TYPE: DNA
<213> ORGANISM: Plasmodium vivax

<400> SEQUENCE: 275
aattgcgaac ggcgccggta atcagccggg ggcaaacggc gcgggtgatc aaccagggga    60
gct                                                                 63

<210> SEQ ID NO 276
<211> LENGTH: 55
<212> TYPE: DNA
<213> ORGANISM: Plasmodium vivax

<400> SEQUENCE: 276
cccctggttg atcacccgcg ccgtttgccc ccggctgatt accggcgccg ttcgc         55

<210> SEQ ID NO 277
<211> LENGTH: 21
<212> TYPE: PRT
<213> ORGANISM: Plasmodium vivax

<400> SEQUENCE: 277

Ile Ala Asn Gly Ala Asp Asn Gln Pro Gly Ala Asn Gly Ala Asp Asp
1               5                   10                  15

Gln Pro Gly Glu Leu
            20

<210> SEQ ID NO 278
<211> LENGTH: 63
<212> TYPE: DNA
<213> ORGANISM: Plasmodium vivax

<400> SEQUENCE: 278
aattgcgaac ggcgccgata atcagccggg tgcaaacggg gcggatgacc aaccaggcga    60
gct                                                                 63

<210> SEQ ID NO 279
<211> LENGTH: 55
<212> TYPE: DNA
<213> ORGANISM: Plasmodium vivax

<400> SEQUENCE: 279
cgcctggttg gtcatccgcc ccgtttgcac ccggctgatt atcggcgccg ttcgc        55

<210> SEQ ID NO 280
<211> LENGTH: 39
<212> TYPE: PRT
<213> ORGANISM: Plasmodium vivax

<400> SEQUENCE: 280

Ile Ala Asn Gly Ala Gly Asn Gln Pro Gly Ala Asn Gly Ala Gly Asp
1               5                   10                  15

Gln Pro Gly Ala Asn Gly Ala Asp Asn Gln Pro Gly Ala Asn Gly Ala
            20                  25                  30

Asp Asp Gln Pro Gly Glu Leu
        35

<210> SEQ ID NO 281
<211> LENGTH: 117
<212> TYPE: DNA
<213> ORGANISM: Plasmodium vivax

<400> SEQUENCE: 281
aattgcgaac ggcgccggta atcagccggg agcaaacggc gcggggatc aaccaggcgc     60 caatggtgca gacaaccagc ctggggcgaa tggagccgat gaccaacccg gcgagct      117

<210> SEQ ID NO 282
<211> LENGTH: 109
<212> TYPE: DNA
<213> ORGANISM: Plasmodium vivax

<400> SEQUENCE: 282 cgccggggttg gtcatcggct ccattcgccc caggctggtt gtctgcacca ttggcgcctg   60
gttgatcccc cgcgccgttt gctcccggct gattaccggc gccgttcgc              109

<210> SEQ ID NO 283
<211> LENGTH: 25
<212> TYPE: PRT
<213> ORGANISM: Plasmodium vivax

<400> SEQUENCE: 283

Ile Ala Pro Gly Ala Asn Gln Glu Gly Gly Ala Ala Ala Pro Gly Ala
1               5                   10                  15

Asn Gln Glu Gly Gly Ala Ala Glu Leu
            20                  25

<210> SEQ ID NO 284
<211> LENGTH: 75
<212> TYPE: DNA
<213> ORGANISM: Plasmodium vivax

<400> SEQUENCE: 284
aattgcgccg ggcgccaacc aggaaggtgg ggctgcagcg ccaggagcca atcaagaagg    60
cggtgcagcg gagct                                                   75

<210> SEQ ID NO 285

```
<211> LENGTH: 67
<212> TYPE: DNA
<213> ORGANISM: Plasmodium vivax

<400> SEQUENCE: 285
ccgctgcacc gccttcttga ttggctcctg gcgctgcagc cccaccttcc tggttggcgc      60
ccggcgc                                                                67

<210> SEQ ID NO 286
<211> LENGTH: 203
<212> TYPE: PRT
<213> ORGANISM: Artificial Sequence
<220> FEATURE:
<223> OTHER INFORMATION: HBc chimer

<400> SEQUENCE: 286
```

Met Ser Leu Leu Thr Glu Val Glu Thr Pro Ile Arg Asn Glu Trp Gly
1               5                   10                  15

Cys Arg Cys Asn Asp Ser Ser Asp Pro Tyr Lys Glu Phe Gly Ala Thr
            20                  25                  30

Val Glu Leu Leu Ser Phe Leu Pro Ser Asp Phe Phe Pro Ser Val Arg
        35                  40                  45

Asp Leu Leu Asp Thr Ala Ser Ala Leu Tyr Arg Glu Ala Leu Glu Ser
    50                  55                  60

Pro Glu His Cys Ser Pro His His Thr Ala Leu Arg Gln Ala Ile Leu
65                  70                  75                  80

Cys Trp Gly Glu Leu Met Thr Leu Ala Thr Trp Val Gly Val Asn Leu
                85                  90                  95

Glu Asp Pro Ala Ser Arg Asp Leu Val Val Ser Tyr Val Asn Thr Asn
            100                 105                 110

Met Gly Leu Lys Phe Arg Gln Leu Leu Trp Phe His Ile Ser Cys Leu
        115                 120                 125

Thr Phe Gly Arg Glu Thr Val Ile Glu Tyr Leu Val Ser Phe Gly Val
    130                 135                 140

Trp Ile Arg Thr Pro Pro Ala Tyr Arg Pro Pro Asn Ala Pro Ile Leu
145                 150                 155                 160

Ser Thr Leu Pro Glu Thr Thr Val Val Arg Arg Gly Arg Ser Pro
                165                 170                 175

Arg Arg Arg Thr Pro Ser Pro Arg Arg Arg Ser Gln Ser Pro Arg
            180                 185                 190

Arg Arg Arg Ser Gln Ser Arg Glu Ser Gln Cys
        195                 200

```
<210> SEQ ID NO 287
<211> LENGTH: 176
<212> TYPE: PRT
<213> ORGANISM: Artificial Sequence
<220> FEATURE:
<223> OTHER INFORMATION: HBc chimer

<400> SEQUENCE: 287
```

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu

-continued

```
                  50                  55                  60
Leu Met Thr Leu Ala Thr Trp Val Gly Val Asn Leu Glu Asp Gly Ile
 65                  70                  75                  80

Ser Leu Leu Thr Glu Val Glu Thr Pro Ile Arg Asn Glu Trp Gly Cys
                 85                  90                  95

Arg Cys Asn Asp Ser Ser Asp Glu Leu Pro Ala Ser Arg Asp Leu Val
                100                 105                 110

Val Ser Tyr Val Asn Thr Asn Met Gly Leu Lys Phe Arg Gln Leu Leu
                115                 120                 125

Trp Phe His Ile Ser Cys Leu Thr Phe Gly Arg Glu Thr Val Ile Glu
            130                 135                 140

Tyr Leu Val Ser Phe Gly Val Trp Ile Arg Thr Pro Pro Ala Tyr Arg
145                 150                 155                 160

Pro Pro Asn Ala Pro Ile Leu Ser Thr Leu Pro Glu Thr Thr Val Val
                165                 170                 175

<210> SEQ ID NO 288
<211> LENGTH: 177
<212> TYPE: PRT
<213> ORGANISM: Artificial Sequence
<220> FEATURE:
<223> OTHER INFORMATION: HBc chimer

<400> SEQUENCE: 288

Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Val Asn Leu Glu Asp Gly Ile
 65                  70                  75                  80

Ser Leu Leu Thr Glu Val Glu Thr Pro Ile Arg Asn Glu Trp Gly Cys
                 85                  90                  95

Arg Cys Asn Asp Ser Ser Asp Glu Leu Pro Ala Ser Arg Asp Leu Val
                100                 105                 110

Val Ser Tyr Val Asn Thr Asn Met Gly Leu Lys Phe Arg Gln Leu Leu
                115                 120                 125

Trp Phe His Ile Ser Cys Leu Thr Phe Gly Arg Glu Thr Val Ile Glu
            130                 135                 140

Tyr Leu Val Ser Phe Gly Val Trp Ile Arg Thr Pro Pro Ala Tyr Arg
145                 150                 155                 160

Pro Pro Asn Ala Pro Ile Leu Ser Thr Leu Pro Glu Thr Thr Val Val
                165                 170                 175

Cys

<210> SEQ ID NO 289
<211> LENGTH: 183
<212> TYPE: PRT
<213> ORGANISM: Artificial Sequence
<220> FEATURE:
<223> OTHER INFORMATION: HBc chimer

<400> SEQUENCE: 289

Met Gly Ile Ser Leu Leu Thr Glu Val Glu Thr Pro Ile Arg Asn Glu
```

```
                1               5              10              15
Trp Gly Cys Arg Cys Asn Asp Ser Ser Asp Glu Leu Leu Gly Trp Leu
                20                      25                      30

Trp Gly Ile Asp Ile Asp Pro Tyr Lys Glu Phe Gly Ala Thr Val Glu
                35                      40                  45

Leu Leu Ser Phe Leu Pro Ser Asp Phe Phe Pro Ser Val Arg Asp Leu
        50                      55                      60

Leu Asp Thr Ala Ser Ala Leu Tyr Arg Glu Ala Leu Glu Ser Pro Glu
65                      70                      75                  80

His Cys Ser Pro His His Thr Ala Leu Arg Gln Ala Ile Leu Cys Trp
                    85                      90                  95

Gly Glu Leu Met Thr Leu Ala Thr Trp Val Gly Val Asn Leu Glu Asp
                100                     105                 110

Pro Ala Ser Arg Asp Leu Val Val Ser Tyr Val Asn Thr Asn Met Gly
                115                     120                 125

Leu Lys Phe Arg Gln Leu Leu Trp Phe His Ile Ser Cys Leu Thr Phe
        130                     135                     140

Gly Arg Glu Thr Val Ile Glu Tyr Leu Val Ser Phe Gly Val Trp Ile
145                     150                     155                 160

Arg Thr Pro Pro Ala Tyr Arg Pro Pro Asn Ala Pro Ile Leu Ser Thr
                    165                     170                 175

Leu Pro Glu Thr Thr Val Val
                180

<210> SEQ ID NO 290
<211> LENGTH: 184
<212> TYPE: PRT
<213> ORGANISM: Artificial Sequence
<220> FEATURE:
<223> OTHER INFORMATION: HBc chimer

<400> SEQUENCE: 290

Met Gly Ile Ser Leu Leu Thr Glu Val Glu Thr Pro Ile Arg Asn Glu
1               5              10                      15

Trp Gly Cys Arg Cys Asn Asp Ser Ser Asp Glu Leu Leu Gly Trp Leu
                20                      25                      30

Trp Gly Ile Asp Ile Asp Pro Tyr Lys Glu Phe Gly Ala Thr Val Glu
                35                      40                  45

Leu Leu Ser Phe Leu Pro Ser Asp Phe Phe Pro Ser Val Arg Asp Leu
        50                      55                      60

Leu Asp Thr Ala Ser Ala Leu Tyr Arg Glu Ala Leu Glu Ser Pro Glu
65                      70                      75                  80

His Cys Ser Pro His His Thr Ala Leu Arg Gln Ala Ile Leu Cys Trp
                    85                      90                  95

Gly Glu Leu Met Thr Leu Ala Thr Trp Val Gly Val Asn Leu Glu Asp
                100                     105                 110

Pro Ala Ser Arg Asp Leu Val Val Ser Tyr Val Asn Thr Asn Met Gly
                115                     120                 125

Leu Lys Phe Arg Gln Leu Leu Trp Phe His Ile Ser Cys Leu Thr Phe
        130                     135                     140

Gly Arg Glu Thr Val Ile Glu Tyr Leu Val Ser Phe Gly Val Trp Ile
145                     150                     155                 160

Arg Thr Pro Pro Ala Tyr Arg Pro Pro Asn Ala Pro Ile Leu Ser Thr
                    165                     170                 175

Leu Pro Glu Thr Thr Val Val Cys
```

180

<210> SEQ ID NO 291
<211> LENGTH: 18
<212> TYPE: PRT
<213> ORGANISM: Artificial Sequence
<220> FEATURE:
<223> OTHER INFORMATION: Amplification primer containing a restriction endonuclease site

<400> SEQUENCE: 291

Met Gly Ser Arg Cys Asn Asp Ser Ser Asp Ile Asp Pro Tyr Lys Glu
1               5                   10                  15

Phe Gly

<210> SEQ ID NO 292
<211> LENGTH: 59
<212> TYPE: DNA
<213> ORGANISM: Artificial Sequence
<220> FEATURE:
<223> OTHER INFORMATION: Amplification primer containing a restriction endonuclease site

<400> SEQUENCE: 292
ggcgccatgg ggtctagatg taacgattca agtgacatcg acccttataa agaatttcg        59

<210> SEQ ID NO 293
<211> LENGTH: 16
<212> TYPE: PRT
<213> ORGANISM: Artificial Sequence
<220> FEATURE:
<223> OTHER INFORMATION: Amplification primer containing a restriction endonuclease site

<400> SEQUENCE: 293

Met Gly Cys Asn Asp Ser Ser Asp Ile Asp Pro Tyr Lys Glu Phe Gly
1               5                   10                  15

<210> SEQ ID NO 294
<211> LENGTH: 52
<212> TYPE: DNA
<213> ORGANISM: Artificial Sequence
<220> FEATURE:
<223> OTHER INFORMATION: Amplification primer containing a restriction endonuclease site

<400> SEQUENCE: 294
gcgccatggg gtgtaacgat tcaagtgaca tcgacccctta taaagaattt gg              52

<210> SEQ ID NO 295
<211> LENGTH: 14
<212> TYPE: PRT
<213> ORGANISM: Artificial Sequence
<220> FEATURE:
<223> OTHER INFORMATION: Amplification primer containing a restriction endonuclease site

<400> SEQUENCE: 295

Ser Lys Leu Cys Leu Gly Trp Leu Trp Gly Met Asp Ile Asp
1               5                   10

<210> SEQ ID NO 296
<211> LENGTH: 27
<212> TYPE: PRT
<213> ORGANISM: Artificial Sequence
<220> FEATURE:
<223> OTHER INFORMATION: Amplification primer containing a restriction -continued endonuclease site

<400> SEQUENCE: 296

Met Ser Leu Leu Thr Glu Val Glu Thr Pro Ile Arg Asn Glu Trp Gly
1               5                   10                  15

Cys Arg Cys Asn Asp Ser Ser Asp Glu Leu Asp
            20                  25

<210> SEQ ID NO 297
<211> LENGTH: 27
<212> TYPE: PRT
<213> ORGANISM: Artificial Sequence
<220> FEATURE:
<223> OTHER INFORMATION: Amplification primer containing a restriction
      endonuclease site

<400> SEQUENCE: 297

Met Ser Leu Leu Thr Glu Val Glu Thr Pro Ile Arg Asn Glu Trp Gly
1               5                   10                  15

Ser Arg Ser Asn Asp Ser Ser Asp Glu Leu Asp
            20                  25

<210> SEQ ID NO 298
<211> LENGTH: 38
<212> TYPE: PRT
<213> ORGANISM: Artificial Sequence
<220> FEATURE:
<223> OTHER INFORMATION: Amplification primer containing a restriction
      endonuclease site

<400> SEQUENCE: 298

Met Gly Ile Ser Leu Leu Thr Glu Val Glu Thr Pro Ile Arg Asn Glu
1               5                   10                  15

Trp Gly Cys Arg Cys Asn Asp Ser Ser Asp Glu Leu Leu Gly Trp Leu
            20                  25                  30

Trp Gly Ile Asp Ile Asp
        35

<210> SEQ ID NO 299
<211> LENGTH: 52
<212> TYPE: PRT
<213> ORGANISM: Artificial Sequence
<220> FEATURE:
<223> OTHER INFORMATION: Amplification primer containing a restriction
      endonuclease site

<400> SEQUENCE: 299

Gly Cys Gly Ala Ala Gly Cys Thr Thr Ala Cys Thr Ala Ala Gly Gly
1               5                   10                  15

Gly Gly Ala Gly Cys Gly Gly Cys Cys Thr Cys Gly Thr Cys Gly Ala
            20                  25                  30

Cys Gly Ala Ala Cys Ala Ala Cys Ala Gly Thr Ala Gly Thr Cys Thr
        35                  40                  45

Cys Cys Gly Gly
    50

<210> SEQ ID NO 300
<211> LENGTH: 55
<212> TYPE: PRT
<213> ORGANISM: Artificial Sequence
<220> FEATURE:
<223> OTHER INFORMATION: Amplification primer containing a restriction
      endonuclease site

```
<400> SEQUENCE: 300

Gly Cys Gly Ala Ala Gly Cys Thr Thr Ala Cys Thr Ala Ala Cys Ala
1               5                   10                  15

Ala Gly Gly Gly Gly Ala Gly Cys Gly Gly Cys Cys Thr Cys Gly Thr
            20                  25                  30

Cys Gly Ala Cys Gly Ala Ala Cys Ala Ala Cys Ala Gly Thr Ala Gly
        35                  40                  45

Thr Cys Thr Cys Cys Gly Gly
    50                  55

<210> SEQ ID NO 301
<211> LENGTH: 49
<212> TYPE: PRT
<213> ORGANISM: Artificial Sequence
<220> FEATURE:
<223> OTHER INFORMATION: Amplification primer containing a restriction
      endonuclease site

<400> SEQUENCE: 301

Gly Cys Gly Ala Ala Gly Cys Thr Thr Ala Cys Thr Ala Ala Gly Gly
1               5                   10                  15

Cys Gly Ala Gly Gly Ala Gly Thr Gly Cys Gly Cys Cys Gly Ala
            20                  25                  30

Cys Gly Ala Gly Gly Gly Ala Gly Cys Gly Gly Cys Cys Thr Cys
        35                  40                  45

Gly

<210> SEQ ID NO 302
<211> LENGTH: 52
<212> TYPE: PRT
<213> ORGANISM: Artificial Sequence
<220> FEATURE:
<223> OTHER INFORMATION: Amplification primer containing a restriction
      endonuclease site

<400> SEQUENCE: 302

Gly Cys Gly Ala Ala Gly Cys Thr Thr Ala Cys Thr Ala Ala Cys Ala
1               5                   10                  15

Ala Gly Gly Cys Gly Ala Gly Gly Ala Gly Thr Gly Cys Gly Cys
            20                  25                  30

Cys Gly Ala Cys Gly Ala Gly Gly Gly Ala Gly Cys Gly Gly Cys
        35                  40                  45

Cys Thr Cys Gly
    50

<210> SEQ ID NO 303
<211> LENGTH: 49
<212> TYPE: PRT
<213> ORGANISM: Artificial Sequence
<220> FEATURE:
<223> OTHER INFORMATION: Amplification primer containing a restriction
      endonuclease site

<400> SEQUENCE: 303

Gly Cys Gly Ala Ala Gly Cys Thr Thr Ala Cys Thr Ala Cys Gly Gly
1               5                   10                  15

Cys Gly Ala Thr Thr Gly Ala Gly Ala Gly Cys Gly Thr Cys Gly Ala
            20                  25                  30

Cys Gly Gly Cys Gly Ala Gly Gly Cys Gly Ala Gly Gly Ala Gly
        35                  40                  45
```

Thr

<210> SEQ ID NO 304
<211> LENGTH: 52
<212> TYPE: PRT
<213> ORGANISM: Artificial Sequence
<220> FEATURE:
<223> OTHER INFORMATION: Amplification primer containing a restriction
      endonuclease site

<400> SEQUENCE: 304

Gly Cys Gly Ala Ala Gly Cys Thr Thr Ala Cys Thr Ala Ala Cys Ala
1               5                   10                  15

Cys Gly Gly Cys Gly Ala Thr Thr Gly Ala Gly Ala Gly Cys Gly Thr
            20                  25                  30

Cys Gly Ala Cys Gly Gly Cys Gly Ala Gly Gly Cys Gly Ala Gly Gly
        35                  40                  45

Gly Ala Gly Thr
    50

<210> SEQ ID NO 305
<211> LENGTH: 66
<212> TYPE: PRT
<213> ORGANISM: Artificial Sequence
<220> FEATURE:
<223> OTHER INFORMATION: Amplification primer containing a restriction
      endonuclease site

<400> SEQUENCE: 305

Gly Cys Gly Ala Ala Gly Cys Thr Thr Ala Cys Thr Ala Ala Cys Ala
1               5                   10                  15

Thr Thr Gly Ala Gly Ala Thr Thr Cys Cys Cys Gly Ala Gly Ala Thr
            20                  25                  30

Thr Gly Ala Gly Ala Thr Cys Gly Cys Gly Gly Cys Gly Ala Cys
        35                  40                  45

Gly Cys Gly Gly Cys Gly Ala Thr Thr Gly Ala Gly Ala Gly Cys Gly
    50                  55                  60

Thr Cys
65

<210> SEQ ID NO 306
<211> LENGTH: 32
<212> TYPE: PRT
<213> ORGANISM: Artificial Sequence
<220> FEATURE:
<223> OTHER INFORMATION: Amplification primer containing a restriction
      endonuclease site

<400> SEQUENCE: 306

Gly Cys Gly Ala Ala Gly Cys Thr Thr Ala Cys Thr Ala Thr Thr Gly
1               5                   10                  15

Ala Gly Ala Thr Thr Cys Cys Cys Gly Ala Gly Ala Thr Thr Gly Ala
            20                  25                  30

<210> SEQ ID NO 307
<211> LENGTH: 28
<212> TYPE: PRT
<213> ORGANISM: Artificial Sequence
<220> FEATURE:
<223> OTHER INFORMATION: Amplification primer containing a restriction
      endonuclease site

<400> SEQUENCE: 307

```
Gly Gly Ala Ala Ala Gly Cys Thr Thr Ala Cys Thr Ala Ala Cys Ala
1               5                   10                  15

Thr Thr Gly Ala Gly Ala Thr Thr Cys Cys Cys Gly
            20                  25

<210> SEQ ID NO 308
<211> LENGTH: 37
<212> TYPE: PRT
<213> ORGANISM: Artificial Sequence
<220> FEATURE:
<223> OTHER INFORMATION: Amplification primer containing a restriction
      endonuclease site

<400> SEQUENCE: 308

Cys Gly Cys Ala Ala Gly Cys Thr Thr Ala Cys Thr Ala Gly Cys Ala
1               5                   10                  15

Ala Ala Cys Ala Ala Cys Ala Gly Thr Ala Gly Thr Cys Thr Cys Cys
            20                  25                  30

Gly Gly Ala Ala Gly
            35
```